(12) United States Patent
Huang et al.

(10) Patent No.: US 11,229,642 B2
(45) Date of Patent: Jan. 25, 2022

(54) COMPOSITION AND METHOD FOR REDUCING NEUTROPENIA

(71) Applicant: BeyondSpring Pharmaceuticals, Inc., New York, NY (US)

(72) Inventors: Lan Huang, Bronx, NY (US); George Kenneth Lloyd, San Carlos, CA (US); Ramon Mohanlal, New York, NY (US)

(73) Assignee: BeyondSpring Pharmaceuticals, Inc., New York, NY (US)

( * ) Notice: Subject to any disclaimer, the term of this patent is extended or adjusted under 35 U.S.C. 154(b) by 101 days.

(21) Appl. No.: 16/307,440

(22) PCT Filed: Jun. 5, 2017

(86) PCT No.: PCT/US2017/035991
§ 371 (c)(1),
(2) Date: Dec. 5, 2018

(87) PCT Pub. No.: WO2017/214052
PCT Pub. Date: Dec. 14, 2017

(65) Prior Publication Data
US 2019/0175587 A1 Jun. 13, 2019

Related U.S. Application Data

(60) Provisional application No. 62/346,426, filed on Jun. 6, 2016, provisional application No. 62/454,628, filed on Feb. 3, 2017.

(51) Int. Cl.
| | |
|---|---|
| *A61K 31/496* | (2006.01) |
| *A61K 31/337* | (2006.01) |
| *A61P 35/00* | (2006.01) |
| *A61K 45/06* | (2006.01) |
| *A61K 31/704* | (2006.01) |
| *A61K 33/243* | (2019.01) |
| *A61K 31/664* | (2006.01) |
| *A61K 31/4745* | (2006.01) |
| *A61K 31/675* | (2006.01) |
| *A61P 39/00* | (2006.01) |
| *A61K 31/351* | (2006.01) |
| *A61N 5/10* | (2006.01) |

(52) U.S. Cl.
CPC .......... *A61K 31/496* (2013.01); *A61K 31/337* (2013.01); *A61K 31/351* (2013.01); *A61K 31/4745* (2013.01); *A61K 31/664* (2013.01); *A61K 31/675* (2013.01); *A61K 31/704* (2013.01); *A61K 33/243* (2019.01); *A61K 45/06* (2013.01); *A61N 5/10* (2013.01); *A61P 35/00* (2018.01); *A61P 39/00* (2018.01)

(58) Field of Classification Search
CPC .................................................. A61K 31/496
See application file for complete search history.

(56) References Cited

U.S. PATENT DOCUMENTS

| | | | |
|---|---|---|---|
| 4,535,183 A | 8/1985 | Kneen | |
| 5,607,934 A | 3/1997 | Tone et al. | |
| 5,733,888 A | 3/1998 | Carver et al. | |
| 5,852,018 A | 12/1998 | Bryans et al. | |
| 5,872,151 A | 2/1999 | Rhodes | |
| 5,874,443 A | 2/1999 | Kiely et al. | |
| 5,886,210 A | 3/1999 | Rayle et al. | |
| 5,891,877 A | 4/1999 | Brocchini et al. | |
| 5,922,683 A | 7/1999 | Or et al. | |
| 5,939,098 A | 8/1999 | Reidenberg et al. | |
| 5,958,980 A | 9/1999 | Rhodes | |
| 6,069,146 A | 5/2000 | Fenical et al. | |
| 6,096,786 A | 8/2000 | Rhodes | |
| 6,350,759 B1 | 2/2002 | Casara et al. | |
| 6,358,957 B1 | 3/2002 | Fukumoto et al. | |
| 6,500,825 B2 | 12/2002 | Lan et al. | |
| 6,506,787 B2 | 1/2003 | Fujishita et al. | |
| 6,509,331 B1 | 1/2003 | Audia et al. | |
| 6,583,143 B2 | 6/2003 | Haddach | |
| 6,713,480 B2 | 3/2004 | Fukumoto et al. | |
| 6,808,710 B1 | 10/2004 | Wood et al. | |
| 6,972,289 B1 | 12/2005 | Kanzaki et al. | |
| 7,026,322 B2 | 4/2006 | Hayashi et al. | |
| 7,064,201 B2 * | 6/2006 | Hayashi ............... | C07D 409/14 544/8 |
| 7,488,802 B2 | 2/2009 | Collins et al. | |
| 7,629,380 B2 | 12/2009 | McMorris et al. | |
| 7,635,757 B2 | 12/2009 | Freeman et al. | |
| 7,674,903 B2 | 3/2010 | Hayashi et al. | |

(Continued)

FOREIGN PATENT DOCUMENTS

| | | |
|---|---|---|
| EA | 016817 B1 | 7/2012 |
| EP | 0 054 924 | 6/1982 |

(Continued)

OTHER PUBLICATIONS

Nabholz (Journal of Clinical Oncology vol. 19 pp. 314-321 published 2001) (Year: 2001).*
Heist, R.S. et al. Randomized Phase 2 Trial of Plinabulin (NPI-2358) Plus Docetaxel in Patients with Advanced Non-Small Lung Cancer (NSCLC). 2014 ASCO Annual Meeting . . . (abstr 8054) poster. Retrieved from the internet Jul. 17, 2017: <http://meetinglibrary.asco.org/record/92548/poster>.
Lyman, G.H. et al. 'Risk models for predicting chemotherapy-induced neutropenia'. The Oncologist. 2005. 10: 427-437.

(Continued)

*Primary Examiner* — Theodore R. Howell
*Assistant Examiner* — George W Kosturko
(74) *Attorney, Agent, or Firm* — Knobbe, Martens, Olson & Bear, LLP

(57) ABSTRACT

Disclosed herein are methods of reducing neutropenia that is caused by chemotherapy or radiation therapy by administering plinabulin to a subject.

25 Claims, 12 Drawing Sheets

(56) References Cited

U.S. PATENT DOCUMENTS

| | | | |
|---|---|---|---|
| 7,700,615 B2 | 4/2010 | Edwards et al. | |
| 7,919,497 B2 | 4/2011 | Palladino et al. | |
| 7,935,704 B2 | 5/2011 | Palladino et al. | |
| 7,943,743 B2 | 5/2011 | Korman et al. | |
| 7,956,058 B2 | 6/2011 | Hayashi et al. | |
| 8,008,449 B2 | 8/2011 | Korman et al. | |
| 8,129,527 B2 | 3/2012 | Palladino et al. | |
| 8,168,757 B2 | 5/2012 | Finnefrock et al. | |
| 8,217,149 B2 | 7/2012 | Irving et al. | |
| 8,247,552 B2 | 8/2012 | Palladino et al. | |
| 8,618,292 B2 * | 12/2013 | Palladino | C07D 413/14 544/406 |
| 9,358,289 B2 | 6/2016 | Korman et al. | |
| 9,394,368 B2 | 7/2016 | Brogdon et al. | |
| 10,076,518 B2 | 9/2018 | Huang | |
| 10,155,748 B2 | 12/2018 | Huang et al. | |
| 10,238,650 B2 | 3/2019 | Huang | |
| 10,357,491 B2 | 7/2019 | Huang | |
| 10,550,104 B2 | 2/2020 | Huang et al. | |
| 10,569,169 B2 * | 2/2020 | Li | G06F 9/544 |
| 10,596,169 B2 | 3/2020 | Huang | |
| 2002/0028819 A1 | 3/2002 | Teng et al. | |
| 2002/0143021 A1 | 10/2002 | Fukumoto et al. | |
| 2004/0102454 A1 | 5/2004 | Hayashi et al. | |
| 2006/0079534 A1 | 4/2006 | Kanzaki et al. | |
| 2006/0167010 A1 | 7/2006 | Hayashi et al. | |
| 2006/0223822 A1 | 10/2006 | Hayashi et al. | |
| 2007/0293453 A1 | 12/2007 | Fisher et al. | |
| 2008/0199485 A1 | 8/2008 | Kundig et al. | |
| 2008/0255035 A1 | 10/2008 | Trieu et al. | |
| 2009/0170837 A1 | 7/2009 | Gourdeau et al. | |
| 2009/0317368 A1 | 12/2009 | Chen | |
| 2012/0041070 A1 | 2/2012 | Shengfan et al. | |
| 2012/0277251 A1 | 11/2012 | Palladino et al. | |
| 2013/0303481 A1 | 11/2013 | Marcus | |
| 2014/0322275 A1 | 10/2014 | Brogdon et al. | |
| 2015/0202291 A1 | 7/2015 | Bosch et al. | |
| 2015/0291549 A1 | 10/2015 | Chupak et al. | |
| 2016/0243153 A1 | 8/2016 | Sundaram et al. | |
| 2017/0226221 A1 | 8/2017 | Madiyalakan et al. | |
| 2018/0028531 A1 | 2/2018 | Huang et al. | |
| 2019/0328727 A1 | 3/2019 | Huang | |
| 2019/0380983 A1 | 12/2019 | Mohanlal | |
| 2020/0038395 A1 | 2/2020 | Mohanlal | |
| 2020/0129504 A1 | 4/2020 | Mohanlal et al. | |
| 2020/0237754 A1 | 7/2020 | Huang | |
| 2020/0277280 A1 | 9/2020 | Huang | |
| 2020/0281921 A1 | 9/2020 | Huang | |
| 2020/0289503 A1 | 9/2020 | Huang | |
| 2021/0030843 A1 | 2/2021 | Mohanlal | |
| 2021/0046068 A1 | 2/2021 | Huang | |

FOREIGN PATENT DOCUMENTS

| | | | |
|---|---|---|---|
| EP | 0 655 060 | 1/1998 | |
| GB | 2143823 | 2/1985 | |
| JP | 05-9164 | 1/1993 | |
| JP | 05-255106 | 10/1993 | |
| JP | 10-130266 | 5/1998 | |
| JP | 2002-507612 A | 3/2002 | |
| RU | 2011 148 945 A | 4/2010 | |
| WO | WO 87/05297 | 9/1987 | |
| WO | WO 94/07479 | 4/1994 | |
| WO | WO 95/06077 | 3/1995 | |
| WO | WO 95/21832 | 8/1995 | |
| WO | WO 96/20190 | 7/1996 | |
| WO | WO 99/38844 | 8/1999 | |
| WO | WO 99/048889 | 9/1999 | |
| WO | WO 01/053290 | 7/2001 | |
| WO | WO 01/070663 | 9/2001 | |
| WO | WO 03/074550 | 9/2003 | |
| WO | WO 04/054498 | 7/2004 | |
| WO | WO-2004054498 A2 * | 7/2004 | C07D 401/14 |
| WO | WO 04/093831 | 11/2004 | |
| WO | WO 05/077940 | 8/2005 | |
| WO | WO 06/121168 | 11/2006 | |
| WO | WO 07/035841 | 3/2007 | |
| WO | WO 07/113648 | 10/2007 | |
| WO | WO 08/128169 | 10/2008 | |
| WO | WO 09/089260 | 7/2009 | |
| WO | WO 10/001169 | 1/2010 | |
| WO | WO 11/034954 | 3/2011 | |
| WO | WO 11/050344 | 5/2011 | |
| WO | WO 11/066389 | 6/2011 | |
| WO | WO 11/079507 | 7/2011 | |
| WO | WO 11/109625 | 9/2011 | |
| WO | WO 11/146382 | 11/2011 | |
| WO | WO 11/151423 | 12/2011 | |
| WO | WO 12/014549 | 2/2012 | |
| WO | WO 12/035436 | 3/2012 | |
| WO | WO 12/074904 | 6/2012 | |
| WO | WO 12/145493 | 10/2012 | |
| WO | WO 13/078537 | 6/2013 | |
| WO | WO 13/090552 | 6/2013 | |
| WO | WO 13/177633 | 12/2013 | |
| WO | WO 14/066834 | 5/2014 | |
| WO | WO 14/130657 | 8/2014 | |
| WO | WO 14/160183 | 10/2014 | |
| WO | WO 14/195852 | 12/2014 | |
| WO | WO 2015/051543 A1 | 4/2015 | |
| WO | WO-2015051543 A1 * | 4/2015 | A61P 35/00 |
| WO | WO 15/069770 | 5/2015 | |
| WO | WO 15/069790 | 5/2015 | |
| WO | WO 15/160641 | 10/2015 | |
| WO | WO 16/165007 | 10/2016 | |
| WO | WO 17/062505 | 4/2017 | |
| WO | WO 18/129381 | 7/2018 | |

OTHER PUBLICATIONS

Mita, A.C. et al. 'Phase II study of docetaxel with or without plinabulin (NPI-2358) in patients with non-small cell lung cancer (NSCLC)'.Journal of Clinical Oncology, 2010. 28(15). Supp. Abstract No. 7592.

Mohanlal, R. et al. 'The plinabulin/docetaxel combination to mitigate the known safety concerns of docetaxel'. Journal of Clinical Oncology, (published online before print) May 2016. 34 (Supp.15): Abstract: e20595.

International Search Report issued in application No. PCT/US2017/035991, dated Jul. 20, 2017.

Abels, Christoph, Targeting of the Vascular System of Solid Tumours by Photodynamic Therapy (PDT), Photochem Photobiol Sci., (Mar. 2004) 3: 765-771.

Abstracts of The 1999 Joint Chubu and Kansai Branch Conference and Symposia of Japan Society for Bioscience, Biotechnology, and Agrochemistry, (1999) p. 48.

Acquaviva et al., "Targeting KRAS-Mutant Non-Small Cell Lung Cancer with the Hsp90 Inhibitor Ganetespib", Mol Cancer Ther, Dec. 2012, 11(12), pp. 2633-2643.

Agarwal et al., "OP449, a Novel SET Antagonist, Is Cytotoxic to Leukemia Cells and Enhances Efficacy of Tyrosine Kinase Inhibitors in Drug-Resistant Myeloid Leukemias," pursuant to an EMBASE record for a Conference Abstract: 603. Oncogenes and Tumor Suppressors: Poster II (Nov. 15, 2013) Blood (2013) 122(21): 2511.

Aggarwal et al., Antiangiogenic agents in the management of non-small cell lung cancer: Where do we stand now and where are we headed? Cancer Biology & Therapy (2012), 13(5), 247-263.

Ahmed et al. "A new rapid and simple non-radioactive assay to monitor and determine the proliferation of lymphocytes: an alternative to [³H]thymidine incorporation assay." J. Immunol. Methods. 170, 211-224(1994).

Akerlund et al., "Diketopiperazine-Based Polymers from Common Amino Acids," Journal of Applied Polymer Science, (2000) 78 (12), 2213-2218.

Algaier et al. "The effects of dimethyl sulfoxide on the kinetics of tubulin assembly." Biochim. Biophys. Acta. 954, 235-43 (1988).

Ali et al. "Toxicity of echinulin from Aspergillus chevalieri in rabbits." Toxicology Letters. (1989) 48:235-41.

(56) References Cited

OTHER PUBLICATIONS

Asahina, T., "Spectrochemical Study of Amino-acid Anhydrides," Bulletin of the Chemical Society of Japan, (1930) 5, 354-365.
Augustin, M. "Die Umsetzung des 2,5-Diketopiperazins mit Aldehyden und Nitrosoverbindungen" Journal für Praktische Chemie, (1966) 32(4), 158-166.
Aviel-Ronen et al., "K-ras Mutations in Non-Small-Cell Lung Carcinoma: A Review," Clinical Lung Cancer (Jul. 2006) vol. 8, No. 1, pp. 30-38.
Bankowska et al., Derivatives of 1,2,3-triazole. Potential drugs?, Wiadomosci Chemiczne (2012), 66(11-12), 993-1022.
Beavis et al., "Dual PD-1 and CTLA-4 Checkpoint Blockade Promotes Antitumor Immune Responses through $CD4^+Foxp^3$- Cell-Mediated Modulation of $CD103^+$ Dendritic Cells," Cancer Immunol Res (Sep. 2018) 6(9):1069-1081.
Bergman et al., Ariloxy Substituted N-arylpiperazinones as Dual Inhibitors of Farnesyltransferase and Geranylgeranyltransferase-1, Bioorg & Med Chem Lttrs. (Mar. 2001) 11: 1411-1415.
Bertelsen et al., "Vascular effects of plinabulin (NPI-2358) and the influence on tumour response when given alone or combined with radiation." International Journal of Radiation Biology (2011),87(11), 1126-1134.
Bertino J., et al., "Principles of Cancer Therapy." Cecil Textbook of Medicine. Eds. Lee Goldman, et al. 21nd ed., (2000), Chapter 198, pp. 1060-1074.
Blayney et al., "Plinabulin, a Novel Small Molecule That Ameliorates Chemotherapy-Induced Neutropenia, Is Administered on the Same Day of Chemotherapy and Has Anticancer Efficacy", Meeting Info.: 58th Annual Meeting and Exposition of the American Society-of-Hematology (ASH), Blood (2016) 128(22): 2508.
Bond et al. "The Synthesis of Viridamine, a Penicillium Viridicatum Mycotoxin." Synthetic Commun. 19 (13&14), 2551-2566 (1989).
Borisy, G.G. "A Rapid Method for Quantitative Determination of Microtubule Protein using DEAE-Cellulose Filters." Anal. Biochem. 50, 373-385(1972).
Braga et al. "Crystal Polymorphism and Multiple Crystal Forms," Struct Bond (2009) 132:25-50.
Brahmer et al., "Safety and Activity of Anti-PD-L1 Antibody in Patients with Advanced Cancer," N Engl J Med (2012) 366:2455-2465.
Burtles, Sally, "Transition from Preclinical to first-in-man Phase", Expert Scientific Group on Phase One Clinical Trials Final Report, Presentation Jun. 19, 2006, pp. 35-38.
Cai, Small molecule vascular disrupting agents: potential new drugs for cancer treatment, a 2009 update, Frontiers in Anti-Cancer Drug Discovery (2010), 1, 380-427.
Cai, Sui X., "Small Molecule Vascular Disrupting Agents: Potential New Drugs for Cancer Treatment", Recent Pat Anticancer Drug Discov. (2007) 2(1): 79-101.
Callahan et al., "At the Bedside: CTLA-4- and PD-1-blocking antibodies in cancer immunotherapy", J Leukocyte Biol, vol. 94, Jul. 2013, pp. 41-53.
Carter et al., "No patient left behind: The promise of immune priming with epigenetic agents," Oncoimmunology (2017) vol. 6, No. 10, e1315486 (13 pages).
Chaplin et al., "Antivascular approaches to solid tumour thereapy: evaluation of tubulin binding agents", Br. J. Cancer 1996, 74 (Suppl. XXVII), S86-S88.
Chen et al., "Adjuvant effect of docetaxel on the immune responses to influenza A H1N1 vaccine in mice," BMC Immunology (2012) 13:36, pp. 1-12.
Chin et al., "Immune Intervention with Monoclonal Antibodies Targeting CD152 (CTLA-4) for Autoimmune and Malignant Diseases," Chang Gung Med J (Jan.-Feb. 2008) vol. 31, No. 1, pp. 1-15.
ClinicalTrials.gov Identifier NCT00892931, "Phase 2 study MPC-6827 for recurrent glioblastoma multiforme," (Oct. 14, 2011). [retrieved from internet on Jul. 30, 2019] <URL: https://clinicaltriais.gov/ct2/show/NCT00892931> 7 pages.
ClinicalTrials.gov Identifier NCT02846792, "Nivolumab and Plinabulin in Treating Patients With Stage IIIB-IV, Recurrent, or Metastatic Non-small Cell Lung Cancer," (Jul. 27, 2016). [retrieved from internet on Sep. 17, 2019], <URL: https://clinicaltrials.gov/ct2/show/NCT02846792?term=plinabuilin&rank=1> 11 pages.
Cole, P., "Durvalumab, Human anti-PD-L1 monoclonal antibody Immune checkpoint inhibitor Oncolytic", Drugs of the Future 2014, 39(12): pp. 843-847.
Cooper et al., "Response to BRAF Inhibition in Melanoma Is Enhanced When Combined with Immune Checkpoint Blockade," Published OnlineFirst Apr. 29, 2014; DOI: 10.1158/2326-6066.CIR-13-0215; Cancer Immunol Res (Jul. 2014) 2(7) 643-654.
Costa et al., "Analyses of selected safety endpoints in phase 1 and late-phase clinical trials of anti-PD-1 and PD-L1 inhibitors: prediction of immune-related toxicities," Oncotarget (2017) vol. 8, No. 40, pp. 67782-67789.
Cui et al. "Novel Mammalian Cell Cycle Inhibitors, Tryprostatins A, B and Other Diketopiperazines Produced by Aspergillus fumigatus." J. Antibiotics. 49(6), 534-40 (1996).
Cui et al. "Novel Mammalian Cell Cycle Inhibitors, Tryprostatins A, B and Other Diketopiperazines Produced by Aspergillus fumigatus." J. Antibiotics. 49(6): 527-33 (1996).
Davis et al., ZD6126: A Novel Vascular-targeting Agent That Causes Selective Destruction of Tumor Vasculature, Cancer Research (Dec. 15, 2002) 62: 7247-7253.
Dörwald, F., "Side Reactions in Organic Synthesis" Wiley-VCH Verlag GmbH & Co. KgaA, Weinheim, (2005), book cover and preface p. IX only.
Drug Approval and Licensing Procedures in Japan 2001, 2001, pp. 243-244.
Dunitz et al., "Disappearing Polymorphs," Acc. Chem. Res. (1995) vol. 28, No. 4, pp. 193-200.
Ferrer et al., Plinabulin: tubulin polymerization inhibitor vascular-disrupting agent oncolytic, Drugs of the Future (2010), 35(1), 11-15.
Folkes et al., Synthesis and In Vitro Evaluation of a Series of Diketopiperazine Inhibitors of Plasminogen Activator Inhibitor-1, Bioorg & Med Chem Lttrs., (Jul. 2001) 11: 2589-2592.
Frost et al., Novel Syngeneic Pseudo-orthotopic Prostate Cancer Model: Vascular, Mitotic and Apoptotic Responses to Castration, Microvasc Research (Dec. 2004) 69: 1 -9.
Fukushima et al., "Biological Activities of Albonoursin," J. Antibiotics, (1973) 26:175.
Gallina et al., "Condensation of 1,4-diacetylpiperazine-2,5-dione with aldehydes", Tetrahedron 1974, 30, 667-673.
Gameiro et al., "Exploitation of differential homeostatic proliferation of T-cell subsets following chemotherapy to enhance the efficacy of vaccine-mediated antitumor responses," Cancer Immunology Immunotherapy (2011) vol. 60, No. 9, pp. 1227-1242.
Garris et al., "Successful Anti-PD-1 Cancer Immunotherapy Requires T Cell-Dendritic Cell Crosstalk Involving the Cytokines IFN-( and IL-12," Immunity (Dec. 18, 2018) 49, pp. 1-14, e1-e7 (22 pages).
Goldani et al. "Treatment of murine pulmonary mucormycosis with SCH 42427, a broad-spectrum triazole antifungal drug", Correspondence, J Antimicrob Chemother. 33, 369-372 (1994).
Goldfarb et al., "Synthesis of β-2-thienylalanine," Izvestiya Akademii Nauk SSSR, Seriya Khimicheskaya, (1958) 98-100, as abstracted by CAPLUS.
Gordon et al. "Reductive Alkylation on a Solid Phase: Synthesis of a Piperazinedione Combinatorial Library." J. Bioorg. Med. Chem. Letters. 5, 47-50 (1995).
Granville et al., Release of Cytochrome c1 Bax Migration, Bid Cleavage, and Activation of Caspases 2, 3, 6, 7, 8, and 9 during Endothelial Cell Apoptosis, Am J Path., (Oct. 1999) 155(4):1021-1025.
Gridelli et al., Vascular disrupting agents: a novel mechanism of action in the battle against non-small cell lung cancer, Oncologist (2009), 14(6), 612-620.
Gu et al., "Identification of CTLA-4 isoforms produced by alternative splicing and their association with myasthenia gravis," Clinical Immunology (Sep. 2008) vol. 128, Issue 3, pp. 374-381.
Gura, Trisha, "Cancer Models: Systems for Identifying New Drugs are Often Faulty", Science 7(Nov. 1997) 278(5340): 1041-1042.
Hamel, E. "Antimitotic Natural Products and Their Interactions with Tubulin." Med. Res. Rev. (1996) 16(2): 207-31.

(56) References Cited

OTHER PUBLICATIONS

Hartwell et al. "Checkpoints: Controls that Ensure the Order of Cell Cycle Events." Science. 246, 629-34 (1989).

Hayakawa, Structure-activity relationship analysis, Japnaese Journal of Cancer and Chemotherapy, (2004), 31(4):526-528.

Hayashi et al., "Total Synthesis of Anti-microtubule Diketopiperazine Derivatives: Phenylahistin and Aurantiamine," J. Org. Chem., (2000) 65: 8402-8405.

Hayashi et al., Medicinal chemistry and chemical biology of diketopiperazine-type antimicrotubule and vascular-disrupting agents, Chemical & Pharmaceutical Bulletin (2013), 61(9), 889-901.

Hayashi et al., Small peptide-based medicinal chemistry for intractable disease, Peptide Science (2009), vol. Date 2008, 45th, 139-140.

He et al., "Low-dose paclitaxel enhances the anti-tumor efficacy of GM-CSF surface-modified whole-tumor-cell vaccine in mouse model of prostate cancer," Cancer Immunology Immunotherapy (2011) vol. 60, No. 5, pp. 715-730. Abstract.

Heist et al., "Abstract C30: Phase 1/2 study of the vascular disrupting agent (VCA) plinabulin (NPI-2358) combined with docetaxel in patients with non-small cell lung cancer (NSCLC)," *Mol. Cancer Ther.,* 2009; 8(12 Suppl):C30, 2 pages.

Heist et al., "Randomized Phase 2 Trial of Plinabulin (NPI-2358) Plus Docetaxel in Patients with Advanced Non-Small Lung Cancer (NSCLC)," 2014 ASCO Annual Meeting . . . (abstr 8054) Poster Presentation. Retrieved from the internet Jul. 17, 2017: <http://meetinglibrary.asco.org/record/92548/poster>.

Helleman et al. "The International Journal of Biochemistry & Cell Biology," vol. 42, pp. 25-30 (2010).

Horak et al. "Structures of the Austalides A-E, Five Novel Toxic Metabolites from Aspergillus ustus." J Chem Soc Chem Commun. (1981) 1265-67.

http://scienceandresearch.homeoffice.gov.uk/animal-research/publications-and-reference/001-abstracts/abstracts2-2006/02november-2006/457?view=Html; "Abstract #457, Animals in Scientific Procedures (2006)"; (accessed on Nov. 19, 2008).

Hursthouse et al., "Why Do Organic Compounds Crystallise Well or Badly or Ever so Slowly? Why Is Crystallisation Nevertheless Such a Good Purification Technique?," Organic Process Res & Devel (2009) vol. 13, No. 6, pp. 1231-1240.

Hyun et al., "Valine dehydrogenase from *Streptomyces albus*: gene cloning, heterologous expression and identification of active site by site-directed mutagenesis," FEMS Microbiology Letters (Jan. 1, 2000) 182: 29-34.

Iwasaki, S. "Antimitotic Agents: Chemistry and Recognition of Tubulin Molecule." Med Res Rev. (1993) 13: 183-198.

Iwasaki, S. "Bioactive Natural Products Interfering with Microtubule Function." Kagaku to Seibutsu. 32(3): 153-159 (1994).

Ji et al., Tubulin Colchicine Binding Site Inhibitors as Vascular Disrupting Agents in Clinical Developments, Current Medicinal Chemistry (2015), 22(11), 1348-1360.

Jiang et al., "A Novel Peptide Isolated from a Phage Display Peptide Library with Trastuzumab Can Mimic Antigen Epitope of HER-2," (Feb. 11, 2005) J Biol Chem, vol. 280, No. 6, pp. 4656-4662.

Johnson et al. "Kinetic Analysis of Microtubule Self-assembly in Vitro." J. Mol. Biol. 117, 1-31 (1977).

Jure-Kunkel M. et al., "Synergy between chemotherapeutic agents and CTLA-4 blockade in preclinical tumor models", Cancer Immunol. Immunother. 2013, vol. 62, pp. 1533-1545.

Kakoulidou et al., "Human Soluble CD80 is Generated by Alternative Splicing, and Recombinant Soluble CD80 Binds to CD28 and CD152 Influencing T-cell Activation," Scandinavian J. Immunol (Nov. 2007) 66(5):529-537.

Kamb, Alexander, "What's wrong with our cancer models?", Nature Reviews Drug Discovery (Feb. 2005) 4: 161-165.

Kanoh et al., "(−)-Phenylahistin: A New Mammalian Cell Cycle Inhibitor Produced by Aspergillus ustus," Bioorganic & Medicinal Chemistry Letters, (1997) 7: 2847-2852.

Kanoh et al., "(−)-Phenylahistin Arrests Cells in Mitosis by Inhibiting Tubulin Polymerization," The Journal of Antibiotics, (1999) 52: 134-41.

Kanoh et al., "Antitumor Activity of Phenylahistin in Vitro and in Vivo," Bioscience Biotechnology Biochemistry, (1999) 63(6): 1130-1133.

Kanoh et al., "Synthesis and Biological Activities of Phenylahistin Derivatives," Bioorganic & Medicinal Chemistry, (1999) 7: 1451-1457.

Kanthou et al., Microtubule depolymerizing vascular disrupting agents: novel therapeutic agents for oncology and other pathologies, International Journal of Experimental Pathology(2009), 90(3), 284-294.

Kanzaki et al., "Effective Production of Dehydro Cyclic Dipeptide Albonoursin Exhibiting Pronuclear Fusion Inhibitory Activity, I. Taxonomy and Fermentation," The Journal of Antibiotics, (1999) 52: 1017-1022.

Kanzaki et al., A Novel Potent Cell Cycle Inhibitor Dehydrophenylahistin-Enzymatic Synthesis and Inhibitory Activity toward Sea Urchin Embryo, The Journal of Antibiotics, (Dec. 2002) 55(12):1042-1047.

Kanzaki et al., "Effective Production of Dehydro Cyclic Dipeptide Albonoursin Exhibiting Pronuclear Fusion Inhibitory Activity, II. Biosynthetic and Bioconversion Studies." The Journal of Antibiotics, (2000) 53(1): 58-62.

Kanzaki et al., "Enzymatic dehydrogenation of cyclo(L-Phe-L-Leu) to a bioactive derivative, albonoursin," Journal of Molecular Catalysis B: Enzymatic (1999) 6(3): 265-270.

Kanzaki et al., "Enzymatic Synthesis of Physiologically Active Substances Utilizing a Novel System for the Synthesis of Diketopiperazines Comprising Dehydroamino Acids as Constituents," Abstracts of Papers Presented at the 1999 Meeting of the Society for Actinomycetes Japan, (1999) 42 (Abstract Only).

Kanzaki et al., "Novel Cyclic Dipeptide Dehydrogenase and Assay Method for Its Activity," Scientific Reports of the Faculty of Agriculture, Okayama University, (1999) 88: 7-11.

Keepers et al. "Comparison of the Sulforhodamine B Protein and Tetrazolium (MTT) Assays for in vitro Chemosensitivity Testing." Eur. J. Cancer. 27, 897-900 (1991).

Kim et al. "Polymer attached cyclic peptides, tetrahedron: Asymmetry." 3(11):1421-1430 (1992).

Kingston, Correction to Tubulin-interactive natural products as anticancer agents, Journal of Natural Products (2011), 74(5), 1352.

Kingston, Tubulin-Interactive Natural Products as Anticancer Agents. Journal of Natural Products (2009), 72(3), 507-515.

Kobayashi et al., "Microtubule Assembly Regulators of Microbial Origin," Abstract of Paper Read at the 1989 Symposium on the Chemistry of Natural Products, (1989) 51.

Kola et al., "Can the pharmaceutical industry reduce attrition rates?", Nature Reviews Drug Discovery (2004) 3: 711-715.

Kondoh et al. "Effects of Tryprostatin Derivatives on Microtubule Assembly In Viro and In Situ." J. Antibiotics. 51, 801-04(1998).

Kopple et al., "A Convenient Synthesis of 2,5-Piperazinediones1a," The Journal of Organic Chemistry, (1967) 33: 862-864.

Kreamer K., "Immune checkpoint blockade: A New Paradigm in Treating Advanced Cancer", J. Adv. Pract. Oncol., 2014, vol. 5, pp. 418-431.

Krishan, A. "Rapid Flow Cytofluorometric Analysis of Mammalian Cell Cycle by Propidium Iodide Staining." J. Cell Biol. 66, 188-193 (1975).

Kupchan et al. "Steganacin and Steganangin, Novel Antileukemic Lignan Lactones from Steganotaenia araliacea 1-3." J. Am. Chem. Soc. (1973) 95(4): 1335-36.

Küster & Koeppenhöfer, "Über eininge Pyrrolderivate," Z. Physiol, Chem., (1927) 172:126-137.

Lacey et al. "Interaction of Phomopsin A and Related Compounds with Purified Sheep Brain Tubulin." Biochem. Pharmacol. 36, 2133-38 (1987).

Laemmli, U.K. "Cleavage of Structural Proteins during the Assembly of the Head of Bacteriophage T4." Nature. 227, 680-85 (1970).

Larsen et al. "Aurantiamine, a Kiketopiperazine from Two Varieties of Penicillium Aurantiogriseum." Phytochemistry. 31, 1613-1615(1992).

(56) References Cited

OTHER PUBLICATIONS

Leaf, Clifton, "Why are we losing the war on cancer (And how to win it)?", Health Administrator (2005) XVII(1): 172-183.
Lee et al. "The Reconstitution of Microtubules from Purified Calf Brain Tubulin." Biochemistr. 14(23), 5183-87(1975).
Lee et al., "A practical guide to pharmaceutical polymorph screening & selection," Asian Journal of Pharmaceutical Sciences (2014) vol. 9, pp. 163-175.
Lee et al., Colchicine site inhibitors of microtubule integrity as vascular disrupting agents, Drug Development Research (2008), 69(6), 352-358.
Li, Y., et al. "Interaction of marine toxin dolastatin 10 with porcine brain tubulin: competitive inhibition of rhizoxin and phomopsin A binding." Chern. Biol. Interact. 93, 175-83 (1994).
Liao et al., "Design and synthesis of novel soluble 2,5-diketopiperazine derivatives as potential anticancer agents," European J Med Chem (2014) 83:236-244.
Liu et al., "The BRAF and MEK Inhibitors Dabrafenib and Trametinib: Effects on Immune Function and in Combination with Immunomodulatory Antibodies Targeting PD-1, PD-L1, and CTLA-4," Clin Cancer Res (2015) 21(7) 1639-1651.
Liwo et al. "Origin of the Ring-Ring Interaction in Cyclic Dipeptides Incorporating an Aromatic Amino Acid." Tetrahedron Lett. 26, 1873-1876 (1985).
Lloyd et al., Abstract A07: Plinabulin: Evidence for an immune-mediated mechanism of action, In: Proceedings of the AACR Special Conference: Function of Tumor Microenvironment in Cancer Progression; Jan. 7-10, 2016; San Diego, CA. Philadelphia (PA): AACR; Cancer Research. Aug. 2016. 76(15 Supp.): abstract nr A07.
Luduena, R.F. "Contrasting Roles of Tau and Microtubule-associated Protein 2 in the Vinblastine-induced Aggregation of Brain Tubulin." J. Biol. Chem. 259:12890-98 (1984).
Lynch et al., "Ipilimumab in Combination With Paclitaxel and Carboplatin as First-Line Treatment in Stage IIIB/IV Non-Small-Cell Lung Cancer: Results From a Randomized, Double-Blind, Multicenter Phase II Study," (Jun. 10, 2012) J Clin Oncol, vol. 30, No. 17, pp. 2046-2054.
Mahindroo et al., "Antitubulin Agents for the Treatment of Cancer—A Medicinal Chemistry Update", Expert Opin. Ther. Patents (2006) 16(5): 647-691.
Mahoney et al., "The Next Immune-Checkpoint Inhibitors: PD-1/PD-L1 Blockade in Melanoma," Clinical Therapeutics (Apr. 2015) vol. 37, Issue 4, pp. 764-782. Abstract.
Matsuda et al., "Pilot study of WT1 peptide-pulsed dendritic cell vaccination with docetaxel in esophageal cancer," Oncology Letters (Jul. 2018) vol. 16, No. 1, pp. 1348-1356.
Millward et al., "Phase I trial of NPI-2358 (a novel vascular disrupting agent) plus docetaxel," J. Clin. Oncol. (May 2009) 27(15S): 3571-3571, Abstract.
Millward et al., "Phase 1 study of the novel vascular disrupting agent plinabulin (NPI-2358) and docetaxel," The Journal of New Anticancer Agents, vol. 3, No. 30, Feb. 16, 2011 plinabulin (NPI-2358) and docetaxel, Investigational New Drugs (2011), 30(3), 1065-1073.
Mita et al., "Phase 1 First-in-Human Trial of the Vascular Disrupting Agent Plinabulin (NPI-2358) in Patients with Solid Tumors or Lymphomas," *Clinical Cancer Research* (2010), 16(23), 5892-5899.
Mita et al., Randomized Phase 2 Study of Docetaxel +/− Plinabulin (NPI-2358) in Patients with Non-Small Cell Lung Cancer (NSCLC), *Poster Presentation at ACS Annual '10 Meeting* (Jun. 4-8, 2010) 1 page.
Mitsudomi et al., "Mutations of ras genes distinguish a subset of non-small-cell lung cancer cell lines from small-cell lung cancer cell lines," *Oncogene* (Aug. 1991) vol. 6, No. 8, pp. 1352-1362.
Muguruma et al., OP-20: "Application of Fc-selective Z33-peptide to the preparation of non-covalent-type antibody-antimocrotubule plinabulin conjugate," 34th European Peptide Symposium 2016 & 8th International Peptide Symposium, Journal of Peptide Sci (Sep. 5, 2016—5:30pm) 22 Supplement 2 ISSN: 1099-1387 In English (Oral Presentation). Abstract.
Nagaria et al., "Flavopiridol Synergizes with Sorafenib to Induce Cytotoxicity and Potentiate Antitumorigenic Activity in EGFR/HER02 and Mutant RAS/RAF Breast Cancer Model Systems," Neoplasia (Aug. 2013) vol. 15, No. 8, pp. 939-951.
Neidle, Stephen, ed., Cancer Drug Design and Discovery, 9th Edition, Elsevier/Academic Press, (2008) Chapter 18, pp. 427-431.
Nema et al., Excipients and Their Role in Approved Injectable Products: Current Usage and Future Directions, PDA J Pharm Sci and Tech 2011, 65 287-332.
Neuteboom et al., "450 Poster NPI-2358, a novel tumor vascular disrupting agent potentiates the anti-tumor activity of docetaxel in the non small cell lung cancer model MV522," EJC Supplements (2008) 6(12):141.
Nicholson et al., NPI-2358 is a tubulin-depolymerizing agent: in-vitro evidence for activity as a tumor vascular-disrupting agent, Anti-Cancer Drugs (2005), vol. Date 2006, 17(1), 25-31.
Niemann et al., "The Synthesis of the Three Isomeric dl-β-Pyridylalanines" Journal of the American Chemical Society, (1942) 64(7):1678-1682.
Nihei et al., "Evaluation of antivascular and antimitotic effects of tubulin binding agents in solid tumor therapy", Jpn. J. Cancer. Res. 1999, 90, 1387-1395.
Nitecki et al., "A Simple Route to Sterically Pure Diketopiperazines1," The Journal of Organic Chemistry, (1968) 33:864-866.
Ohaegbulam et al., "Human cancer immunotherapy with antibodies to the PD-1 and PD-L1 pathway," Trends Mol Med, (Oct. 30, 2014) 21(1): pp. 24-33.
Ott et al., "CTLA-4 and PD-1/PD-L1 Blockade: New Immunotherapeutic Modalities with Durable Clinical Benefit in Melanoma Patients," Ciin Cancer Res (Oct. 1, 2013) 19(19): pp. 5300-5309.
Paik et al., "A Phase 2 Study of Weekly Albumin-Bound Paclitaxel (Abraxane®) Given as a Two-Hour Infusion", Cancer Chemother. Pharmacol., Nov. 2011, vol. 68, No. 5, pp. 1331-1337.
Pardoll et al., "The blockade of immune checkpoints in cancer immunotherapy," Nat Rev Cancer (May 4, 2016) 12(4): 252-264.
Pattingre et al., "Amino Acids Interfere with the ERK1/2-dependent Control of Macroautophagy by Controlling the Activation of Raf-1 in Human Colon Cancer HT-29 Cells," J Biol Chem (May 9, 2003) vol. 278, No. 19, p. 16667-16674.
Perez, Edith A., "Paclitaxel in Breast Cancer," *The Oncologist*, 1998, vol. 3, pp. 373-389.
Petrillo et al., Novel VEGF-independent strategies targeting tumor vasculature: clinical aspects, Current Pharmaceutical Design (2012), 18(19), 2702-2712.
Pettit et al. "Antineoplastic Agents. 291. Isolation and Synthesis of Combretastatins A-4, A-5, and A-6 1a." J. Med. Chem. (1995) 38: 1666-1672.
Prior et al., "A Comprehensive Survey of Ras Mutations in Cancer" *Cancer Res.* (2012) vol. 72, No. 10, pp. 24570-2467.
Raza et al., 2014, Polymorphism: the phenomenon affecting the performance of drugs, SOJ Pharmacy & Pharmaceutical Sciences, 10 pp.
Reck, M., "What future opportunities may immuno-oncology provide for improving the treatment of patients with lung cancer?" (2012) Annals of Oncology (Sep. 2012) 23 (Supp. 8) viii28-viii34.
Remington, "The Science and Practice of Pharmacy, 20th Ed" (2000) p. 709.
Rhodes, John, "Section Review: Biologicals & Immunologicals: Therapeutic potential of Schiff base-forming drugs," Expert Opinion on Investigational Drugs (1996) vol. 5, Issue 3, pp. 257-268.
Riemer et al., "Matching of trastuzumab (Herceptin®) epitope mimics onto the surface of Her-2/neu—a new method of epitope definition," Mol Immunol 42 (2005) pp. 1121-1124.
Roberge et al., "Antitumor Drug Fostriecin Inhibits the Mitotic Entry Checkpoint and Protein Phosphatases 1 and 2A." Cancer Res. 54,6115-21 (1994).
Roberts et al, "Trends in the Risks and Benefits to Patients with Cancer Participating in Phase 12 Clinical Trials", JAMA (2004) 292(17): 2130-2140.

(56) References Cited

OTHER PUBLICATIONS

Rowinsky et al., "The clinical pharmacology and use of antimicrotubule agents in cancer chemotherapeutics", Pharmacol. Ther. 1991, 52, 35-84.

Rowinsky et al. "Taxol: A Novel Investigational Antimicrotubule Agent." J. Natl. Cancer Inst. 82(15):1247-59(1990).

Rozali et al., "Programmed Death Ligand 2 in Cancer-Induced Immune Suppression," Clinical and Developmental Immunology (2012) Article ID 656340, pp. 1-8.

Sackett, D.L. "Podophyllotoxin, Steganacin and Combretastatin: Natural Products that Bind at the Colchicine Site of Tubulin." Pharmacol. Ther. (1993) 59: 163-228.

Saito et al., "Synthesis of novel octahydro-1, 5-imino-3-benzazocin-4, 7, 10-trione derivatives having a methyl group at the C-2 position as ABC ring models of saframycins," Chemical & Pharmaceutical Bulletin (1997) 45(7):1120-1129.

Scholl et al., "Synthetic Lethal Interaction between Oncogenic KRAS Dependency and the STK33 Suppression in Human Cancer Cells", Cell (May 29, 2009) 137 pp. 821-834.

Sezaki et al., "Drug Delivery Systems", Drug Development, (Jul. 1989) 13: 116, Table 2. 29.

Shen et al., NPI-2358 rapidly inhibit blood flow in tumor treatment by analyzing dynamic contrast enhanced magnetic resonance imaging parameters, Zhonghua Zhongliu Fangzhi Zazhi (2010), 17(7),488-490, 494.

Shen et al., Time- and dose-dependent vascular changes induced by the novel vascular disrupting drug NPI-2358 in a murine cancer model monitored with DCE-MRI, U.S. Chinese Journal of Lymphology and Qncotogy(2010), 9(4), 151-153.

Sherline et al. "Binding of Colchicine to Purified Microtubule Protein." J. Biol. Chem. 250, 5481-86 (1975).

Shi, Q et al, "Recent progress in the development of tubulin inhibitors as antimitotic antitumor agents", Curr. Pharm. Des. 1998, 4, 219-248.

Singh et al., "A novel vascular disrupting agent plinabulin triggers JNK-mediated apoptosis and inhibits angiogenesis in multiple myeloma cells," Blood (2011), 117(21), 5692-5700.

Siwicka et al., "Diastereodivergent Synthesis of 2,5-diketopiperazine Derivatives of Beta-Carboline and Isoquinoline from L-amino Acids," Tetrahedron: Asymmetry (Mar. 7, 2005) 16(5): 975-993.

Smedsgaard et al. "Using direct electrospray mass spectrometry in taxonomy and secondary metabolite profiling of crude fungal extracts." J. Microbiol. Meth. (1996) 25: 5-17.

Sölter et al., Barettin, Revisited? Tetrahed Lttrs. (Mar. 2002) 43: 3385-3386.

Spear et al., Vascular disrupting agents (VDA) in oncology: advancing towards new therapeutic paradigms in the clinic, Current Drug Targets (2011), 12(14), 2009-2015.

Stein, J., ed. "Internal Medicine," Fourth Edition, Mosby-Year Book, Inc., (1994), Chapters 71-72, pp. 699-729.

Stenehjem et al., "PDI/PDLI inhibitors for the treatment of advanced urothelial bladder cancer," OncoTargets and Therapy (2018) 11:5973-5989.

Steyn, P.S. "The Structures of Five Diketopiperazines from Aspergillus ustus." Tetrahedron. 29, 107-120 (1973).

Sugar et al. "Comparison of Three Methods of Antifungal Susceptibility Testing with the Proposed NCCLS Standard Broth Macrodilution Assay: Lack of Effect of Phenol Red." Diagn Micro and Infect Diseases. 21, 129-133 (1995).

Takahashi et al. "Rhizoxin binding to tubulin at the maytansine-binding site." Biochim. Biophys. Acta. 926, 215-23 (1987).

Talmadge et al., Murine models to evaluate novel and conventional therapeutic strategies for cancer., Am J Pathol, 2007, vol. 170, Issue 3, pp. 793-804.

Thorpe, Philip E., "Vascular Targeting Agents as Cancer Therapeutics," Clinical Cancer Research, vol. 10, 415-427, Jan. 15, 2004.

Tiwari et al. "A pH- and Temperature-Dependent Cycling Method that doubles the Yield of Microtubule Protein." Anal. Biochem. 215, 96-103 (1993).

Tonra et al., "Predictive models for tumour cell targeting with plinabulin, derived from in vitro screening and Affymetrix mRNA expression data," Proc Am Assoc Cancer Res (2019) vol. 60, p. 321, Abstract #1254.

Topalian et al., "Safety, Activity, and Immune Correlates of Anti-PD-1 Antibody in Cancer," N Engl J Med. (Jun. 28, 2012) 366(26):2443-2454.

Tozer et al., Tumour vascular disrupting agents: combating treatment Resistance, British Journal of Radiology (2008), 81(Spec. Iss. 1), S12-S20.

Turner et al. "Recent Advances in the Medicinal Chemistry of Antifungal Agents." Current Pharmaceutical Design. 2, 209-224 (1996).

University of Washington, "Nivolumab and Plinabuilin in Treating Patients With Stage IIIB-IV, Recurrent, or Metastatic Non-small Cell Lung Cancer," Clinical trial study first posted Jul. 27, 2016. URL:https://clinicaltrials.gov/ct2/show/NCT02846792.

US Food and Drug Administration, Highlights of prescribing information, retrieved Apr. 16, 2020 from https://www.accessdata.fda.gov/drugsatfda_docs/label/2015/125031s180lbl.pdf, Rev. Nov. 2015, Reference ID:4192944.

Usui et al. "Tryprostatin A, a specific and novel inhibitor of microtubule assembly." Biochem J. 333, 543-48(1998).

Van der Waerden, B.L., "Wirksamkeits- und Konzentrationsbestimmung durch Tierversuche." Arch Exp Pathol Pharmakol. 195, 389-412, (1940).

Verdier-Pinard et al., "Structure-Activity Analysis of the Interaction of Curacin A, the Potent Colchicine Site Antimitotic Agent, with Tubulin and Effects of Analogs on the Growth of MCF-7 breast Cancer Cells." Mol. Pharmacol., 53, 62-76 (1998).

Voskoglou-Nomikos et al., Clinical predictive value of the in vitro cell line, human xenograft, and mouse allograft preclinical cancer models, National Cancer Institute of Canada Clinical Trials Group et al., 2003, vol. 9, pp. 4227-4239.

Wang, T. et al. 1998 "Microtubule interfering agents activate c-Jun N-terminal kinase/stress-activated protein kinase through both Ras and apoptosis signal-regulating kinase pathways". J Biol Chem. vol. 273, No. 9, pp. 4928-4936.

Wang, Y. et al, "Structures of a diverse set of colchicine binding site inhibitors in complex with tubulin provide a rationale for drug discovery." FEBS Journal (2016) 283, 102-111.

Weisenberg et al. "The Colchicine-Binding Protein of Mammalian Brain and its Relation to Microtubules." Biochemistry (1968) 7(12): 4466-79.

Wilt et al. "Anal cancer in Alaska; a retrospective study of incidence, treatment, and outcomes". Alaska Med Jul.-Sep. 2002; 44(3):56-9, 62.

Yahara et al. "Microtubule Organization of Lymphocytes and its Modulation by Patch and Cap Formation." Cell. 15, 251-259(1978).

Yamato et al., "Clinical importance of B7-H3 expression in human pancreatic cancer," British Journal of Cancer (Oct. 20, 2009) 101, pp. 1709-1716.

Yamazaki et al. "Crystal Structure and Absolute Configuration of Fumitremorgin B, a Tremorgenic Toxin from Aspergillus fumigatus Fres." Tetrahedron Lett. 1, 27-28 (1975).

Yamazaki et al. "Synthesis and Structure-Activity Relationship Study of Antimicrotubule Agents Phenylahistin Derivatives and a Didehydropiperazine-2,5-dione Structure", Journal of Medicinal Chemistry, 2012, vol. 55, No. 3, pp. 1056-1071.

Yamazaki et al., Drug discovery study on cyclic dipeptides anti-cancer drugs and chemical biological development, Idenshi Igaku Mook (2012), 21(Saishin Pepuchido Gosei Gijutsu to Sono Soyaku Kenkyu eno Oyo), 260-266.

Yamori T., "A Human Cell Line Panel for Screening Anti-Cancer Drugs", Jap. J. Cancer Chemother. 24, 129-35(1997).

Yang et al., "The KRAS Mutation is Highly Correlated With EGFR Alterations in Patients With Non-small Cell Lung Cancer," Fooyin J Health Sci (2009) vol. 1(2): pp. 65-71.

Yeh et al., "A Phase 1 Trial Combining Plinabulin and Nivolumab for Metastatic Squamous NSCLC," International Association for the Study of Lung Cancer, Journal of Thoracic Oncology (Sep. 6, 2015) Abstract 602, p. 2.01-087.

(56) References Cited

OTHER PUBLICATIONS

Yin et al., "Human Mutations That Confer Paclitaxel Resistance," Mol. Cancer Ther. vol. 9(2), pp. 327-335 (2010).
Yokio et al, "Neihumicin, a New Cytotoxic Antibiotic From Micromonospora neihuensis," The Journal of Antibiotics, (Apr. 1988) 41(4):494-501.
Yoshida, M.M. Protein Nucleic Acid Enzymes. 38, 1753-1765 (1993).
Yoshimatsu et al. "Mechanism of Action of E7010, an Orally Active Sulfonamide Antitumor Agent: Inhibition of Mitosis by Binding to the Colchicine Site of Tubulin." Cancer Res. 57, 3208-13 (1997).
Younis et al., 2011, The cost-utility of adjuvant chemotherapy using docetaxel and cylophosphamide compared with doxorubicin and cyclophosphamide in breast cancer, Current Oncology 18(8):e298-3296.
Zawadzka et al., "Diastereoselective Synthesis of 1-Benzyltetrahydroisoquinoline Derivatives from Amino Acids by 1,4 Chirality Transfer", Euro J Org Chem., (Jul. 2003) 2003(13): 2443-2453.
Zheng, Lei, "Does vaccine-primed pancreatic cancer offer better candidates for immune-based therapies?" Immunotherapy (2014) 6(10):1017-1020.
Zou et al., Effect of Interleukin-1 Blockers, CK112, and CK116 on Rat Experimental Choroidal Neovascularization In Vivo and Endothelial Cell Cultures In Vitro, J Ocul Pharma Thera., (2006) 22(1):19-25.
"Definition of 'within'". [Online] [2015 Archived version accessed on Aug. 13, 2020 from https://web.archive.org/web/20151030162428/ https://dictionary.cambridge.org/us/dictionary/english/within. Cambridge English Dictionary. (Year: 2015).
Abolhasani et al., Jan. 2015, In-silico investigation of tubulin binding modes of a series of novel antiproliferative spiroisoxazoline compounds using docking studies, Iranian Journal of Pharmaceutical Research, 14(1):141-147.
Caira, 1998, Crystalline polymorphism of organic compounds, Topics in Current Chemistry, 198:163-208.
Crawford, Aug. 2003, Once-per-cycle pegilgrastim (neulata) for the management of chemotherapy-induced neutropenia, Seminars in Oncology 30(4)Suppl 13:23-30.
Dale, Oct. 2015, Neutropenia, John Wiley & Sons Ltd., www.els.net, 8 pp.
Fernandez-Medarde et al., Mar. 2011, Ras in cancer and developmental diseases, Genes & Cancer, 2(3):344-358.
Field et al., 2014, Microtubule-targeting agents are clinically successful due to both mitotic and interphase impairment of microtubule function, Bioorganic & Medicinal Chemistry, 22:5050-5059.
Krendel et al., Apr. 2002, Nucleotide exchange factor GEF-H1 mediates cross-talk between microtubules and the actin cytoskeleton, Nature Cell Biology, 4:294-301 and supplementary information.
Li et al., May-Jun. 2017, Epitope mapping reveals the binding mechanism of a functional antibody cross-reactive to both human and murine programmed death 1, MABS, 9(4):628-637.
Liou et al., Aug. 12, 2004, Concise synthesis and structure-activity relationships of combretastatin A-4 analogues, 1-aroylindoles and 3-aroylindoles, as novel classes of potent antitubulin agents, Journal of Medicinal Chemistry, 47(17):4247-4257.
Lu et al., Nov. 2012, An overview of tubulin inhibitors that interact with the colchicine binding site, Pharmaceutical Research, 29(11):2943-2971.
Melero et al., Aug. 2015, Evolving synergistic combinations of targeted immunotherapies to combat cancer, Nature Reviews Cancer, 15:457-472.
Mohanlal et al., Feb. 10, 2018, Plinabulin, a novel small molecule clinical stage I0 agent with anti-cancer activity, to prevent chemo-induced neutropenia and immune related AEs, Journal of Clinical Oncology, 36(5 Suppl):126.
Nielsen et al., Jun. 2005. Alternative splice variants of the human PD-1 gene, Cell Immunol., 235(2):109-116.
PRNewswire.com, Jun. 22, 2010, Nereus Pharmaceuticals completes enrollment of phase 2 advance clinical trial of plinabulin in non-small cell lung cancer, 4 pp.
Rathkopf, Jun. 20, 2008, Phase II trial of docetaxel with rapid androgen cycling for progressive noncastrate prostate cancer, J. Clin. Onc. 26(18):2959-2965.
Selby et al., Sep. 9, 2016, Preclinicai development of ipilimumab and nivolumab combination immunotherapy: mouse tumor models, in vitro functional studies, and cynomolgus macaque toxicology, PloS One, 11(9):e0161779, 19 pp.
Sele et al., Jul. 2016, Novel 4-(pyrimidin-2-yl)morpholines targeting the colchicine-binding site of tubuline, Cancer Research, 76(14):abstract.
Spain et al., Feb. 6, 2016, Management of toxicities of immune checkpoint inhibitors, Cancer Treatment Reviews, 44:51-60.
Vainas, 2012, Personalising docetaxel and G-CSF schedules in cancer patients by a clinically validated computational model, British J. Cancer, 107:814-822.
Wailoo, 2009, The risk of febrile neutropenia in patients with non-small-cell lung cancer treated with docetaxel: a systematic review and meta-analysis, British J. Cancer 100(3):436-441.

\* cited by examiner

COMPOSITION AND METHOD FOR REDUCING NEUTROPENIA

INCORPORATION BY REFERENCE TO RELATED APPLICATIONS

This application is a U.S. National Stage application under 35 U.S.C. § 371 of International Application No. PCT/US2017/035991, which has an International Filing Date of Jun. 5, 2017, which claims the benefit of U.S. Provisional Application No. 62/346,426, filed Jun. 6, 2016 and entitled "COMPOSITION AND METHOD FOR REDUCING NEUTROPENIA," and U.S. Provisional Application No. 62/454,628, filed Feb. 3, 2017 and entitled "COMPOSITION AND METHOD FOR REDUCING NEUTROPENIA," each of which is incorporated herein by reference in its entirety.

BACKGROUND

Field

The present invention relates to the field of chemistry and medicine. More particularly, the present invention relates to a method of reducing neutropenia.

Description of the Related Art

Several cancer therapies can have deleterious side effects. For example, many chemotherapeutic agents have myelosuppressive effects that can cause neutropenia. Similarly, radiation therapy can be a cause of neutropenia. There is a need for therapeutics that can counter the neutropenia caused by cancer therapy.

SUMMARY

Some embodiments disclosed herein include a method of reducing neutropenia in a subject, comprising administering plinabulin or a pharmaceutically acceptable salt thereof to the subject in need thereof, wherein the neutropenia is induced by administration of a first chemotherapeutic composition comprising one or more chemotherapeutic agents, wherein the chemotherapeutic composition does not comprise docetaxel, or by administration of radiation therapy.

BRIEF DESCRIPTION OF THE DRAWINGS

FIG. 11A shows the ANC levels when 0.25 mg/kg topotecan and 7.5 mg/kg plinabulin were administered; FIG. 11B shows the ANC levels when 1 mg/kg topotecan and 3.75 mg/kg plinabulin were administered.

DETAILED DESCRIPTION

Figure 1:
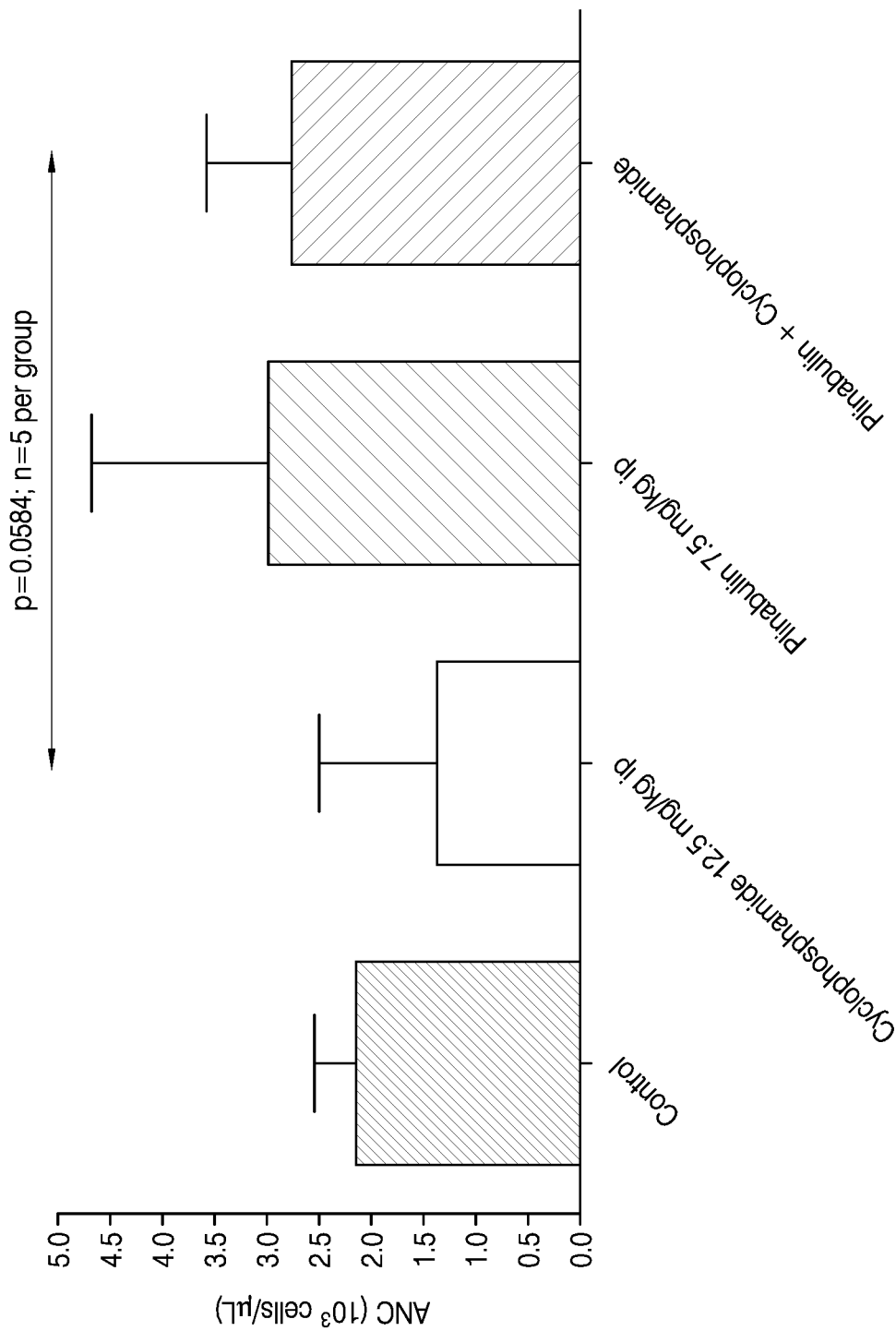
FIG. 1 is a graph of neutrophil count 24 hours post dosing of cyclophosphamide, plinabulin, or the combination of cyclophosphamide and plinabulin.

Plinabulin, (3Z,6Z)-3-Benzylidene-6-{[5-(2-methyl-2-propanyl)-1H-imidazol-4-yl]methylene}-2,5-piperazinedione, is a synthetic analog of the natural compound phenylahistin. Plinabulin can be readily prepared according to methods and procedures detailed in U.S. Pat. Nos. 7,064,201 and 7,919,497, which are incorporated herein by reference in their entireties. Some embodiments relate to the use of Plinabulin or a pharmaceutically effective salt thereof to reduce neutropenia. In some embodiments, the neutropenia is induced by chemotherapy, for example, by administration of drugs that have a myelosuppresive effect. In other embodiments, the neutropenia is induced by radiation therapy.

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

The term "mammal" is used in its usual biological sense. Thus, it specifically includes, but is not limited to, primates, including simians (chimpanzees, apes, monkeys) and humans, cattle, horses, sheep, goats, swine, rabbits, dogs, cats, rodents, rats, mice guinea pigs, or the like.

An "effective amount" or a "therapeutically effective amount" as used herein refers to an amount of a therapeutic agent that is effective to relieve, to some extent, or to reduce the likelihood of onset of, one or more of the symptoms of a disease or condition, and includes curing a disease or condition.

"Treat," "treatment," or "treating," as used herein refers to administering a compound or pharmaceutical composition to a subject for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject already suffering from a disease or condition.

The term "pharmaceutically acceptable salt" refers to salts that retain the biological effectiveness and properties of a compound and, which are not biologically or otherwise undesirable for use in a pharmaceutical. In many cases, the compounds disclosed herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable salts can also be formed using inorganic and organic bases. Inorganic bases from which salts can be derived include, for example, bases that contain sodium, potassium, lithium, ammonium, calcium, magnesium, iron, zinc, copper, manganese, aluminum, and the like; particularly preferred are the ammonium, potassium, sodium, calcium and magnesium salts. In some embodiments, treatment of the compounds disclosed herein with an inorganic base results in loss of a labile hydrogen from the compound to afford the salt form including an inorganic cation such as $Li^+$, $Na^+$, $K^+$, $Mg^{2+}$ and $Ca^{2+}$ and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

Method of Treatment

In some embodiments, plinabulin can be effective in ameliorating or treating chemotherapy or radiotherapy related neutropenia (including sever neutropenia such as FN). Patients receiving plinabulin treatment showed less bone pain, lower hospitalization frequency, and lower frequency of grade 4 neutropenia in cycle 1 when compared with other treatment method (e.g., G-CSF). In addition, plinabulin treatment also resulted in minimum or less febrile neutropenia when compared with other treatment methods (e.g., G-CSF).

In some embodiments, plinabulin can be used together with G-CSF to reduce, ameliorate, or prevent neutropenia caused by a chemotherapeutic composition. Consistent with the benefit of neutropenia prevention, patients receiving plinabulin may require less G-CSF treatment.

Patients receiving plinabulin treatment are less likely to require chemotherapeutic agent dose reduction. The safety profile of plinabulin is better than other drugs that are used to treat or ameliorate chemotherapeutic agent induced neutropenia (e.g., G-CSF treatment).

Patients receiving plinabulin treatment can show at least one of the following conditions: 1) lower incidence of Grade 4 neutropenia (absolute neutrophil count [ANC]<$0.5\times109$/L); 2) lower incidence of febrile neutropenia (FN) (ANC<$0.5\times109$/L and body temperature≥$38.3°$ C.); 3) higher neutrophil count during the treatment cycle; 4) lower incidence of documented infections in Cycles 1 to 4; 5) lower incidence and shorter duration of hospitalizations due to FN during the treatment cycle; 6) better health-related Quality of Life. When compared with the G-CSF treatment (e.g., pegfilgrastim or filgrastim), plinabulin treatment showed lower incidence of antibiotic use, lower incidence of docetaxel dose delay, dose reduction, and/or dose discontinuation, lower Incidence, occurrence, and severity of adverse events (AEs)/serious adverse events (SAEs), lower incidence, occurrence and severity of bone pain, better systemic tolerance (physical examination and safety laboratory assessments).

Some embodiments relate to a method of reducing or preventing neutropenia induced by one or more chemotherapeutic agents in the first chemotherapeutic composition, the method comprising administering plinabulin to the patient undergoing a chemotherapy treatment. In some embodiments, the neutropenia is induced by one agent in the first chemotherapeutic composition. In some embodiments, the neutropenia is induced by two or more agents in a first chemotherapeutic composition. In some embodiments, the neutropenia is induced by one or more chemotherapeutic agents present in at least one additional chemotherapeutic composition. In some embodiments, the neutropenia is induced by chemotherapeutic agents in the first chemotherapeutic composition and at least one additional chemotherapeutic composition. In some embodiments, the neutropenia is induced by the chemotherapeutic agent in the first chemotherapeutic composition and docetaxel. In some embodiments, the first chemotherapeutic composition does not comprise taxane. In some embodiments, the first chemotherapeutic composition does not comprise docetaxel.

In some embodiments, plinabulin is useful in preventing, treating, or ameliorating neutrophil reduction arising from a chemotherapy treatment.

Some embodiments relate to a method of treating a patient being administered one or more chemotherapeutic compositions in an amount sufficient to cause neutropenia, the method comprising: administering plinabulin at a dose effective to alleviate or prevent neutrophil reduction in the patient.

Some embodiments relate to using plinabulin to relieve the degree of neutropenia and to shorten the severe duration of neutropenia.

In some embodiments, the absolute neutrophil count (ANC) of the subject prior to administration of plinabulin is less than 500/mm$^3$. In some embodiments, the ANC of the subject prior to administration of plinabulin is in the range of about 500 to about 1000/mm$^3$. In some embodiments, the ANC of the subject prior to administration of plinabulin is in the range of about 1000 to about 1500/mm$^3$. In some embodiments, the ANC of the subject prior to administration of plinabulin is greater than 1500/mm$^3$.

In some embodiments, the ANC of the subject show an increase of at least 1%, 2%, 3%, 4%, 5%, 6%, 7%, 8%, 9%, 10%, 12%, 15%, 17%, 20%, 25%, 30%, 35%, 40%, 45%, 50%, 55%, 60%, 65%, 70%, 75%, 80%, 85%, 90%, 95%, 99%, 100%, 125%, 150%, or 175%, 200% post the administration of plinabulin. In some embodiments, the ANC of the subject show an increase of less than 10%, 12%, 15%, 17%, 20%, 25%, 30%, 35%, 40%, 45%, 50%, 55%, 60%, 65%, 70%, 75%, 80%, 85%, 90%, 95%, 99%, 100%, 125%, 150%, or 175%, 200% post the administration of plinabulin. In some embodiments, the ANC of the subject show an increase in the range of about 5%-40%, 10%-40%, 12.5%-40%, 5%-50%, 10%-50%, 12.5%-50%, 15%-50%, 17.5%-50%, 20%-50%, 25%-50%, 27.5%-50%, 30%-50%, 5%-60%, 10%-60%, 12.5%-60%, 15%-60%, 17.5%-60%, 20%-60%, 25%-60%, 27.5%-60%, 30%-60%, 35%-60%, 37.5%-60%, 40%-60%, 45%-70%, or 50%-80% post the administration of plinabulin.

In some embodiments, the subject has a grade 4 neutropenia induced by the chemotherapy (e.g., the first chemotherapeutic composition) or radiation therapy. In some embodiments, the subject has a grade 3 neutropenia induced by the chemotherapy (e.g., the first chemotherapeutic composition) or radiation therapy. In some embodiments, the subject has a grade 2 neutropenia induced by chemotherapy (e.g., the first chemotherapeutic composition) or radiation therapy. In some embodiments, the subject has a grade 1 neutropenia induced by chemotherapy (e.g., the first chemotherapeutic composition) or radiation therapy.

Some embodiments relate to treating chemotherapy or radiation therapy induced neutropenia in a subject having advanced or metastatic breast cancer, comprising identifying a patient having advanced or metastatic breast cancer; and administering a pharmaceutically effective amount of plinabulin.

Some embodiments relate to a method of treating chemotherapy or radiation therapy induced neutropenia in a subject having non-small cell lung cancer, comprising: identifying a patient having non-small cell lung cancer; and administering a pharmaceutically effective amount of plinabulin.

Some embodiments relate to a method of treating chemotherapy or radiation therapy induced neutropenia in a subject having hormone refractory metastatic prostate cancer, comprising: identifying a patient having hormone refractory metastatic prostate cancer; and administering a pharmaceutically effective amount of plinabulin.

In some embodiments, the neutropenia is a febrile neutropenia. In some embodiments, the neutropenia is a drug-induced neutropenia. In some embodiments, the neutropenia is a taxane-induced neutropenia. In some embodiments, the neutropenia is induced by cyclophosphamide. In some embodiments, the neutropenia is induced by cisplatin. In some embodiments, the neutropenia is induced by doxorubicin. In some embodiments, the neutropenia is induced by topotecan.

In some embodiments, the method includes administering one or more additional chemotherapeutic compositions to the subject. In some embodiments, the method includes administering a second chemotherapeutic composition. In some embodiments, the method includes administering a third chemotherapeutic composition. In some embodiments, the method includes administering a fourth chemotherapeutic composition. In some embodiments, the method includes administering a fifth chemotherapeutic composition. In some embodiments, the method includes administering a sixth chemotherapeutic composition. In some embodiments, the method includes administering a seventh chemotherapeutic composition. In some embodiments, the method includes administering an eighth chemotherapeutic composition. In various embodiments, each chemotherapeutic composition can independently comprise one or more chemotherapeutic agents. In some embodiments, one or more chemotherapeutic compositions may comprise one or more chemotherapeutic agents in common with one or more other chemotherapeutic compositions. In some embodiments, when the chemotherapeutic composition includes two or more agents, each agent in the composition can be administered separately. In some embodiments, when the chemotherapeutic composition includes two or more agents, each agent in the composition can be administered sequentially.

In some embodiments, the method described herein can include administering a second chemotherapeutic composition. In some embodiments, the second chemotherapeutic composition can be administered after the administration of plinabulin. In some embodiments, the second chemotherapeutic composition can be administered before the administration of plinabulin. In some embodiments, the second chemotherapeutic composition can be administered simultaneously with plinabulin. In some embodiments, the second chemotherapeutic composition can be administered before the first chemotherapeutic composition. In some embodiments, the second chemotherapeutic composition can be administered after the first chemotherapeutic composition. In some embodiments, the second chemotherapeutic composition can be administered simultaneously with the first chemotherapeutic composition.

In some embodiments, the method described herein can include administering a third chemotherapeutic composition. In some embodiments, the third chemotherapeutic composition can be administered prior to the administration of plinabulin. In some embodiments, the third chemotherapeutic composition can be administered after the administration of plinabulin. In some embodiments, the third chemotherapeutic composition can be administered simultaneously with plinabulin. In some embodiments, the third chemotherapeutic composition can be administered before the first chemotherapeutic composition. In some embodiments, the third chemotherapeutic composition can be administered after the first chemotherapeutic composition. In some embodiments, the third chemotherapeutic composition can be administered simultaneously with the first chemotherapeutic composition.

In some embodiments, the method described herein can include administering a fourth chemotherapeutic composition. In some embodiments, the fourth chemotherapeutic composition can be administered prior to the administration of plinabulin. In some embodiments, the fourth chemotherapeutic composition can be administered after the administration of plinabulin. In some embodiments, the fourth chemotherapeutic composition can be administered simultaneously with plinabulin. In some embodiments, the fourth chemotherapeutic composition can be administered before the first chemotherapeutic composition. In some embodiments, the fourth chemotherapeutic composition can be administered after the first chemotherapeutic composition. In some embodiments, the fourth chemotherapeutic composition can be administered simultaneously with the first chemotherapeutic composition.

In some embodiments, the method described herein can include administering a fifth chemotherapeutic composition. In some embodiments, the fifth chemotherapeutic composition can be administered prior to the administration of plinabulin. In some embodiments, the fifth chemotherapeutic composition can be administered after the administration of plinabulin. In some embodiments, the fifth chemotherapeutic composition can be administered simultaneously with plinabulin. In some embodiments, the fifth chemotherapeutic composition can be administered before the first chemotherapeutic composition. In some embodiments, the fifth chemotherapeutic composition can be administered after the first chemotherapeutic composition. In some embodiments, the fifth chemotherapeutic composition can be administered simultaneously with the first chemotherapeutic composition.

In some embodiments, the method described herein can include administering a sixth chemotherapeutic composition. In some embodiments, the sixth chemotherapeutic composition can be administered prior to the administration of plinabulin. In some embodiments, the sixth chemotherapeutic composition can be administered after the administration of plinabulin. In some embodiments, the sixth chemotherapeutic composition can be administered simultaneously with plinabulin. In some embodiments, the sixth chemotherapeutic composition can be administered before the first chemotherapeutic composition. In some embodiments, the sixth chemotherapeutic composition can be administered after the first chemotherapeutic composition. In some embodiments, the sixth chemotherapeutic composition can be administered simultaneously with the first chemotherapeutic composition.

In some embodiments, the method described herein can include administering a seventh chemotherapeutic composition. In some embodiments, the seventh chemotherapeutic composition can be administered prior to the administration of plinabulin. In some embodiments, the seventh chemotherapeutic composition can be administered after the administration of plinabulin. In some embodiments, the seventh chemotherapeutic composition can be administered simultaneously with plinabulin. In some embodiments, the seventh chemotherapeutic composition can be administered before the first chemotherapeutic composition. In some embodiments, the seventh chemotherapeutic composition can be administered after the first chemotherapeutic composition. In some embodiments, the seventh chemotherapeutic composition can be administered simultaneously with the first chemotherapeutic composition.

In some embodiments, the method described herein can include administering an eighth chemotherapeutic composition. In some embodiments, the eighth chemotherapeutic composition can be administered prior to the administration of plinabulin. In some embodiments, the eighth chemotherapeutic composition can be administered after the administration of plinabulin. In some embodiments, the eighth chemotherapeutic composition can be administered simultaneously with plinabulin. In some embodiments, the eighth chemotherapeutic composition can be administered before the first chemotherapeutic composition. In some embodiments, the eighth chemotherapeutic composition can be administered after the first chemotherapeutic composition. In some embodiments, the eighth chemotherapeutic composition can be administered simultaneously with the first chemotherapeutic composition.

In some embodiments, the method described herein can include administering plinabulin prior to administration of the first chemotherapeutic composition; and administering the additional one or more chemotherapeutic compositions after administration of the first chemotherapeutic composition. In some embodiments, the method described herein can include administering the first chemotherapeutic composition prior to administration of the plinabulin; and administering the additional one or more chemotherapeutic compositions after administration of the plinabulin. In some embodiments, the method described herein can include administering the first chemotherapeutic composition prior to administration of the additional one or more chemotherapeutic compositions; and administering the plinabulin after administration of the additional one or more chemotherapeutic agents.

In some embodiments, the method described herein can include a period of time between administration of each of plinabulin, the first chemotherapeutic composition, and the additional one or more chemotherapeutic compositions is independently selected between about 1 minute and 24 hours.

In some embodiments, the one or more additional chemotherapeutic compositions (e.g., the second, third, fourth, fifth, sixth, seventh, or eighth chemotherapeutic composition) can independently include one or more agents selected from the group consisting of methotrexate, vinblastine, doxorubicin, cisplatin, MVAC (methotrexate, vinblastine, doxorubicin and cisplatin), docetaxel, trastuzumab, cyclophosphamide, paclitaxel, dose-dense AC followed by T (i.e., doxorubicin, cyclophosphamide, paclitaxel), TAC (docetaxel, doxorubicin, cyclophosphamide), fluorouracil, bleomycin, etoposide, vincristine, procarbazine, prednisone, BEACOPP (bleomycin, etoposide, doxorubicin, cyclophosphamide, vincristine, procarbazine, prednisone), gemcitabine, ifosfamide, carboplatin, ICE (ifosfamide, carboplatin, etoposide), rituximab, RICE (rituximab, ifosfamide, carboplatin, etoposide), CHOP-14 (cyclophosphamide, doxorubicin, vincristine, prednisone), mesna, novantrone, MINE (mesna, ifosfamide, novantrone, etoposide), dexamethasone, cytarabine DHAP (dexamethasone, cisplatin, cytarabine), methylprednisolone, ESHAP (etoposide, methylprednisolone, cisplatin, cytarabine), HyperCVAD and rituximab (cyclophosphamide, vincristine, doxorubicin, dexamethasone, rituximab), dacarbazine, vinblastine, dacarbazine-based combination (dacarbazine, cisplatin, vinblastine), dacarbazine-based combination with IL-2 and interferon alfa (dacarbazine, cisplatin, vinblastine, IL-2, interferon alfa), topotecan, MAID (mesna, doxorubicin, ifosfamine, dacarbazine), VeIP (vinblastine, ifosfamide, cisplatin), VIP (etoposide, ifosfamide, cisplatin), TIP (paclitaxel, ifosfamide, cisplatin), gemcitabine, CMF classic (cyclophosphamide, methotrexate, fluorouracil), AC (doxorubicin, cyclophosphamide), FEC (fluorouracil, epirubicin, cyclophosphamide), TC (docetaxel, cyclophosphamide), cisplatin/topotecan, paclitaxel/cisplatin, irincotecan, FOLFOX (fluorouracil, leucovorin, oxaliplatin), irincotecan/cisplatin, epirubicin/cisplatin/5-fluorouracil, epirubicin/cisplatin/capecitabine, DT-PACE (dexamethasone/thalidomide/cisplatin/doxorubicin/cyclophosphamide/etoposide), ET-PACE and bortezomib, EPOCH (etoposide, prednisone, vincristine, cyclophosphamide, doxorubicin), GDP (gemcitabine, dexamethasone, cisplatin), GDP and rituximab, FMR (fludarabine, mitoxantrone, rituximab, CHOP and rituximab (cyclophosphamide, doxorubicin, vincristine, prednisone, rituximab), cisplatin/paclitaxel, cisplatin/vinorelbine, cisplatin/docetaxel, ciaplatin/etoposide, carboplatin/paclitaxel, carboplatin/docetaxel, FOLFIRINOX (5-FU/leucovorin, irinotecan and oxaliplatin), cabazitaxel, etoposide/carboplatin, etoposide/cisplatin. In some embodiments, the one or more additional chemotherapeutic compositions (e.g., the second, third, fourth, fifth, sixth, seventh, or eighth chemotherapeutic composition) can independently include one or more agents selected from the group consisting of methotrexate, vinblastine, doxorubicin, cisplatin, docetaxel, trastuzumab, cyclophosphamide, paclitaxel, fluorouracil, bleomycin, etoposide, vincristine, procarbazine, prednisone, gemcitabine, ifosfamide, carboplatin, mesna, novantrone, cytarabine methylprednisolone, rituximab dacarbazine, vinblastine, topotecan, gemcitabine, irincotecan, epirubicin, 5-fluorouracil, capecitabine, bortezomib, and cabazitaxel.

In some embodiments, the first chemotherapeutic composition can include one or more agents selected from the group consisting of methotrexate, vinblastine, doxorubicin, cisplatin, MVAC (methotrexate, vinblastine, doxorubicin and cisplatin), trastuzumab, cyclophosphamide, dose-dense AC followed by T (i.e., doxorubicin, cyclophosphamide, paclitaxel), fluorouracil, bleomycin, etoposide, vincristine, procarbazine, prednisone, BEACOPP (bleomycin, etoposide, doxorubicin, cyclophosphamide, vincristine, procarbazine, prednisone), gemcitabine, ifosfamide, carboplatin, ICE (ifosfamide, carboplatin, etoposide), rituximab, RICE (rituximab, ifosfamide, carboplatin, etoposide), CHOP-14 (cyclophosphamide, doxorubicin, vincristine, prednisone), mesna, novantrone, MINE (mesna, ifosfamide, novantrone, etoposide), dexamethasone, cytarabine DHAP (dexamethasone, cisplatin, cytarabine), methylprednisolone, ESHAP (etoposide, methylprednisolone, cisplatin, cytarabine), HyperCVAD and rituximab (cyclophosphamide, vincristine, doxorubicin, dexamethasone, rituximab), dacarbazine, vinblastine, dacarbazine-based combination (dacarbazine, cisplatin, vinblastine), dacarbazine-based combination with IL-2 and interferon alfa (dacarbazine, cisplatin, vinblastine, IL-2, interferon alfa), topotecan, MAID (mesna, doxorubicin, ifosfamine, dacarbazine), VeIP (vinblastine, ifosfamide, cisplatin), VIP (etoposide, ifosfamide, cisplatin), TIP (paclitaxel, ifosfamide, cisplatin). In some embodiments, the gemcitabine, CMF classic (cyclophosphamide, methotrexate, fluorouracil), AC (doxorubicin, cyclophosphamide), FEC (fluorouracil, epirubicin, cyclophosphamide), cisplatin/topotecan, paclitaxel/cisplatin, irincotecan, FOLFOX (fluorouracil, leucovorin, oxaliplatin), irincotecan/cisplatin, epirubicin/cisplatin/5-fluorouracil, epirubicin/cisplatin/capecitabine, DT-PACE (dexamethasone/thalidomide/cisplatin/doxorubicin/cyclophosphamide/etoposide), ET-PACE and bortezomib, EPOCH (etoposide, prednisone, vincristine, cyclophosphamide, doxorubicin), GDP (gemcitabine, dexamethasone, cisplatin), GDP and rituximab, FMR (fludarabine, mitoxantrone, rituximab, CHOP and rituximab (cyclophosphamide, doxorubicin, vincristine, prednisone, rituximab), cisplatin/paclitaxel, cisplatin/vinorelbine, ciaplatin/etoposide, carboplatin/paclitaxel, FOLFIRINOX (5-FU/leucovorin, irinotecan and oxaliplatin), cabazitaxel, etoposide/carboplatin, etoposide/cisplatin. In some embodiments, the first chemotherapeutic compositions can include one or more agents selected from the group consisting of methotrexate, vinblastine, doxorubicin, cisplatin, trastuzumab, cyclophosphamide, fluorouracil, bleomycin, etoposide, vincristine, procarbazine, prednisone, gemcitabine, ifosfamide, carboplatin, mesna, novantrone, cytarabine methylprednisolone, rituximab dacarbazine, vinblastine, topotecan, gemcitabine, irincotecan, epirubicin, 5-fluorouracil, capecitabine, and bortezomib.

Some embodiments relate to a method of stimulating neutrophil survival, comprising administering plinabulin at a dose in the range of about 1 mg/m$^2$ to about 50 mg/m$^2$. In some embodiments, the plinabulin is administered at a dose in the range of about 1-50 mg/m$^2$ of the body surface area. In some embodiments, the plinabulin is administered at a dose in the range of about 1-2, 1-3, 1-4, 1-5, 1-6, 1-7, 1-8, 1-9, 1-10, 1-11, 1-12, 1-13, 1-13.75, 1-14, 1-15, 1-16, 1-17, 1-18, 1-19, 1-20, 1-22.5, 1-25, 1-27.5, 1-30, 1.5-2, 1.5-3, 1.5-4, 1.5-5, 1.5-6, 1.5-7, 1.5-8, 1.5-9, 1.5-10, 1.5-11, 1.5-12, 1.5-13, 1.5-13.75, 1.5-14, 1.5-15, 1.5-16, 1.5-17, 1.5-18, 1.5-19, 1.5-20, 1.5-22.5, 1.5-25, 1.5-27.5, 1.5-30, 2.5-2, 2.5-3, 2.5-4, 2.5-5, 2.5-6, 2.5-7, 2.5-8, 2.5-9, 2.5-10, 2.5-11, 2.5-12, 2.5-13, 2.5-13.75, 2.5-14, 2.5-15, 2.5-16, 2.5-17, 2.5-18, 2.5-19, 2.5-20, 2.5-22.5, 2.5-25, 2.5-27.5, 2.5-30, 2.5-7.5, 3-4, 3-5, 3-6, 3-7, 3-8, 3-9, 3-10, 3-11, 3-12, 3-13, 3-13.75, 3-14, 3-15, 3-16, 3-17, 3-18, 3-19, 3-20, 3-22.5, 3-25, 3-27.5, 3-30, 3.5-6.5, 3.5-13.75, 3.5-15, 2.5-17.5, 4-5, 4-6, 4-7, 4-8, 4-9, 4-10, 4-11, 4-12, 4-13, 4-13.75, 4-14, 4-15, 4-16, 4-17, 4-18, 4-19, 4-20, 4-22.5, 4-25, 4-27.5, 4-30, 5-6, 5-7, 5-8, 5-9, 5-10, 5-11, 5-12, 5-13, 5-13.75, 5-14, 5-15, 5-16, 5-17, 5-18, 5-19, 5-20, 5-22.5, 5-25, 5-27.5, 5-30, 6-7, 6-8, 6-9, 6-10, 6-11, 6-12, 6-13, 6-13.75, 6-14, 6-15, 6-16, 6-17, 6-18, 6-19, 6-20, 6-22.5, 6-25, 6-27.5, 6-30, 7-8, 7-9, 7-10, 7-11, 7-12, 7-13, 7-13.75, 7-14, 7-15, 7-16, 7-17, 7-18, 7-19, 7-20, 7-22.5, 7-25, 7-27.5, 7-30, 7.5-12.5, 7.5-13.5, 7.5-15, 8-9, 8-10, 8-11, 8-12, 8-13, 8-13.75, 8-14, 8-15, 8-16, 8-17, 8-18, 8-19, 8-20, 8-22.5, 8-25, 8-27.5, 8-30, 9-10, 9-11, 9-12, 9-13, 9-13.75, 9-14, 9-15, 9-16, 9-17, 9-18, 9-19, 9-20, 9-22.5, 9-25, 9-27.5, 9-30, 10-11, 10-12, 10-13, 10-13.75, 10-14, 10-15, 10-16, 10-17, 10-18, 10-19, 10-20, 10-22.5, 10-25, 10-27.5, 10-30, 11.5-15.5, 12.5-14.5, 7.5-22.5, 8.5-32.5, 9.5-15.5, 15.5-24.5, 5-35, 17.5-22.5, 22.5-32.5, 25-35, 25.5-24.5, 27.5-32.5, 2-20, t 2.5-22.5, or 9.5-21.5 mg/m$^2$, of the body surface area.

In some embodiments, the plinabulin is administered at a dose of about 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 32, 33, 34, 35, 36, 37, 38, 39, 40 mg/m$^2$ of the body surface area. In some embodiments, the plinabulin is administered at a dose less than about 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 32, 33, 34, 35, 36, 37, 38, 39, 40 mg/m$^2$ of the body surface area. In some embodiments, the plinabulin is administered at a dose greater than about 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 32, 33, 34, 35, 36, 37, 38, 39, 40, 41, 42, 43, 44, 45, 46, 47, 48, 49, 50 mg/m$^2$ of the body surface area.

In some embodiments, the plinabulin dose is about 5 mg-300 mg, 5 mg-200 mg, 7.5 mg-200 mg, 10 mg-100 mg, 15 mg-100 mg, 20 mg-100 mg, 30 mg-100 mg, 40 mg-100 mg, 10 mg-80 mg, 15 mg-80 mg, 20 mg-80 mg, 30 mg-80 mg, 40 mg-80 mg, 10 mg-60 mg, 15 mg-60 mg, 20 mg-60 mg, 30 mg-60 mg, or about 40 mg-60 mg. In some embodiments, the plinabulin administered is about 20 mg-60 mg, 27 mg-60 mg, 20 mg-45 mg, or 27 mg-45 mg. In some embodiments, the plinabulin administered is about 5 mg-7.5 mg, 5 mg-9 mg, 5 mg-10 mg, 5 mg-12 mg, 5 mg-14 mg, 5 mg-15 mg, 5 mg-16 mg, 5 mg-18 mg, 5 mg-20 mg, 5 mg-22 mg, 5 mg-24 mg, 5 mg-26 mg, 5 mg-28 mg, 5 mg-30 mg, 5 mg-32 mg, 5 mg-34 mg, 5 mg-36 mg, 5 mg-38 mg, 5 mg-40 mg, 5 mg-42 mg, 5 mg-44 mg, 5 mg-46 mg, 5 mg-48 mg, 5 mg-50 mg, 5 mg-52 mg, 5 mg-54 mg, 5 mg-56 mg, 5 mg-58 mg, 5 mg-60 mg, 7 mg-7.7 mg, 7 mg-9 mg, 7 mg-10 mg, 7 mg-12 mg, 7 mg-14 mg, 7 mg-15 mg, 7 mg-16 mg, 7 mg-18 mg, 7 mg-20 mg, 7 mg-22 mg, 7 mg-24 mg, 7 mg-26 mg, 7 mg-28 mg, 7 mg-30 mg, 7 mg-32 mg, 7 mg-34 mg, 7 mg-36 mg, 7 mg-38 mg, 7 mg-40 mg, 7 mg-42 mg, 7 mg-44 mg, 7 mg-46 mg, 7 mg-48 mg, 7 mg-50 mg, 7 mg-52 mg, 7 mg-54 mg, 7 mg-56 mg, 7 mg-58 mg, 7 mg-60 mg, 9 mg-10 mg, 9 mg-12 mg, 9 mg-14 mg, 9 mg-15 mg, 9 mg-16 mg, 9 mg-18 mg, 9 mg-20 mg, 9 mg-22 mg, 9 mg-24 mg, 9 mg-26 mg, 9 mg-28 mg, 9 mg-30 mg, 9 mg-32 mg, 9 mg-34 mg, 9 mg-36 mg, 9 mg-38 mg, 9 mg-40 mg, 9 mg-42 mg, 9 mg-44 mg, 9 mg-46 mg, 9 mg-48 mg, 9 mg-50 mg, 9 mg-52 mg, 9 mg-54 mg, 9 mg-56 mg, 9 mg-58 mg, 9 mg-60 mg, 10 mg-12 mg, 10 mg-14 mg, 10 mg-15 mg, 10 mg-16 mg, 10 mg-18 mg, 10 mg-20 mg, 10 mg-22 mg, 10 mg-24 mg, 10 mg-26 mg, 10 mg-28 mg, 10 mg-30 mg, 10 mg-32 mg, 10 mg-34 mg, 10 mg-36 mg, 10 mg-38 mg, 10 mg-40 mg, 10 mg-42 mg, 10 mg-44 mg, 10 mg-46 mg, 10 mg-48 mg, 10 mg-50 mg, 10 mg-52 mg, 10 mg-54 mg, 10 mg-56 mg, 10 mg-58 mg, 10 mg-60 mg, 12 mg-14 mg, 12 mg-15 mg, 12 mg-16 mg, 12 mg-18 mg, 12 mg-20 mg, 12 mg-22 mg, 12 mg-24 mg, 12 mg-26 mg, 12 mg-28 mg, 12 mg-30 mg, 12 mg-32 mg, 12 mg-34 mg, 12 mg-36 mg, 12 mg-38 mg, 12 mg-40 mg, 12 mg-42 mg, 12 mg-44 mg, 12 mg-46 mg, 12 mg-48 mg, 12 mg-50 mg, 12 mg-52 mg, 12 mg-54 mg, 12 mg-56 mg, 12 mg-58 mg, 12 mg-60 mg, 15 mg-16 mg, 15 mg-18 mg, 15 mg-20 mg, 15 mg-22 mg, 15 mg-24 mg, 15 mg-26 mg, 15 mg-28 mg, 15 mg-30 mg, 15 mg-32 mg, 15 mg-34 mg, 15 mg-36 mg, 15 mg-38 mg, 15 mg-40 mg, 15 mg-42 mg, 15 mg-44 mg, 15 mg-46 mg, 15 mg-48 mg, 15 mg-50 mg, 15 mg-52 mg, 15 mg-54 mg, 15 mg-56 mg, 15 mg-58 mg, 15 mg-60 mg, 17 mg-18 mg, 17 mg-20 mg, 17 mg-22 mg, 17 mg-24 mg, 17 mg-26 mg, 17 mg-28 mg, 17 mg-30 mg, 17 mg-32 mg, 17 mg-34 mg, 17 mg-36 mg, 17 mg-38 mg, 17 mg-40 mg, 17 mg-42 mg, 17 mg-44 mg, 17 mg-46 mg, 17 mg-48 mg, 17 mg-50 mg, 17 mg-52 mg, 17 mg-54 mg, 17 mg-56 mg, 17 mg-58 mg, 17 mg-60 mg, 20 mg-22 mg, 20 mg-24 mg, 20 mg-26 mg, 20 mg-28 mg, 20 mg-30 mg, 20 mg-32 mg, 20 mg-34 mg, 20 mg-36 mg, 20 mg-38 mg, 20 mg-40 mg, 20 mg-42 mg, 20 mg-44 mg, 20 mg-46 mg, 20 mg-48 mg, 20 mg-50 mg, 20 mg-52 mg, 20 mg-54 mg, 20 mg-56 mg, 20 mg-58 mg, 20 mg-60 mg, 22 mg-24 mg, 22 mg-26 mg, 22 mg-28 mg, 22 mg-30 mg, 22 mg-32 mg, 22 mg-34 mg, 22 mg-36 mg, 22 mg-38 mg, 22 mg-40 mg, 22 mg-42 mg, 22 mg-44 mg, 22 mg-46 mg, 22 mg-48 mg, 22 mg-50 mg, 22 mg-52 mg, 22 mg-54 mg, 22 mg-56 mg, 22 mg-58 mg, 22 mg-60 mg, 25 mg-26 mg, 25 mg-28 mg, 25 mg-30 mg, 25 mg-32 mg, 25 mg-34 mg, 25 mg-36 mg, 25 mg-38 mg, 25 mg-40 mg, 25 mg-42 mg, 25 mg-44 mg, 25 mg-46 mg, 25 mg-48 mg, 25 mg-50 mg, 25 mg-52 mg, 25 mg-54 mg, 25 mg-56 mg, 25 mg-58 mg, 25 mg-60 mg, 27 mg-28 mg, 27 mg-30 mg, 27 mg-32 mg, 27 mg-34 mg, 27 mg-36 mg, 27 mg-38 mg, 27 mg-40 mg, 27 mg-42 mg, 27 mg-44 mg, 27 mg-46 mg, 27 mg-48 mg, 27 mg-50 mg, 27 mg-52 mg, 27 mg-54 mg, 27 mg-56 mg, 27 mg-58 mg, 27 mg-60 mg, 30 mg-32 mg, 30 mg-34 mg, 30 mg-36 mg, 30 mg-38 mg, 30 mg-40 mg, 30 mg-42 mg, 30 mg-44 mg, 30 mg-46 mg, 30 mg-48 mg, 30 mg-50 mg, 30 mg-52 mg, 30 mg-54 mg, 30 mg-56 mg, 30 mg-58 mg, 30 mg-60 mg, 33 mg-34 mg, 33 mg-36 mg, 33 mg-38 mg, 33 mg-40 mg, 33 mg-42 mg, 33 mg-44 mg, 33 mg-46 mg, 33 mg-48 mg, 33 mg-50 mg, 33 mg-52 mg, 33 mg-54 mg, 33 mg-56 mg, 33 mg-58 mg, 33 mg-60 mg, 36 mg-38 mg, 36 mg-40 mg, 36 mg-42 mg, 36 mg-44 mg, 36 mg-46 mg, 36 mg-48 mg, 36 mg-50 mg, 36 mg-52 mg, 36 mg-54 mg, 36 mg-56 mg, 36 mg-58 mg, 36 mg-60 mg, 40 mg-42 mg, 40 mg-44 mg, 40 mg-46 mg, 40 mg-48 mg, 40 mg-50 mg, 40 mg-52 mg, 40 mg-54 mg, 40 mg-56 mg, 40 mg-58 mg, 40 mg-60 mg, 43 mg-46 mg, 43 mg-48 mg, 43 mg-50 mg, 43 mg-52 mg, 43 mg-54 mg, 43 mg-56 mg, 43 mg-58 mg, 42 mg-60 mg, 45 mg-48 mg, 45 mg-50 mg, 45 mg-52 mg, 45 mg-54 mg, 45 mg-56 mg, 45 mg-58 mg, 45 mg-60 mg, 48 mg-50 mg, 48 mg-52 mg, 48 mg-54 mg, 48 mg-56 mg, 48 mg-58 mg, 48 mg-60 mg, 50 mg-52 mg, 50 mg-54 mg, 50 mg-56 mg, 50 mg-58 mg, 50 mg-60 mg, 52 mg-54 mg, 52 mg-56 mg, 52 mg-58 mg, or 52 mg-60 mg. In some embodiments, the plinabulin dose is greater than about 5 mg, about 10 mg, about 12.5 mg, about 13.5 mg, about 15 mg, about 17.5 mg, about 20 mg, about 22.5 mg, about 25 mg, about 27 mg, about 30 mg, about 40 mg, about 50 mg, about 60 mg, about 70 mg, about 80 mg, about 90 mg, about 100 mg, about 125 mg, about 150 mg, or about 200 mg. In some embodiments, the plinabulin dose is about less than about 5 mg, about 10 mg, about 12.5 mg, about 13.5 mg, about 15 mg, about 17.5 mg, about 20 mg, about 22.5 mg, about 25 mg, about 27 mg, about 30 mg, about 40 mg, about 50 mg, about 60 mg, about 70 mg, about 80 mg, about 90 mg, about 100 mg, about 125 mg, about 150 mg, or about 200 mg.

The chemotherapeutic composition or chemotherapeutic agent can be administered in an effective amount suitable for the treatment. In some embodiments, the method described herein comprises administering one or more chemotherapeutic agents (e.g., cisplatin, doxorubicin, cyclophosphamide, topotecan) at a dose in the range of about 40-50 mg/kg in divided doses over 2-5 days. In some embodiments, the method described herein comprises administering one or more chemotherapeutic agents at a dose in the range of about 10-30, 5-100, 10-200, 10-100, 10-90, 10-80, 10-70, 10-60, 10-50, 10-40, 10-30, 10-20, 20-200, 20-100, 20-90, 20-80, 20-70, 20-60, 20-50, 20-40, 20-30, 30-200, 30-100, 30-90, 30-80, 30-70, 30-60, 30-50, 30-40, 40-200, 40-100, 40-90, 40-80, 40-70, 40-60, 40-50, 50-300, 50-200, 50-100, 50-90, 50-80, 50-70, 50-60, 60-300, 60-200, 60-100, 60-90, 60-80, 60-70, 70-300, 70-200, 70-100, 70-90, 70-80, 80-300, 80-200, 80-100, 80-90, or 90-300, 90-200, 90-100, 100-500, 100-400, 100-300, or 100-200 mg/kg over 2-5 days per cycle. In some embodiments, the method described herein comprises administering one or more chemotherapeutic agents at a dose in the range of about 10-15 mg/kg in divided doses over 7-10 days or 3-5 mg/kg twice weekly. In some embodiments, the method described herein comprises administering one or more chemotherapeutic agents at a dose in the range of about 10-30, 5-100, 10-200, 10-100, 10-90, 10-80, 10-70, 10-60, 10-50, 10-40, 10-30, 10-20, 20-200, 20-100, 20-90, 20-80, 20-70, 20-60, 20-50, 20-40, 20-30, 30-200, 30-100, 30-90, 30-80, 30-70, 30-60, 30-50, 30-40, 40-200, 40-100, 40-90, 40-80, 40-70, 40-60, 40-50, 50-300, 50-200, 50-100, 50-90, 50-80, 50-70, 50-60, 60-300, 60-200, 60-100, 60-90, 60-80, 60-70, 70-300, 70-200, 70-100, 70-90, 70-80, 80-300, 80-200, 80-100, 80-90, or 90-300, 90-200, 90-100, 100-500, 100-400, 100-300, or 100-200 mg/kg twice weekly. In some embodiments, the method described herein comprises administering one or more chemotherapeutic agents at a dose in the range of about 1-5 mg/kg per day for both initial dose and maintenance dose.

In some embodiments, the method further comprises administering one or more chemotherapeutic agents (e.g., cisplatin, doxorubicin, cyclophosphamide, topotecan) at a dose in the range of about 10-30, 5-100, 10-200, 10-100, 10-90, 10-80, 10-70, 10-60, 10-50, 10-40, 10-30, 10-20, 20-200, 20-100, 20-90, 20-80, 20-70, 20-60, 20-50, 20-40, 20-30, 30-200, 30-100, 30-90, 30-80, 30-70, 30-60, 30-50, 30-40, 40-200, 40-100, 40-90, 40-80, 40-70, 40-60, 40-50, 50-300, 50-200, 50-100, 50-90, 50-80, 50-70, 50-60, 60-300, 60-200, 60-100, 60-90, 60-80, 60-70, 70-300, 70-200, 70-100, 70-90, 70-80, 80-300, 80-200, 80-100, 80-90, or 90-300, 90-200, 90-100, 100-500, 100-400, 100-300, or 100-200 mg/m² daily for 5 days per cycle. In some embodiments, the method further comprises administering one or more chemotherapeutic agents at a dose of 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 350, 400, 450, 500, 550, 600, 650, 700, 750, 800, 850, 900 or 1000 mg/m$^2$ per cycle once every 4 weeks. In some embodiments, the method further comprises administering one or more chemotherapeutic agents at a dose of 10-30, 5-100, 10-200, 10-100, 10-90, 10-80, 10-70, 10-60, 10-50, 10-40, 10-30, 10-20, 20-200, 20-100, 20-90, 20-80, 20-70, 20-60, 20-50, 20-40, 20-30, 30-200, 30-100, 30-90, 30-80, 30-70, 30-60, 30-50, 30-40, 40-200, 40-100, 40-90, 40-80, 40-70, 40-60, 40-50, 50-300, 50-200, 50-100, 50-90, 50-80, 50-70, 50-60, 60-300, 60-200, 60-100, 60-90, 60-80, 60-70, 70-300, 70-200, 70-100, 70-90, 70-80, 80-300, 80-200, 80-100, 80-90, or 90-300, 90-200, 90-100, 100-500, 100-400, 100-300, or 100-200 mg/m$^2$ per cycle once every 3 to 4 weeks depending on the extent of prior exposure to radiation therapy and/or prior chemotherapy. In some embodiments, the method further comprises administering one or more chemotherapeutic agents at a dose of 50 mg/m$^2$ per cycle repeated every 4 weeks. In some embodiments, the method further comprises administering one or more chemotherapeutic agents (e.g., cisplatin) at a dose in the range of about 10-30, 5-100, 10-200, 10-100, 10-90, 10-80, 10-70, 10-60, 10-50, 10-40, 10-30, 10-20, 20-200, 20-100, 20-90, 20-80, 20-70, 20-60, 20-50, 20-40, 20-30, 30-200, 30-100, 30-90, 30-80, 30-70, 30-60, 30-50, 30-40, 40-200, 40-100, 40-90, 40-80, 40-70, 40-60, 40-50, 50-300, 50-200, 50-100, 50-90, 50-80, 50-70, 50-60, 60-300, 60-200, 60-100, 60-90, 60-80, 60-70, 70-300, 70-200, 70-100, 70-90, 70-80, 80-300, 80-200, 80-100, 80-90, or 90-300, 90-200, 90-100, 100-500, 100-400, 100-300, or 100-200 mg/m$^2$ per cycle every 3 weeks or every 4 weeks. In some embodiments, the method further comprises administering one or more chemotherapeutic agents at a dose of 30-70 or 40-60 mg/m$^2$ per cycle once every 3 weeks or every 4 weeks. In some embodiments, when more than one chemotherapeutic agent is administered to the patient, the dose of each of the chemotherapeutic agent administered can be independently selected from any one of the dose ranges described herein.

In some embodiments, one or more chemotherapeutic agents are administered at an amount of about 10-30, 5-100, 10-500, 10-400, 10-300, 10-200, 10-100, 10-90, 10-80, 10-70, 10-60, 10-50, 10-40, 10-30, 10-20, 20-500, 20-400, 20-300, 20-200, 20-100, 20-90, 20-80, 20-70, 20-60, 20-50, 20-40, 20-30, 30-500, 30-400, 30-300, 30-200, 30-100, 30-90, 30-80, 30-70, 30-60, 30-50, 30-40, 40-500, 40-400, 40-300, 40-200, 40-100, 40-90, 40-80, 40-70, 40-60, 40-50, 50-500, 50-400, 50-300, 50-200, 50-100, 50-90, 50-80, 50-70, 50-60, 60-500, 60-400, 60-300, 60-200, 60-100, 60-90, 60-80, 60-70, 70-500, 70-400, 70-300, 70-200, 70-100, 70-90, 70-80, 80-500, 80-400, 80-300, 80-200, 80-100, 80-90, 90-500, 90-400, 90-300, 90-200, 90-100, 100-500, 100-400, 100-300, or 100-200 mg per dose.

In some embodiments, the plinabulin is administered prior to the administration of the chemotherapeutic agent or chemotherapeutic composition. In some embodiments, the plinabulin is administered concurrently with the chemotherapeutic agent or chemotherapeutic composition. In some embodiments, the plinabulin is administered after the chemotherapeutic agent is administered or chemotherapeutic composition.

In some embodiments, the plinabulin is administered about 1 min, 5 min, 10 min, 15 min, 20 min, 25 min, 30 min, 1 h, 1.5 h, 2 h, 2.5 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 24 h, 30 h, 36 h, 40 h, or 48 h after the administration of a chemotherapeutic agent or chemotherapeutic composition. In some embodiments, the plinabulin is administered in less than about 1 min, 5 min, 10 min, 15 min, 20 min, 25 min, 30 min, 1 h, 1.5 h, 2 h, 2.5 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, 30 h, 36 h, 40 h, or 48 h after the administration of a chemotherapeutic agent or chemotherapeutic composition. In some embodiments, the plinabulin is administered in more than about 1 min, 5 min, 10 min, 15 min, 20 min, 25 min, 30 min, 1 h, 1.5 h, 2 h, 2.5 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, 30 h, 36 h, 40 h, or 48 h after the administration of a chemotherapeutic agent or chemotherapeutic composition. In some embodiments, the plinabulin is administered in about 1 min-5 min, 1 min-10 min, 1 min-15 min, 1 min-20 min, 1 min-25 min, 1 min-30 min, 0.25 h-0.5 h, 0.25-0.75 h, 0.25-1 h, 0.5 h-1 h, 0.5 h-2 h, 0.5 h-2.5 h, 1 h-2 h, 1 h-3 h, 1 h-5 h, 1 h-24 h, 1 min-24 h, or 1 min-2 h, 1 day-2 days, 1 day-3 days, 1 day-4 days, 1 day-5 days, or 1 day-6 days after the administration of a chemotherapeutic agent or chemotherapeutic composition.

In some embodiments, when plinabulin is administered prior to a chemotherapeutic agent or chemotherapeutic composition administration, the plinabulin is administered about 1 min-5 min, 1 min-10 min, 1 min-15 min, 1 min-20 min, 1 min-25 min, 1 min-30 min, 0.25 h-0.5 h, 0.25-0.75 h, 0.25-1 h, 0.5 h-1 h, 0.5 h-2 h, 0.5 h-2.5 h, 1 h-2 h, 1 h-3 h, 1 h-5 h, 1 h-24 h, 1 min-1 h, 1 min-2 h, 1 min-5 h, 1 min-24 h, 1 day-2 days, 1 day-3 days, 1 day-4 days, 1 day-5 days, or 1 day-6 days before the administration of a chemotherapeutic agent or chemotherapeutic composition. In some embodiments, the plinabulin is administered about 1 min, 5 min, 10 min, 15 min, 20 min, 25 min, 30 min, 1 h, 1.5 h, 2 h, 2.5 h, 3 h, 4 h, 5 h, 6 h, 7 h, 8 h, 9 h, 10 h, 11 h, 12 h, 30 h, 36 h, 40 h, 48 h, 4 days, 5 days, 6 days, or 7 days before the administration of a chemotherapeutic agent or chemotherapeutic composition. In some embodiments, the plinabulin is administered in less than about 1 min, 5 min, 10 min, 15 min, 20 min, 25 min, 30 min, 1 h, 1.5 h, 2 h, 2.5 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, 30 h, 36 h, 40 h, 48 h, 4 days, 5 days, 6 days, or 7 days before the administration of a chemotherapeutic agent or chemotherapeutic composition. In some embodiments, the plinabulin is administered in more than about 1 min, 5 min, 10 min, 15 min, 20 min, 25 min, 30 min, 1 h, 1.5 h, 2 h, 2.5 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, 30 h, 36 h, 40 h, 48 h, 3 days, 4 days, 5 days, 6 days, or 7 days before the administration of a chemotherapeutic agent or chemotherapeutic composition.

In some embodiments, the treatment schedule includes co-administration of a chemotherapeutic agent or chemotherapeutic composition and plinabulin once every 3 weeks. In some embodiments, the treatment schedule includes co-administration of a chemotherapeutic agent or chemotherapeutic composition and plinabulin once every 1 week, 2 weeks, 3 weeks, 4 weeks, 5 weeks, 6 weeks, 7 weeks, or 8 weeks. In some embodiments, the treatment schedule includes co-administration of a chemotherapeutic agent or chemotherapeutic composition and plinabulin two times every 1 week, 2 weeks, 3 weeks, 4 weeks, 5 weeks, 6 weeks, 7 weeks, or 8 weeks. In some embodiments, the treatment schedule includes co-administration of a chemotherapeutic agent or chemotherapeutic composition and plinabulin once every 1 week in a treatment cycle of 1 week, 2 weeks, 3 weeks, 4 weeks, 5 weeks, 6 weeks, 7 weeks, or 8 weeks. In some embodiments, the treatment schedule includes co-administration of a chemotherapeutic agent or chemotherapeutic composition and plinabulin twice every 1 week in a treatment cycle of 1 week, 2 weeks, 3 weeks, 4 weeks, 5 weeks, 6 weeks, 7 weeks, or 8 weeks. In some embodiments, the treatment schedule includes co-administration of a chemotherapeutic agent or chemotherapeutic composition and plinabulin on day 1, day 8, and day 15 of a 21-day treatment cycle. In some embodiments, co-administration of a chemotherapeutic agent or chemotherapeutic composition and plinabulin includes administering the chemotherapeutic agent prior to administering plinabulin. In some embodiments, co-administration of a chemotherapeutic agent or chemotherapeutic composition and plinabulin includes administering the chemotherapeutic agent after administering plinabulin. In some embodiments, co-administration of a chemotherapeutic agent or chemotherapeutic composition and plinabulin includes administering the chemotherapeutic agent concurrently with plinabulin. The chemotherapeutic composition described in this paragraph can independently be a first, second, third, fourth, fifth, sixth, seventh, or eighth chemotherapeutic composition. In some embodiments, the treatment schedule includes co-administration of a chemotherapeutic agent or chemotherapeutic composition and plinabulin every day of the week for a week. In some embodiments, the treatment schedule includes co-administration of a chemotherapeutic agent or chemotherapeutic composition and plinabulin every day of the week for 2 weeks, 3 weeks, or 4 weeks. In some embodiments, the treatment schedule includes co-administration of a chemotherapeutic agent or chemotherapeutic composition and plinabulin on day 1 in weekly treatment. In some embodiments, the treatment schedule includes co-administration of a chemotherapeutic agent or chemotherapeutic composition and plinabulin on day 1 and day 2 in weekly treatment. In some embodiments, the treatment schedule includes co-administration of the chemotherapeutic agent or chemotherapeutic composition and plinabulin on day 1, day 2, and day 3 in weekly treatment. In some embodiments, the treatment schedule includes co-administration of the chemotherapeutic agent or chemotherapeutic composition and plinabulin on day 1, day 2, day 3 in weekly treatment. In some embodiments, the treatment schedule includes co-administration of the chemotherapeutic agent or chemotherapeutic composition and plinabulin on day 1, day 2, day 3, and day 4 in weekly treatment. In some embodiments, the treatment schedule includes co-administration of the chemotherapeutic agent or chemotherapeutic composition and plinabulin on day 1, day 2, day 3, day 4, and day 5 in weekly treatment. In some embodiments, the treatment schedule includes co-administration of the chemotherapeutic agent or chemotherapeutic composition and plinabulin on day 1, day 2, day 3, day 4, day 5, and day 6 in weekly treatment. In some embodiments, the treatment schedule includes co-administration of a chemotherapeutic agent or chemotherapeutic composition and plinabulin on day 1, day 3, and day 5 in weekly treatment. In some embodiments, the chemotherapeutic composition used on each administration day can be the same or different. In some embodiments, the chemotherapeutic composition used on the first administration day is different from the chemotherapeutic composition used on the rest of the administration days. In some embodiments, the chemotherapeutic composition used on the first administration day is the same as or different from the chemotherapeutic composition used on the second administration day. In some embodiments, the chemotherapeutic composition used on the first administration day is the same as or different from the chemotherapeutic composition used on the third administration day. In some embodiments, the chemotherapeutic composition used on the first administration day is the same as or different from the chemotherapeutic composition used on the fourth administration day. In some embodiments, the chemotherapeutic composition used on the first administration day is the same as or different from the chemotherapeutic composition used on the fifth administration day. In some embodiments, the chemotherapeutic composition used on the first administration day is the same as or different from the chemotherapeutic composition used on the sixth administration day. In some embodiments, the chemotherapeutic composition used on the first administration day is the same as or different from the chemotherapeutic composition used on the seventh administration day.

In some embodiments, the treatment schedule includes administration of a chemotherapeutic agent or chemotherapeutic composition (e.g., the first, the second, the third, the fourth, the fifth, the sixth, the seventh, or the eighth) once every 3 weeks. In some embodiments, the treatment schedule includes administration of a chemotherapeutic agent or chemotherapeutic composition once every 1 week, 2 weeks, 3 weeks, 4 weeks, 5 weeks, 6 weeks, 7 weeks, or 8 weeks. In some embodiments, the treatment schedule includes administration of a chemotherapeutic agent or chemotherapeutic composition two times every 1 week, 2 weeks, 3 weeks, 4 weeks, 5 weeks, 6 weeks, 7 weeks, or 8 weeks. In some embodiments, the treatment schedule includes administration of a chemotherapeutic agent or chemotherapeutic composition once every 1 week in a treatment cycle of 1 week, 2 weeks, 3 weeks, 4 weeks, 5 weeks, 6 weeks, 7 weeks, or 8 weeks. In some embodiments, the treatment schedule includes administration of a chemotherapeutic agent or chemotherapeutic composition twice every 1 week in a treatment cycle of 1 week, 2 weeks, 3 weeks, 4 weeks, 5 weeks, 6 weeks, 7 weeks, or 8 weeks. In some embodiments, the treatment schedule includes administration of a chemotherapeutic agent or chemotherapeutic composition three times (e.g., day 1, 2, 3, or day 1, 3, 5) every week in a treatment cycle of 1 week, 2 weeks, 3 weeks, 4 weeks, 5 weeks, 6 weeks, 7 weeks, or 8 weeks. In some embodiments, the treatment schedule includes administration of a chemotherapeutic agent or chemotherapeutic composition day 1, day 8, and day 15 of a 21-day treatment cycle. The chemotherapeutic composition described in this paragraph can independently be the first, second, third, fourth, fifth, sixth, seventh, or eighth chemotherapeutic composition. In some embodiments, the treatment schedule includes administration of a chemotherapeutic agent or chemotherapeutic composition every day of the week for a week. In some embodiments, the treatment schedule includes administration of a chemotherapeutic agent or chemotherapeutic composition every day of the week for 2 weeks, 3 weeks, or 4 weeks. In some embodiments, the treatment schedule includes administration of a chemotherapeutic agent or chemotherapeutic composition on day 1 in weekly treatment. In some embodiments, the treatment schedule includes administration of a chemotherapeutic agent or chemotherapeutic composition on day 1 and day 2 in weekly treatment. In some embodiments the treatment schedule includes administration of a chemotherapeutic agent or chemotherapeutic composition on day 1, day 2, and day 3 in weekly treatment. In some embodiments, the treatment schedule includes administration of a chemotherapeutic agent or chemotherapeutic composition on day 1, day 3, day 5 in weekly treatment. In some embodiments, the treatment schedule includes administration of a chemotherapeutic agent or chemotherapeutic composition on day 1, day 2, day 3, and day 4 in weekly treatment. In some embodiments, the treatment schedule includes administration of a chemotherapeutic agent or chemotherapeutic composition on day 1, day 2, day 3, day 4, and day 5 in weekly treatment. the treatment schedule includes administration of a chemotherapeutic agent or chemotherapeutic composition on day 1, day 2, day 3, day 4, day 5, and day 6 in weekly treatment.

In some embodiments, the treatment schedule includes administration of plinabulin once every 3 weeks. In some embodiments, the treatment schedule includes administration of plinabulin once every 1 week, 2 weeks, 3 weeks, 4 weeks, 5 weeks, 6 weeks, 7 weeks, or 8 weeks. In some embodiments, the treatment schedule includes administration of plinabulin two times every 1 week, 2 weeks, 3 weeks, 4 weeks, 5 weeks, 6 weeks, 7 weeks, or 8 weeks. In some embodiments, the treatment schedule includes administration of plinabulin once every 1 week in a treatment cycle of 1 week, 2 weeks, 3 weeks, 4 weeks, 5 weeks, 6 weeks, 7 weeks, or 8 weeks. In some embodiments, the treatment schedule includes administration of plinabulin twice every 1 week in a treatment cycle of 1 week, 2 weeks, 3 weeks, 4 weeks, 5 weeks, 6 weeks, 7 weeks, or 8 weeks. In some embodiments, the treatment schedule includes administration of plinabulin three times (e.g., day 1, 2, 3, or day 1, 3, 5) every 1 week in a treatment cycle of 1 week, 2 weeks, 3 weeks, 4 weeks, 5 weeks, 6 weeks, 7 weeks, or 8 weeks. In some embodiments, the treatment schedule includes administration of plinabulin day 1, day 8, and day 15 of a 21-day treatment cycle. The chemotherapeutic composition described in this paragraph can independently be the first, second, third, fourth, fifth, sixth, seventh, or eighth chemotherapeutic composition. In some embodiments, the treatment schedule includes administration of plinabulin every day of the week for a week. In some embodiments, the treatment schedule includes administration of plinabulin every day of the week for 2 weeks, 3 weeks, or 4 weeks. In some embodiments, the treatment schedule includes administration of plinabulin on day 1 in weekly treatment. In some embodiments, the treatment schedule includes administration of plinabulin on day 1 and day 2 in weekly treatment. In some embodiments the treatment schedule includes administration of plinabulin on day 1, day 2, and day 3 in weekly treatment. In some embodiments, the treatment schedule includes administration of plinabulin on day 1, day 3, day 5 in weekly treatment. In some embodiments, the treatment schedule includes administration of plinabulin on day 1, day 2, day 3, and day 4 in weekly treatment. In some embodiments, the treatment schedule includes administration of plinabulin on day 1, day 2, day 3, day 4, and day 5 in weekly treatment. the treatment schedule includes administration of plinabulin on day 1, day 2, day 3, day 4, day 5, and day 6 in weekly treatment.

The treatment cycle can be repeated as long as the regimen is clinically tolerated. In some embodiments, the treatment cycle for the chemotherapeutic agent and plinabulin is repeated for n times, wherein n is an integer in the range of 2 to 30. In some embodiments, n is 2, 3, 4, 5, 6, 7, 8, 9, or 10. In some embodiments, a new treatment cycle can occur immediately after the completion of the previous treatment cycle. In some embodiments, a new treatment cycle can occur a period of time after the completion of the previous treatment cycle. In some embodiments, a new treatment cycle can occur after 1 week, 2 weeks, 3 weeks, 4 weeks, 5 weeks, 6 weeks, or 7 weeks after the completion of the previous treatment cycle.

In some embodiments, the use of plinabulin can reduce the incidence of Grade 1 or 2 neutropenia by at least about 5%, 10%, 12.5%, 15%, 17.5%, 20%, 22.5%, 25%, 27.5%, 30%, 32.5%, 35%, 37.5%, 40%, 42.5%, 45%, 47.5%, 50%, 52.5%, 55%, 57.5%, 60%, 62.5%, 65%, 67.5%, 70%, 72.5%, 75%, 77.5%, 80%, 82.5%, 85%, 87.5%, 90%, 95%, or 100%. In some embodiments, the use of plinabulin can reduce the incidence of Grade 3 or 4 neutropenia by at least about 5%, 10%, 12.5%, 15%, 17.5%, 20%, 22.5%, 25%, 27.5%, 30%, 32.5%, 35%, 37.5%, 40%, 42.5%, 45%, 47.5%, 50%, 52.5%, 55%, 57.5%, 60%, 62.5%, 65%, 67.5%, 70%, 72.5%, 75%, 77.5%, 80%, 82.5%, 85%, 87.5%, 90%, 95%, or 100%. In some embodiments, the use of plinabulin can reduce the incidence of Grade 3 or 4 neutropenia by less than about 5%, 10%, 12.5%, 15%, 17.5%, 20%, 22.5%, 25%, 27.5%, 30%, 32.5%, 35%, 37.5%, 40%, 42.5%, 45%, 47.5%, 50%, 52.5%, 55%, 57.5%, 60%, 62.5%, 65%, 67.5%, 70%, 72.5%, 75%, 77.5%, 80%, 82.5%, 85%, 87.5%, 90%, 95%, or 100%. In some embodiments, the use of plinabulin can reduce the incidence of Grade 3 or 4 neutropenia in the range of about 5%-40%, 10%-40%, 12.5%-40%, 5%-50%, 10%-50%, 12.5%-50%, 15%-50%, 17.5%-50%, 20%-50%, 25%-50%, 27.5%-50%, 30%-50%, 5%-60%, 10%-60%, 12.5%-60%, 15%-60%, 17.5%-60%, 20%-60%, 25%-60%, 27.5%-60%, 30%-60%, 35%-60%, 37.5%-60%, 40%-60%, 45%-70%, or 50%-80%.

In some embodiments, the use of plinabulin can be about 10%, 20%, 30%, 40%, 50%, 60%, 70%, 80%, 90%, 100%, 110%, 120%, 130%, 140%, 150%, 160%, 170%, 180%, 190%, 200%, 225%, 250%, 275%, 300%, 350% 400%, 450%, or 500% more effective than the use of G-CSF (e.g., pegfilgrastim) in reducing the incidence of Grade 3 or 4 neutropenia. In some embodiments, the use of plinabulin can be greater than about 10%, 20%, 30%, 40%, 50%, 60%, 70%, 80%, 90%, 100%, 110%, 120%, 130%, 140%, 150%, 160%, 170%, 180%, 190%, 200%, 225%, 250%, 275%, 300%, 350% 400%, 450%, or 500% more effective than the use of G-CSF (e.g., pegfilgrastim) in reducing the incidence of Grade 3 or 4 neutropenia. In some embodiments, the use of plinabulin can be less than about 10%, 20%, 30%, 40%, 50%, 60%, 70%, 80%, 90%, 100%, 110%, 120%, 130%, 140%, 150%, 160%, 170%, 180%, 190%, 200%, 225%, 250%, 275%, 300%, 350% 400%, 450%, or 500% more effective than the use of G-CSF (e.g., pegfilgrastim) in reducing the incidence of Grade 3 or 4 neutropenia. In some embodiments, the use of plinabulin can be greater than about 10%, 20%, 30%, 40%, 50%, 60%, 70%, 80%, 90%, 100%, 110%, 120%, 130%, 140%, 150%, 160%, 170%, 180%, 190%, 200%, 225%, 250%, 275%, 300%, 350% 400%, 450%, or 500% more effective than the use of G-CSF (e.g., pegfilgrastim) in reducing the incidence of Grade 3 or 4 neutropenia.

In some embodiments, the use of plinabulin can reduce the duration of severe neutropenia by about 5%, 10%, 12.5%, 15%, 17.5%, 20%, 22.5%, 25%, 27.5%, 30%, 32.5%, 35%, 37.5%, 40%, 42.5%, 45%, 47.5%, 50%, 52.5%, 55%, 57.5%, 60%, 62.5%, 65%, 67.5%, 70%, 72.5%, 75%, 77.5%, 80%, 82.5%, 85%, 87.5%, 90%, 95%, 100%, 110%, 120%, 130%, 140%, 150%, 160%, 170%, 180%, 190%, 200%, 225%, 250%, 275%, 300%, 350% 400%, 450%, 500%, 600%, 700%, 800%, 900%, 10 times, 11 times, 12 times, 13 times, 14 times, 15 times, or 16 times. In some embodiments, the use of plinabulin can reduce the duration of severe neutropenia by greater than about 5%, 10%, 12.5%, 15%, 17.5%, 20%, 22.5%, 25%, 27.5%, 30%, 32.5%, 35%, 37.5%, 40%, 42.5%, 45%, 47.5%, 50%, 52.5%, 55%, 57.5%, 60%, 62.5%, 65%, 67.5%, 70%, 72.5%, 75%, 77.5%, 80%, 82.5%, 85%, 87.5%, 90%, 95%, 100%, 110%, 120%, 130%, 140%, 150%, 160%, 170%, 180%, 190%, 200%, 225%, 250%, 275%, 300%, 350% 400%, 450%, 500%, 600%, 700%, 800%, 900%, 10 times, 11 times, 12 times, 13 times, 14 times, 15 times, or 16 times. In some embodiments, the use of plinabulin can reduce the duration of severe neutropenia by less than about 5%, 10%, 12.5%, 15%, 17.5%, 20%, 22.5%, 25%, 27.5%, 30%, 32.5%, 35%, 37.5%, 40%, 42.5%, 45%, 47.5%, 50%, 52.5%, 55%, 57.5%, 60%, 62.5%, 65%, 67.5%, 70%, 72.5%, 75%, 77.5%, 80%, 82.5%, 85%, 87.5%, 90%, 95%, 100%, 110%, 120%, 130%, 140%, 150%, 160%, 170%, 180%, 190%, 200%, 225%, 250%, 275%, 300%, 350% 400%, 450%, 500%, 600%, 700%, 800%, 900%, 10 times, 11 times, 12 times, 13 times, 14 times, 15 times, or 16 times. In some embodiments, the use of plinabulin can reduce the duration of severe neutropenia in the range of about 5%-15 times, 20%-10 times, or 50%-500%.

In some embodiments, plinabulin can be about 5%, 10%, 12.5%, 15%, 17.5%, 20%, 22.5%, 25%, 27.5%, 30%, 32.5%, 35%, 37.5%, 40%, 42.5%, 45%, 47.5%, 50%, 52.5%, 55%, 57.5%, 60%, 62.5%, 65%, 67.5%, 70%, 72.5%, 75%, 77.5%, 80%, 82.5%, 85%, 87.5%, 90%, 95%, 100%, 110%, 120%, 130%, 140%, 150%, 160%, 170%, 180%, 190%, 200%, 225%, 250%, 275%, 300%, 350% 400%, 450%, 500%, 600%, 700%, 800%, 900%, 10 times, 11 times, 12 times, 13 times, 14 times, 15 times, or 16 times more effective than G-CSF (e.g., pegfilgrastim) in reducing the duration of severe neutropenia. In some embodiments, plinabulin can be greater than about 5%, 10%, 12.5%, 15%, 17.5%, 20%, 22.5%, 25%, 27.5%, 30%, 32.5%, 35%, 37.5%, 40%, 42.5%, 45%, 47.5%, 50%, 52.5%, 55%, 57.5%, 60%, 62.5%, 65%, 67.5%, 70%, 72.5%, 75%, 77.5%, 80%, 82.5%, 85%, 87.5%, 90%, 95%, 100%, 110%, 120%, 130%, 140%, 150%, 160%, 170%, 180%, 190%, 200%, 225%, 250%, 275%, 300%, 350% 400%, 450%, 500%, 600%, 700%, 800%, 900%, 10 times, 11 times, 12 times, 13 times, 14 times, 15 times, or 16 times more effective than G-CSF (e.g., pegfilgrastim) in reducing the duration of severe neutropenia. In some embodiments, plinabulin can be less than about 5%, 10%, 12.5%, 15%, 17.5%, 20%, 22.5%, 25%, 27.5%, 30%, 32.5%, 35%, 37.5%, 40%, 42.5%, 45%, 47.5%, 50%, 52.5%, 55%, 57.5%, 60%, 62.5%, 65%, 67.5%, 70%, 72.5%, 75%, 77.5%, 80%, 82.5%, 85%, 87.5%, 90%, 95%, 100%, 110%, 120%, 130%, 140%, 150%, 160%, 170%, 180%, 190%, 200%, 225%, 250%, 275%, 300%, 350% 400%, 450%, 500%, 600%, 700%, 800%, 900%, 10 times, 11 times, 12 times, 13 times, 14 times, 15 times, or 16 times more effective than G-CSF (e.g., pegfilgrastim) in reducing the duration of severe neutropenia. In some embodiments, plinabulin can be in the range of about 5%-15 times, 20%-10 times, or 50%-500% more effective than G-CSF (e.g., pegfilgrastim) in reducing the duration of severe neutropenia.

The administration period can be a multi-week treatment cycle as long as the tumor remains under control and the regimen is clinically tolerated. In some embodiments, a single dosage of plinabulin or other therapeutic agent can be administered once a week, and preferably once on each of day 1 and day 8 of a three-week (21 day) treatment cycle. In some embodiments, a single dosage of plinabulin or other therapeutic agent can be administered once a week, twice a week, three times per week, four times per week, five times per week, six times per week, or daily during a one-week, two-week, three-week, four-week, or five-week treatment cycle. The administration can be on the same or different day of each week in the treatment cycle.

The treatment cycle can be repeated as long as the regimen is clinically tolerated. In some embodiments, the treatment cycle is repeated for n times, wherein n is an integer in the range of 2 to 30. In some embodiments, n is 2, 3, 4, 5, 6, 7, 8, 9, or 10. In some embodiments, a new treatment cycle can occur immediately after the completion of the previous treatment cycle. In some embodiments, a new treatment cycle can occur a period of time after the completion of the previous treatment cycle.

Administration of the pharmaceutical compositions described herein can be via any of the accepted modes of administration for agents that serve similar utilities including, but not limited to, orally, sublingually, buccally, subcutaneously, intravenously, intranasally, topically, transdermally, intradermally, intraperitoneally, intramuscularly, intrapulmonarilly, vaginally, rectally, intraocularly, or intragastrically (e.g., gastric feeding tube. Oral and parenteral administrations are customary in treating the indications that are the subject of the preferred embodiments.

Some embodiments relate to a method of reducing neutropenia in a subject, comprising administering plinabulin or a pharmaceutically acceptable salt thereof to a subject in need thereof. In some embodiments, the neutropenia is chemotherapy-induced. In some embodiments, the neutropenia is induced by administration of the first chemotherapeutic composition that is myelosuppresive. The chemotherapeutic composition can include one or more chemotherapeutic agents. In some embodiments, the chemotherapeutic agent is selected from the group consisting of cyclophosphamide, doxorubicin, paclitaxel, carboplatin, cisplatin, irinotecan, topotecan, and pharmaceutically acceptable salts thereof, or combinations of two or more of the foregoing, or combinations of one or more of the foregoing and docetaxel. In some embodiments, the chemotherapeutic agent is selected from the group consisting of phosphamides, rubicins, platins, tecans, and pharmaceutically acceptable salts thereof, or combinations of two or more of the foregoing, or combinations of one or more of the foregoing and docetaxel.

In some embodiments, the chemotherapeutic agent is selected from the group consisting of phosphamides, rubicins, platins, tecans, taxanes, and pharmaceutically acceptable salts thereof, or combinations of two or more of the foregoing. In some embodiments, the first chemotherapeutic composition can comprises one or more agents selected from the group consisting of phosphamides, rubicins, platins, tecans, and pharmaceutically acceptable salts thereof, or combinations of two or more of the foregoing. In some embodiments, the chemotherapeutic composition (e.g., the second, the third, the fourth, the fifth, the sixth, the seventh, the eighth chemotherapeutic composition) can comprises one or more agents selected from the group consisting of phosphamides, rubicins, platins, tecans, taxanes, and pharmaceutically acceptable salts thereof, or combinations of two or more of the foregoing. In some embodiments, the platin can be one or more selected from the group consisting of cisplatin, carboplatin, and oxaliplatin, nedaplatin, triplatin tetranitrate, phenanthriplatin, picoplatin, and satraplatin. In some embodiments, the tecan can be topotecan, irinotecan, or combination thereof. In some embodiments, the phosphamides can be cyclophosphamide, ifosamide, or combination thereof. In some embodiments, the taxane can be selected from the group consisting of docetaxel, paclitaxel, cabazitaxel. In some embodiments, the rubicin can be one or more selected from doxorubicin, epirubicin, daunorubicin, and valrubicin.

In some embodiments, the neutropenia is induced by radiation therapy. Some embodiments include reducing the likelihood of onset of, or reducing the severity of, neutropenia in a subject, comprising administering plinabulin to a subject in need thereof.

Some embodiments of the foregoing methods comprise administering plinabulin or a pharmaceutically acceptable salt thereof and one or more additional chemotherapeutic agents. In various embodiments, the additional chemotherapeutic agent is selected from the group consisting of cyclophosphamide, doxorubicin, paclitaxel, carboplatin, cisplatin, irinotecan, topotecan, and pharmaceutically acceptable salts thereof, or combinations of two or more of the foregoing, or combinations of one or more of the foregoing and docetaxel. In one embodiment, plinabulin and the one or more additional chemotherapeutic agent are administered simultaneously. In one such embodiment, administration in combination is accomplished by combining the agents in a single dosage form. In another embodiment, the agents are administered sequentially. In one embodiment the agents are administered through the same route, such as orally or intravenously. In another embodiment, the agents are administered through different routes, such as one being administered orally and another being administered i.v. In some embodiments, the time period between administration of one or more agent and administration of the co-administered one or more agent can be about 1 hour, 2 hours, 3 hours, 5 hours, 8 hours, 10 hours, 12 hours, 15 hours, 18 hours, 20 hours, 24 hours, 36 hours, 48 hours, 3 days, 4 days, 5 days, 6 days, 7 days, 10 days, 14 days, 21 days, 28 days, or 30 days. In some embodiments, plinabulin is administered prior to administration of the one or more additional chemotherapeutic agents. In other embodiments, the additional chemotherapeutic agents are administered prior to plinabulin.

In some embodiments, the method described herein comprises co-administering one or more chemotherapeutic agents and plinabulin. In some embodiments, the method described herein comprises co-administering two chemotherapeutic agents and plinabulin. In some embodiments, the method described herein comprises co-administering three chemotherapeutic agents and plinabulin. In some embodiments, the method described herein comprises co-administering four chemotherapeutic agents and plinabulin.

In some embodiments, when a second and/or third chemotherapeutic agents are administered with the first chemotherapeutic agent and plinabulin, the second or third chemotherapeutic agent can be administered prior to, after, or concurrently with the coadministration of the first chemotherapeutic agent and plinabulin. In some embodiments, the administration schedule of the second or third chemotherapeutic agent can be different from the first chemotherapeutic agent. In some embodiments, the administration schedule of the second or third chemotherapeutic agent can be the same as the first chemotherapeutic agent.

In some embodiments, the additional chemotherapeutic agent does not include docetaxel. In some embodiments, the additional chemotherapeutic agent does not include a taxane.

Some embodiments comprise administering plinabulin or a pharmaceutically acceptable salt thereof and radiation therapy to a subject Some embodiments include identifying that a subject is suffering from neutropenia and then administering plinabulin or a pharmaceutically acceptable salt thereof to the subject. Other embodiments include administrating plinabulin or a pharmaceutically acceptable salt thereof to a subject before detection of neutropenia to reduce the incidence or severity thereof. For example, some embodiments include identifying a subject that is at risk for developing neutropenia (e.g., due to myelosuppressive chemotherapy or radiation therapy) but does not yet exhibit neutropenia, and then administering plinabulin or a pharmaceutically acceptable salt thereof to the subject.

In some embodiments of the foregoing methods, no additional agent that acts to reduce neutropenia are administered. For example, in some embodiments, the methods are practiced without administering a granulocyte-colony stimulating factor (e.g., filgrastim). In some embodiments, the methods are practiced without administering any additional active agent beyond the agents recited in above.

In some of the foregoing embodiments, the subject is a human.

In some embodiments, the methods described above can be achieved by administering plinabulin and any additional chemotherapeutic agents via any of the accepted modes of administration for agents that serve similar utilities including, but not limited to, orally, sublingually, buccally, subcutaneously, intravenously, intranasally, topically, transdermally, intradermally, intraperitoneally, intramuscularly, intrapulmonarilly, vaginally, rectally, intraocularly, or intragastrically. Oral and parenteral administrations are customary in treating the indications that are the subject of the preferred embodiments.

The administration period can be a multi-week treatment cycle. In some embodiments, a single dosage of plinabulin or other therapeutic agent can be administered once a week, and preferably once on each of day 1 and day 8 of a three-week (21 day) treatment cycle. In some embodiments, a single dosage of plinabulin or other therapeutic agent can be administered once a week, twice a week, three times per week, four times per week, five times per week, six times per week, or daily during a one-week, two-week, three-week, four-week, or five-week treatment cycle. The administration can be on the same or different day of each week in the treatment cycle.

The treatment cycle can be repeated as long as the regimen is clinically tolerated. In some embodiments, the treatment cycle is repeated for n times, wherein n is an integer in the range of 2 to 30. In some embodiments, n is 2, 3, 4, 5, 6, 7, 8, 9, or 10. In some embodiments, a new treatment cycle can occur immediately after the completion of the previous treatment cycle. In some embodiments, a new treatment cycle can occur a period of time after the completion of the previous treatment cycle.

Pharmaceutical Compositions

Some embodiments include pharmaceutical compositions comprising plinabulin or a pharmaceutically effective salt thereof and an additional chemotherapeutic agent. In various embodiments, the additional chemotherapeutic agent is selected from the group consisting of phosphamides, rubicins, platins, tecans, and pharmaceutically acceptable salts thereof, or combinations of two or more of the foregoing, or combinations of one or more of the foregoing and docetaxel. In some embodiments, the additional chemotherapeutic agent is not taxane. In some embodiments, the additional chemotherapeutic agent is not docetaxel. In various embodiments, the additional chemotherapeutic agent is selected from the group consisting of cyclophosphamide, doxorubicin, carboplatin, cisplatin, topotecan, and pharmaceutically acceptable salts thereof, or combinations of two or more of the foregoing, or combinations of one or more of the foregoing and docetaxel. In various embodiments, the additional chemotherapeutic agent is selected from the group consisting of cyclophosphamide, doxorubicin, paclitaxel, carboplatin, cisplatin, irinotecan, and pharmaceutically acceptable salts thereof, or combinations of two or more of the foregoing, or combinations of one or more of the foregoing and docetaxel. In some embodiments, the pharmaceutical composition comprises plinabulin or a pharmaceutically effective salt thereof and doxorubicin or a pharmaceutically effective salt thereof. In some embodiments, the pharmaceutical composition comprises plinabulin or a pharmaceutically effective salt thereof, doxorubicin or a pharmaceutically effective salt thereof, and docetaxel or a pharmaceutically effective salt thereof. In some embodiments, the pharmaceutical composition comprises plinabulin or a pharmaceutically effective salt thereof and paclitaxel or a pharmaceutically acceptable salt thereof. In some embodiments, the pharmaceutical composition comprises plinabulin or a pharmaceutically effective salt thereof and carboplatin or a pharmaceutically acceptable salt thereof. In some embodiments, the pharmaceutical composition comprises plinabulin or a pharmaceutically effective salt thereof, paclitaxel or a pharmaceutically acceptable salt thereof, and carboplatin or a pharmaceutically acceptable salt thereof. In some embodiments, the pharmaceutical composition comprises plinabulin or a pharmaceutically effective salt thereof and cisplatin or a pharmaceutically acceptable salt thereof. In some embodiments, the pharmaceutical composition comprises plinabulin or a pharmaceutically effective salt thereof and irinotecan or a pharmaceutically acceptable salt thereof. In some embodiments, the pharmaceutical composition comprises plinabulin or a pharmaceutically effective salt thereof and cyclophosphamide or a pharmaceutically acceptable salt thereof. In some embodiments, the pharmaceutical composition does not comprise docetaxel. In some embodiments, the pharmaceutical composition does not comprise a taxane.

In some embodiments, the pharmaceutical compositions described above do not comprise any additional agent that acts to reduce neutropenia. For example, in some embodiments, the pharmaceutical compositions do not include a granulocyte-colony stimulating factor (e.g., filgrastim). In some embodiments, the pharmaceutical compositions do not include any additional active agent beyond the agents recited in the compositions above.

Other embodiments include two or more separate pharmaceutical compositions, one of which comprises plinabulin or a pharmaceutically acceptable salt thereof, and one or more other pharmaceutical compositions that comprise additional chemotherapeutic agents. In various embodiments, the additional chemotherapeutic agent is selected from the group consisting of cyclophosphamide, doxorubicin, paclitaxel, carboplatin, cisplatin, irinotecan, and pharmaceutically acceptable salts thereof.

In some embodiments, the compositions described above can further include one or more pharmaceutically acceptable diluents. In some embodiments, the pharmaceutically acceptable diluent can include Kolliphor HS-15® (Polyethylene glycol (15)-hydroxystearate, kolliphor). In some embodiments, the pharmaceutically acceptable diluent can include propylene glycol. In some embodiments, the pharmaceutically acceptable diluents can include kolliphor and propylene glycol. In some embodiments, the pharmaceutically acceptable diluents can include kolliphor and propylene glycol, wherein the kolliphor is about 40% by weight and propylene glycol is about 60% by weight based on the total weight of the diluents. In some embodiments, the composition can further include one or more other pharmaceutically acceptable excipients.

In some embodiments, the compositions described above can further include one or more pharmaceutically acceptable carrier or excipient. The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerin, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The compositions described herein are preferably provided in unit dosage form. As used herein, a "unit dosage form" is a composition containing an amount of a compound or composition that is suitable for administration to an animal, preferably a mammalian subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, although a single administration is not specifically excluded. The skilled artisan will recognize that the formulation does not specifically contemplate the entire course of therapy and such decisions are left for those skilled in the art of treatment rather than formulation.

Standard pharmaceutical formulation techniques can be used to make the pharmaceutical compositions described herein, such as those disclosed in Remington's The Science and Practice of Pharmacy, 21st Ed., Lippincott Williams & Wilkins (2005), incorporated herein by reference in its entirety.

The compositions as described above may be in any of a variety of suitable forms for a variety of routes for administration, for example, for oral, sublingual, buccal, nasal, rectal, topical (including transdermal and intradermal), ocular, intracerebral, intracranial, intrathecal, intra-arterial, intravenous, intramuscular, or other parental routes of administration. The skilled artisan will appreciate that oral and nasal compositions include compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropies, surface-active agents, and encapsulating substances. Optional pharmaceutically-active materials may be included, which do not substantially interfere with the activity of the compound or composition. The amount of carrier employed in conjunction with the compound or composition is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules (e.g., liquid gel capsule and solid gel capsule), granules and bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carriers suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject composition is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A liquid composition, which is formulated for topical ophthalmic use, is formulated such that it can be administered topically to the eye. The comfort may be maximized as much as possible, although sometimes formulation considerations (e.g. drug stability) may necessitate less than optimal comfort. In the case that comfort cannot be maximized, the liquid may be formulated such that the liquid is tolerable to the patient for topical ophthalmic use. Additionally, an ophthalmically acceptable liquid may either be packaged for single use, or contain a preservative to prevent contamination over multiple uses.

For ophthalmic application, solutions or medicaments are often prepared using a physiological saline solution as a major vehicle. Ophthalmic solutions may preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

Ophthalmically acceptable antioxidants include, but are not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium (EDTA), although other chelating agents may also be used in place or in conjunction with it.

For topical use, creams, ointments, gels, solutions or suspensions, etc., containing the composition disclosed herein are employed. Topical formulations may generally be comprised of a pharmaceutical carrier, co-solvent, emulsifier, penetration enhancer, preservative system, and emollient.

For intravenous administration, the compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, *PDA J Pharm Sci and Tech* 1998, 52 238-311 and Nema et al., Excipients and Their Role in Approved Injectable Products: Current Usage and Future Directions, *PDA J Pharm Sci and Tech* 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The compositions for intravenous administration may be provided to caregivers in the form of one or more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration. In embodiments that include administering a combination of a compound described herein and another agent, the combination may be provided to caregivers as a mixture, or the caregivers may mix the two agents prior to administration, or the two agents may be administered separately.

The actual dose of the active compounds described herein depends on the specific compound, and on the condition to be treated; the selection of the appropriate dose is well within the knowledge of the skilled artisan. In some embodiments, a single dose of Plinabulin or other therapeutic agent may be from about 5 mg/m$^2$ to about 150 mg/m$^2$ of body surface area, from about 5 mg/m$^2$ to about 100 mg/m$^2$ of body surface area, from about 10 mg/m$^2$ to about 100 mg/m$^2$ of body surface area, from about 10 mg/m$^2$ to about 80 mg/m$^2$ of body surface area, from about 10 mg/m$^2$ to about 50 mg/m$^2$ of body surface area, from about 10 mg/m$^2$ to about 40 mg/m$^2$ of body surface area, from about 10 mg/m$^2$ to about 30 mg/m$^2$ of body surface area, from about 13.5 mg/m$^2$ to about 100 mg/m$^2$ of body surface area, from about 13.5 mg/m$^2$ to about 80 mg/m$^2$ of body surface area, from about 13.5 mg/m$^2$ to about 50 mg/m$^2$ of body surface area, from about 13.5 mg/m$^2$ to about 40 mg/m$^2$ of body surface area, from about 13.5 mg/m$^2$ to about 30 mg/m$^2$ of body surface area, from about 15 mg/m$^2$ to about 80 mg/m$^2$ of body surface area, from about 15 mg/m$^2$ to about 50 mg/m$^2$ of body surface area, or from about 15 mg/m$^2$ to about 30 mg/m$^2$ of body surface area. In some embodiments, a single dose of plinabulin or other therapeutic agent may be from about 13.5 mg/m$^2$ to about 30 mg/m$^2$ of body surface area. In some embodiments, a single dose of plinabulin or other therapeutic agent may be about 5 mg/m$^2$, about 10 mg/m$^2$, about 12.5 mg/m$^2$, about 13.5 mg/m$^2$, about 15 mg/m$^2$, about 17.5 mg/m$^2$, about 20 mg/m$^2$, about 22.5 mg/m$^2$, about 25 mg/m$^2$, about 27.5 mg/m$^2$, about 30 mg/m$^2$, about 40 mg/m$^2$, about 50 mg/m$^2$, about 60 mg/m$^2$, about 70 mg/m$^2$, about 80 mg/m$^2$, about 90 mg/m$^2$, or about 100 mg/m$^2$, of body surface area.

In some embodiments, a single dose of plinabulin or other therapeutic agent may be from about 5 mg to about 300 mg, from about 5 mg to about 200 mg, from about 7.5 mg to about 200 mg, from about 10 mg to about 100 mg, from about 15 mg to about 100 mg, from about 20 mg to about 100 mg, from about 30 mg to about 100 mg, from about 40 mg to about 100 mg, from about 10 mg to about 80 mg, from about 15 mg to about 80 mg, from about 20 mg to about 80 mg, from about 30 mg to about 80 mg, from about 40 mg to about 80 mg, from about 10 mg to about 60 mg, from about 15 mg to about 60 mg, from about 20 mg to about 60 mg, from about 30 mg to about 60 mg, or from about 40 mg to about 60 mg, In some embodiments, a single dose of plinabulin or other therapeutic agent may be from about 20 mg to about 60 mg, from about 27 mg to about 60 mg, from about 20 mg to about 45 mg, or from about 27 mg to about 45 mg. In some embodiments, a single dose of plinabulin or other therapeutic agent may be about 5 mg, about 10 mg, about 12.5 mg, about 13.5 mg, about 15 mg, about 17.5 mg, about 20 mg, about 22.5 mg, about 25 mg, about 27 mg, about 30 mg, about 40 mg, about 50 mg, about 60 mg, about 70 mg, about 80 mg, about 90 mg, about 100 mg, about 125 mg, about 150 mg, or about 200 mg.

In some embodiments, the compositions described herein can be administered or used in combination with other treatments such as radiation or biologic therapies.

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples.

EXAMPLES

Example 1

The effect of plinabulin alone, cyclophosphamide alone, and the combination of plinabulin and cyclophosphamide on neutropenia was evaluated in male Sprague-Dawley rats. Fifteen rats each were placed in 4 treatment groups according to Table 1. The indicated doses were administered through intraperitoneal injection on Day 1 with Administration 2 being given 1 hour following Administration 1.

TABLE 1

| Treatment Groups | | | |
|---|---|---|---|
| Group No. | Treatment | Administration 1 | Administration 2 |
| 1 | Naïve control | — | — |
| 2 | Vehicle + Plinabulin | Vehicle 10 ml/kg | Plinabulin |

TABLE 1-continued

Treatment Groups

| Group No. | Treatment | Administration 1 | Administration 2 |
|---|---|---|---|
| 3 | Cyclophosphamide + Vehicle | Cyclophosphamide 12.5 mg/kg (10 ml/kg) | 7.5 mg/kg (7.5 ml/kg) Vehicle 7.5 ml/kg |
| 4 | Cyclophosphamide + Plinabulin | Cyclophosphamide 12.5 mg/kg (10 ml/kg) | Plinabulin 7.5 mg/kg (7.5 ml/kg) |

For treatment groups that included administration of a vehicle, the vehicle consisted of 7.11% Tween 80 (v/v): 25.5% Propylene glycol (v/v): 67.4% D5W (v/v). D5W is 5% dextrose in water for injection. For groups that included administration of plinabulin, plinabulin is first dissolved in the Tween 80-PG mixture and then diluted with D5W. For groups that included administration of cyclophosphamide, a solution of cyclophosphamide was prepared, on the day of use, by dissolution in sterile water for injection to the desired final concentration.

The animals were randomized based on body weight and assigned to groups. Before the initiation of dosing, any assigned animals considered unsuitable for use in the study were replaced by alternate animals obtained from the same shipment and maintained under the same environmental conditions.

PMI Nutrition International Certified Rodent Chow No. 5CR4 was provided ad libitum throughout the study, except during designated procedures. The same diet in meal form was provided to individual animals as warranted by clinical signs (e.g., broken/damaged incisors or other health changes).

Blood was collected by jugular venipuncture for Day −1 bleeds and terminally via abdominal aorta under anesthesia for Day 2 (5 rats per Group i.e. total 20 rats), Day 3 (5 rats per Group i.e. total 20 rats) and Day 10 (5 rats per Group i.e. total 20 rats). After collection, the samples were tested for total and differential cell counts. Five rats per group were terminated on Days 2, 3, and 10. Animals were anesthetized with isoflurane (1-5%) and ~1-2.0 mL of blood will be collected via abdominal aorta. After collection, 0.3 mL was transferred to EDTA tubes and analyzed for total and differential cell counts. Immediately after blood collection, the animals were euthanized by exsanguination of the abdominal aorta.

FIG. 1 is a graph of neutrophil count 24 hours post dosing of cyclophosphamide, plinabulin, or the combination of cyclophosphamide and plinabulin (i.e., from the 20 rats that were terminated on Day 2). The results indicate that administration of cyclophosphamide caused a decrease in neutrophil count while the combination of plinabulin and cyclophosphamide maintained the neutrophil count. These results indicate that plinabulin reduced the neutropenia caused by cyclophosphamide (p=0.0584). Plinabulin alone did not reduce the neutrophil count.

Figure 2:
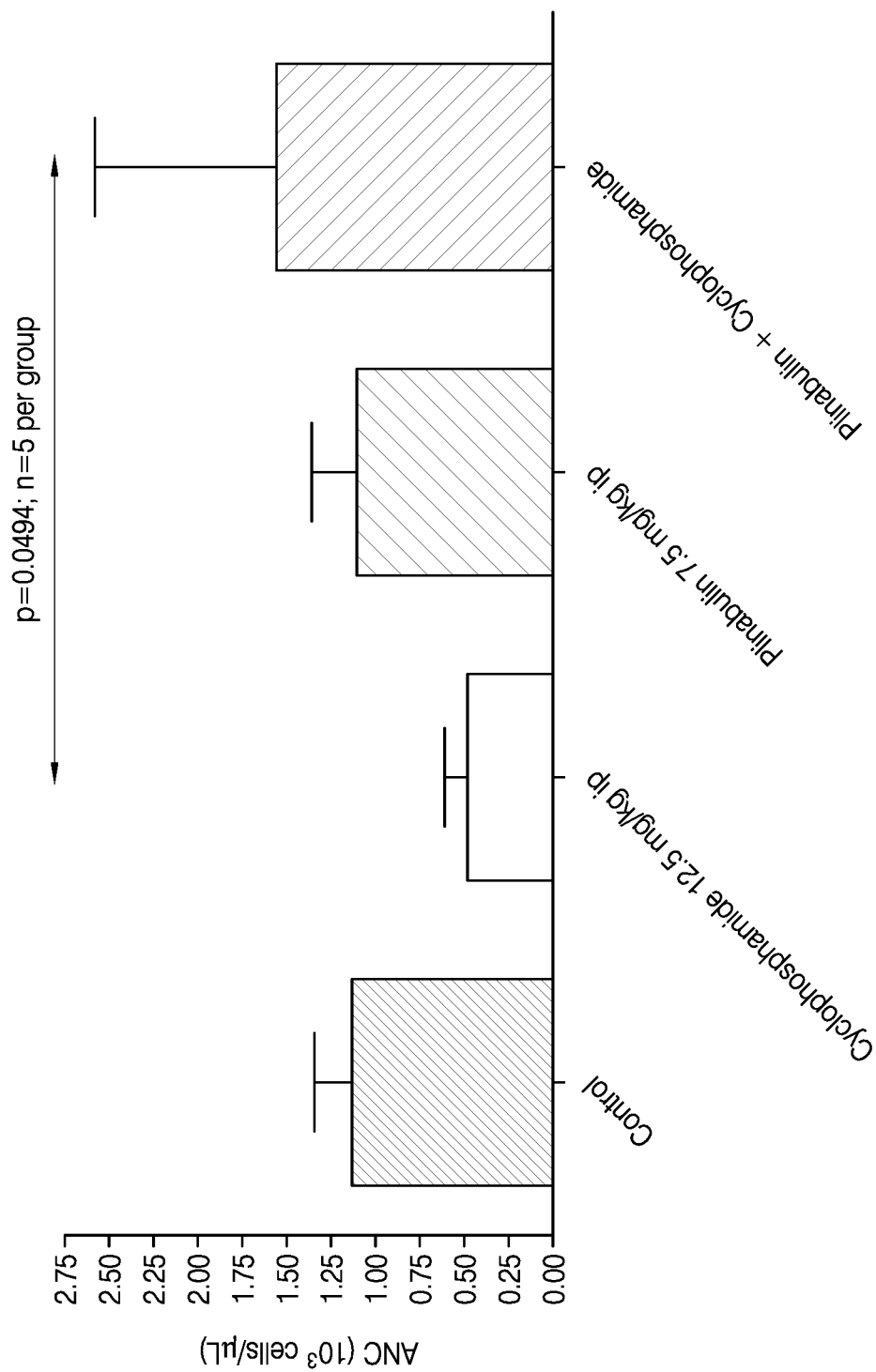
FIG. 2 is a graph of neutrophil count 48 hours post dosing of cyclophosphamide, plinabulin, or the combination of cyclophosphamide and plinabulin.

FIG. 2 is a graph of neutrophil count 48 hours post dosing of cyclophosphamide, plinabulin, or the combination of cyclophosphamide and plinabulin (i.e., from the 20 rats that were terminated on Day 3). These results also indicate that administration of cyclophosphamide caused a decrease in neutrophil count while the combination of plinabulin and cyclophosphamide maintained the neutrophil count. These results indicate that plinabulin reduced the neutropenia caused by cyclophosphamide (p=0.0494). Plinabulin alone did not reduce the neutrophil count.

Figure 3:
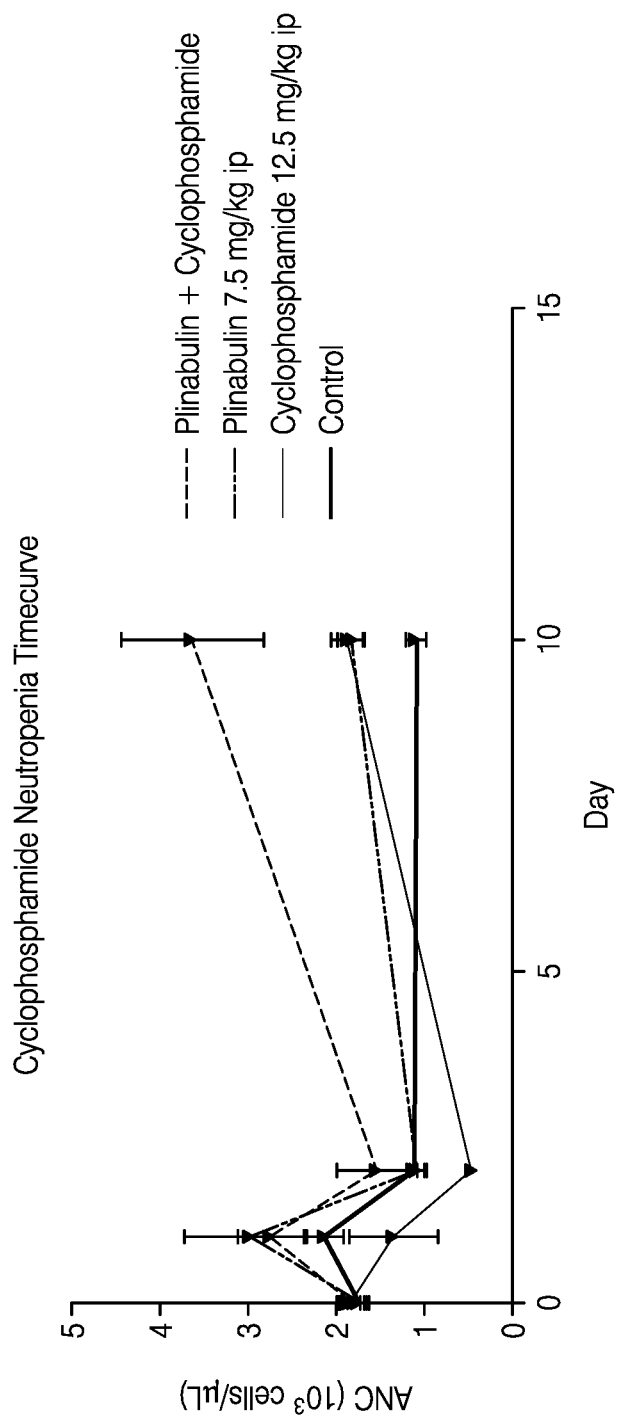
FIG. 3 is a graph of the time course of neutrophil count after administration of cyclophosphamide, plinabulin, or the combination of cyclophosphamide and plinabulin.

FIG. 3 depicts results from all rats, including the Day −1 bleed as well as the terminations on Days 2, 3, and 10. Again, the results indicate that plinabulin reduced the neutropenia caused by cyclophosphamide.

Example 2

A study was performed to evaluate the effect of Plinabulin in reducing or treating neutropenia induced by chemotherapeutic agents such as cyclophaphamide. Male Sprague-Dawley rats were first treated with cyclophosphamide, or vehicle saline (control). The control sample contained 7.1% Tween 80 (v/v), 25.5% Propylene glycol (v/v), and 67.4% D5W (5% dextrose in water) (v/v). One hour later, the rats were dosed with Plinabulin or its vehicle following the administration schedule shown in Table 2. Each test group included 15 rats.

TABLE 2

Treatment Groups

| Group No. | Treatment | Administration 1 | Administration 2 |
|---|---|---|---|
| 1 | Naïve control | — | — |
| 2 | Cyclophosphamide + Vehicle | Cyclophosphamide 12.5 mg/kg, (10 ml/kg) | Vehicle 7.5 ml/kg, |
| 3 | Cyclophosphamide + Plinabulin | Cyclophosphamide 12.5 mg/kg, (10 ml/kg) | Plinabulin 7.5 mg/kg (7.5 ml/kg) |
| 4 | Vehicle + Plinabulin | Vehicle (10 ml/kg) | Plinabulin 7.5 mg/kg (7.5 ml/kg) |

Figure 4:
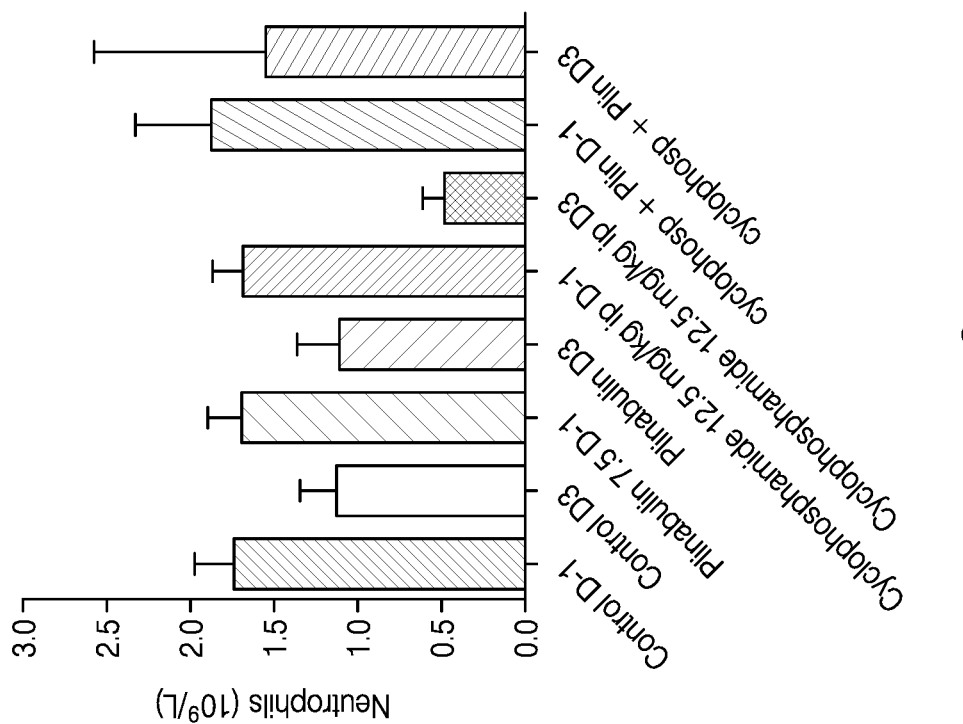
FIG. 4 shows the absolute neutrophil count (ANC) on Day 1 and Day 3 post dosing of cyclophosphamide, the combination of cyclophosphamide and plinabulin, and control groups.

Blood collection was performed for absolute neutrophil counts in blood samples collected at Day −1 (pre-dose), Day 2 (24 h), Day 3 (48 h), Day 10 (9 days) and Day 15 (14 days). The absolute neutrophil counts (ANC) measured are listed in Table 3 and shown in FIG. 4. Table 4 shows the ANC expressed as percentage of the day −1 base line.

TABLE 3

ANCs ($10^3$ Cells/μL) on Day −1 and Day 3 for the treatment groups (Mean ± SD) N = 5 rats per group.

| Day | Control | Plinabulin | Cyclophosphamide | Cyclophosphamide + Plinabulin |
|---|---|---|---|---|
| −1 | 1.73 ± 0.24 | 1.69 ± 0.21 | 1.68 ± 0.19 | 1.87 ± 0.46 |
| 3 | 1.22 ± 0.22 | 1.10 ± 0.26 | 0.48 ± 0.13 | 1.55 ± 1.03 |

TABLE 4

ANCs Expressed as Percent of Baseline (Day −1), with Statistical significance (t-test)

| Group | Control | Plinabulin | Cyclophosph. | Cyclophosph. + Plin |
|---|---|---|---|---|
| ANC % (Day −1) | 70.5 | 65.1 | 28.5 | 82.9 |
| P value | 0.0034 | 0.0045 | <0.00001 | 0.5437 NS |

Figure 5:
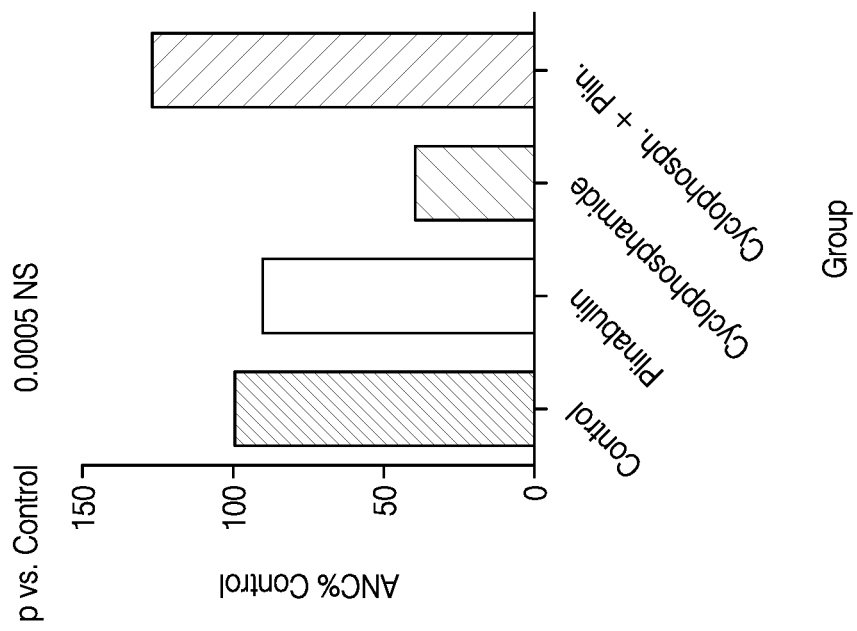
FIG. 5 shows the ANC levels on Day 3 post dosing of cyclophosphamide, plinabulin, or the combination of cyclophosphamide and plinabulin as expressed as percentage of the ANC of the control group.
Figure 6:
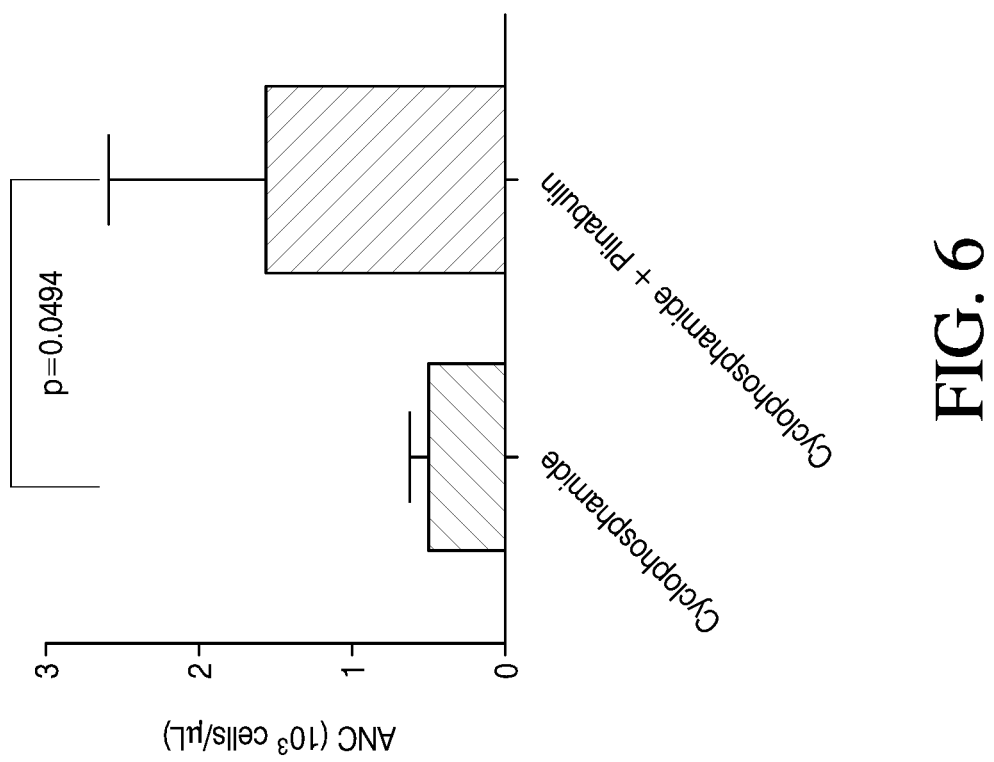
FIG. 6 shows the ANC level on Day 3 post dosing of cyclophosphamide and the combination of cyclophosphamide and plinabulin.

The control group showed some changes from the baseline (Day −1), and this change was compared with the changes in other treatment groups. These were expressed as a percentage of the control level on Day 3. Table 5 and FIG. 5 show the ANC levels in each group on Day 3, and the difference between the chemotherapeutic with and without plinabulin treatment is shown in Table 6 and FIG. 6.

TABLE 5

ANC Levels in Each Group on Day 3, Expressed as Percent of Control ANC on Day 3

| Group | Control | Plinabulin | Cyclophos-phamide | Cyclophos-phamide + Plinabulin |
|---|---|---|---|---|
| % Day 3 Control | 100.0 | 90.2 | 39.3 | 127.0 |
| P Value | — | 0.889 NS | 0.0005 | 0.39 NS |

TABLE 6

Comparison of ANC Levels of Chemotherapeutic Alone vs. the combination of chemotherapeutic and plinabulin on Day 3

| Group | Cyclophos-phamide | Cyclophos-phamide + Plinabulin |
|---|---|---|
| ANC ($10^3/\mu L$) | 0.48 ± 0.13 | 1.55 ± 1.03 |
| P value Chemo vs. Chemo + Plinabulin | | 0.0494 |

As shown in this study, the chemotherapeutic agents, cyclophosphamide respectively induced neutropenia in rats at around 48 h after a single intra-peritoneal injection. The administration of plinabulin reversed cyclophosphamide-induced neutropenia and helped increase ANC levels.

Example 3

A study was performed to evaluate the effect of plinabulin in reducing or treating doxorubicin induced neutropenia. Male Sprague-Dawley rats were first treated with doxorubicin or vehicle saline (control). The control sample included 7.1% Tween 80 (v/v), 25.5% Propylene glycol (v/v), 67.4% D5W (v/v). One hour later, the rats were dosed with Plinabulin or its vehicle following the administration schedule shown in Table 7. Each test group included 6 rats. The doxorubicin was administered intravenously, and plinabulin was administered through intraperitoneal injection.

TABLE 7

Treatment groups

| Group | Treatment | Doxorubicin Dose (mg/kg) | Plinabulin Dose (mg/kg) |
|---|---|---|---|
| A | Naïve Control | — | — |
| B | Doxorubicin + Vehicle | 3 | 0 |
| C | Plinabulin | — | 7.5 |
| D | Doxorubicin + Plinabulin | 3 | 1.75 |
| E | Doxorubicin + Plinabulin | 3 | 3.5 |
| F | Doxorubicin + Plinabulin | 3 | 7.5 |

Figure 7:
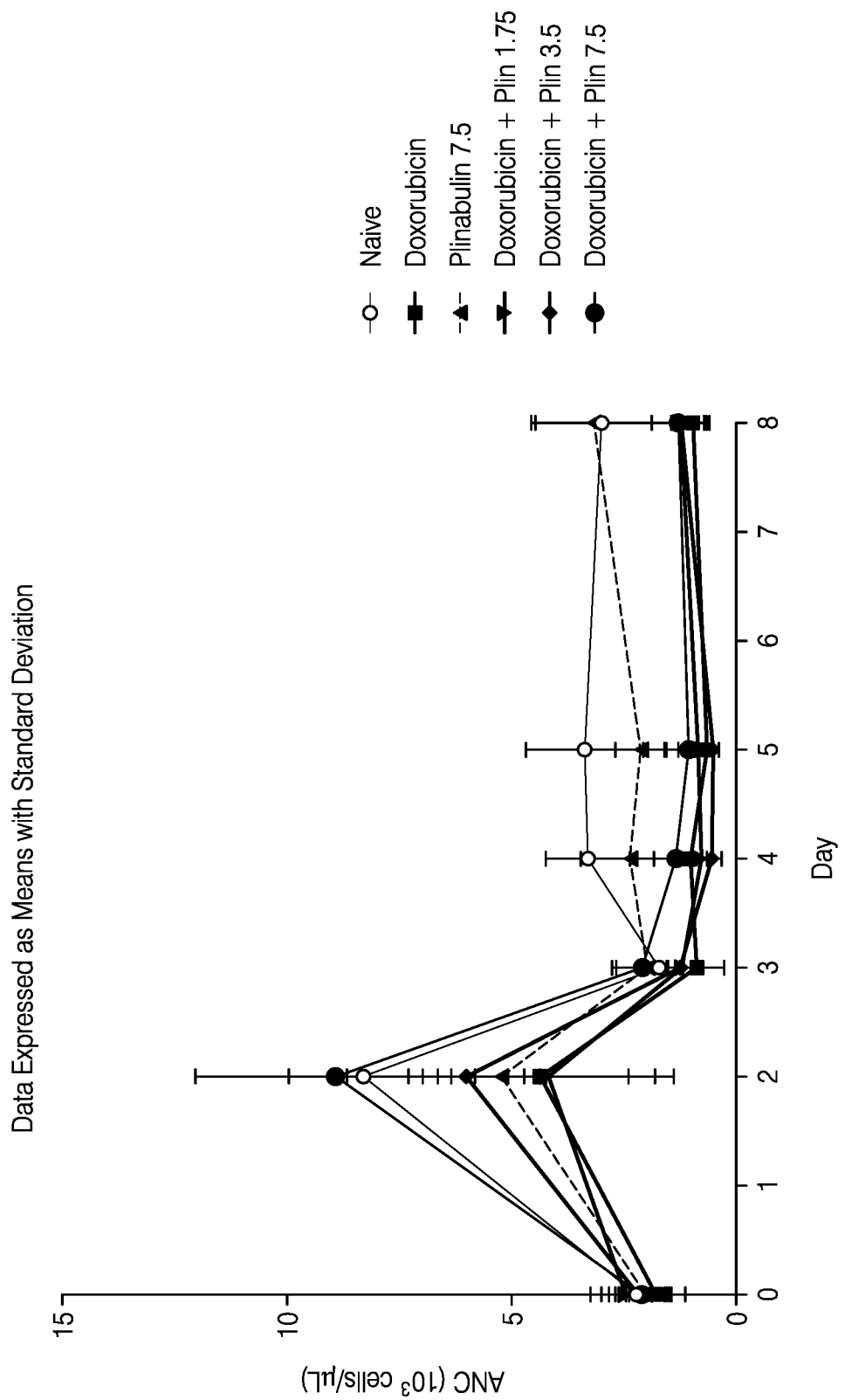
FIG. 7 is a graph of the time course of ANC level after administration of naïve, doxorubicin, plinabulin, and the combination of doxorubicin and plinabulin.

Blood collection was performed for ANC in blood samples collected at Day −1 (pre-dose), Day 2, Day 3, Day 4, Day 5 and Day 8 post single dosing with control, doxorubicin at Day 1 followed by plinabulin, or plinabulin vehicle as control one hour later. The ANC decreased following doxorubicin administration with a duration of at least 8 days. An increase in ANC was noted in all groups 24 hours after doxorubicin. This change rapidly normalized in control and plinabulin only-treated groups. The ANC in plinabulin only treated rats was not statistically different from naïve animals at any time point. (Table 8, FIG. 7)

TABLE 8

A time course change of ANC ($10^3/\mu L$) levels expressed as Mean ± SD (n)

| Day | Naive | Doxorubicin 3.0 mg/kg | Plinabulin 7.5 mg/kg | Doxorubicin + Plinabulin 1.75 mg/kg | Doxorubicin + Plinabulin 3.5 mg/kg | Doxorubicin + Plinabulin 7.5 mg/kg |
|---|---|---|---|---|---|---|
| −1 | 2.23 ± 0.787 (5) | 1.79 ± 0.666 (6) | 2.02 ± 0.378 (6) | 2.46 ± 0.792 (6) | 2.20 ± 0.645 (6) | 2.12 ± 0.582 (6) |
| 2 | 8.31 ± 1.658 (6)* | 4.37 ± 1.985 (6)*,# | 5.24 ± 3.429 (6) | 4.39 ± 2.802 (6)# | 6.01 ± 1.290 (6)*,# | 8.93 ± 3.107 (6)*,! |
| 3 | 1.73 ± 0.474 (6) | 0.88 ± 0.156 (6)*,# | 1.98 ± 0.792 (6) | 1.21 ± 0.930 (6)* | 1.25 ± 0.294 (6)*,! | 2.10 ± 0.575 (6)! |
| 4 | 3.31 ± 0.945 (6)* | 1.02 ± 0.359 (6)*,# | 2.17 ± 1.101 (6) | 0.77 ± 0.443 (6)*,# | 0.55 ± 0.130 (6)*,#,! | 1.35 ± 0.484 (6)*,# |
| 5 | 3.38 ± 1.207 (6)* | 0.65 ± 0.269 (6)*,# | 2.13 ± 0.568 (5) | 0.85 ± 0.445 (6)*,# | 0.52 ± 0.109 (6)*,# | 1.06 ± 0.546 (6)*,# |
| 8 | 3.00 ± 1.566 (6) | 0.97 ± 0.248 (6)*,# | 3.18 ± 1.304 (5) | 1.24 ± 0.644 (6)*,# | 1.22 ± 0.239 (6)*,# | 1.29 ± 0.606 (5)# |

*Statistically Different from Predose (p < 0.05)
Statistically Different from Naïve (p < 0.05)
!Statistically significant from Doxorubicin alone (p < 0.05)

Figure 8:
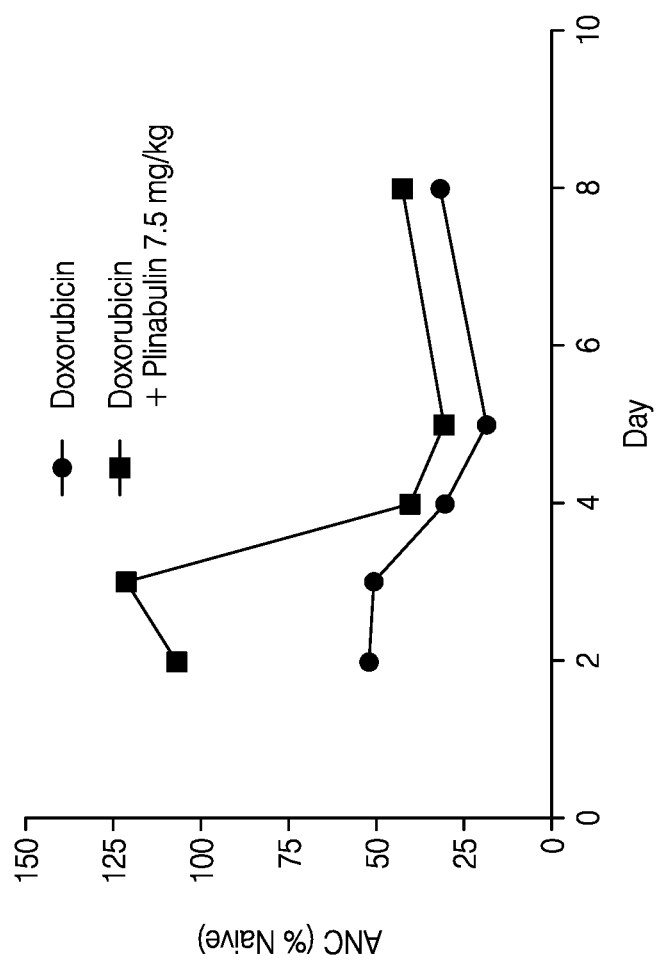
FIG. 8 is a graph of the time course of ANC level expressed as a percentage of the ANC level of the naïve group after administration of doxorubicin and the combination of doxorubicin and plinabulin.

As seen in Table 9 and FIG. 8, when expressed as percentage of ANC in Naïve animals, the neutropenia effect of doxorubicin was seen within 24 hours after administration and increased in severity until Day 5. Plinabulin (7.5 mg/kg) significantly diminished the effect of doxorubicin on Days 2 and 3 post dose, and ameliorated the doxorubicin-induced neutropenia to a lesser degree on days 5 and 8.

TABLE 9

ANC level in the treatment groups (7.5 mg/kg), expressed as Percent Naïve Group

| | Doxorubicin | | Doxorubicin + Plinabulin (7.5 mg/kg) | | |
|---|---|---|---|---|---|
| Day | % Naïve | p value | % Naïve | p value vs. Naïve | p value vs. Doxorubicin |
| 2 | 52.6 | 0.004 | 107.5 | NS | 0.0127 |
| 3 | 50.9 | 0.0019 | 121.4 | NS | 0.0005 |
| 4 | 30.8 | 0.0002 | 40.8 | 0.0011 | NS |
| 5 | 19.2 | 0.0003 | 31.4 | 0.0016 | NS |
| 8 | 32.3 | 0.0106 | 43.0 | 0.0489 | NS |

When the results were expressed as percent doxorubicin alone, a similar amelioration by plinabulin on doxorubicin-induced neutropenia was observed for the 7.5 mg/kg dose of plinabulin and also for the 3.5 mg/kg dose of plinabulin as shown in Table 10.

TABLE 10

ANC levels in the treatment groups, expressed as percent of the doxorubicin treated group

| | Doxorubicin + Plinabulin 1.75 mg/kg | | Doxorubicin + Plinabulin 3.5 mg/kg | | Doxorubicin + Plinabulin 7.5 mg/kg | |
|---|---|---|---|---|---|---|
| Day | % Dox Alone | p value | % Dox Alone | p value | % Dox Alone | p value |
| 2 | 100.5 | NS | 137.6 | NS | 204.3 | 0.0127 |
| 3 | 137.5 | NS | 142.0 | 0.0219 | 238.6 | 0.0005 |
| 4 | 75 | NS | 53.9 | NS | 132.0 | NS |
| 5 | 130.8 | NS | 80.0 | NS | 163.0 | NS |
| 8 | 127.8 | NS | 125.8 | NS | 133.0 | NS |

The doxorubicin induced a long-lasting neutropenia in the rat, when it was administered at a dose of 3.0 mg/kg. Plinabulin significantly reduced the doxorubicin-induced neutropenia as doses of 3.5 and 7.5 mg/kg IP, when administered one hour after doxorubicin.

Example 4

A study was performed to evaluate the effect of Plinabulin in reducing or treating cis-platin induced neutropenia. Male Sprague-Dawley rats were first treated with cis-platin or vehicle saline (control). The control sample included 7.1% Tween 80 (v/v), 25.5% Propylene glycol (v/v), 67.4% D5W (v/v). One hour later, the rats were dosed with Plinabulin or its vehicle following the administration schedule shown in Table 11. Each test group included 6 rats.

TABLE 11

Treatment groups

| Group | Treatment | Administration 1 | Administration 2 |
|---|---|---|---|
| a | Naïve control | — | — |
| b | Cis-platin + Vehicle | Cisplatin 6.5 mg/kg, (10 ml/kg) | Vehicle (TI), 7.5 ml/kg, Single, 1 h post cis-platin |
| c | Vehicle + Plinabulin | Vehicle (for cis-platin), 10 ml/kg | Plinabulin 4.9 mg/kg (4.9 ml/kg) |
| d | Cis-platin + Plinabulin | Cisplatin 6.5 mg/kg, (10 ml/kg) | Plinabulin 1.14 mg/kg (1.14 ml/kg) |
| e | Cis-platin + Plinabulin | Cisplatin 6.5 mg/kg, (10 ml/kg) | Plinabulin 4.9 mg/kg (4.9 ml/kg) |
| f | Vehicle + Plinabulin | Vehicle (for cis-platin), 10 ml/kg | Plinabulin 7.5 mg/kg (7.5 ml/kg) |
| g | Cis-Platin + Plinabulin | Cisplatin 6.5 mg/kg, (10 ml/kg) | Plinabulin 7.5 mg/kg (7.5 ml/kg) |

Blood collection was performed for ANC in blood samples collected at Day −1 (pre-dose), Day 2, Day 3, Day 4, and Day 5 post single dosing with control, cisplatin at Day 1 followed by plinabulin, or plinabulin vehicle as control one hour later. The ANC decreased following cisplatin administration. Table 12 shows the ANC of the different treatment groups at predose and Day 3.

TABLE 12

ANCs ($10^3$ Cells/μL) at Predose and Day 3 (Cisplatin ANC nadir) for the treatment groups

| Day | −1 | 3 |
|---|---|---|
| Control | 1.69 ± 0.41 | 1.46 ± 0.28 |
| Cisplatin | 2.03 ± 0.81 | 0.93 ± 0.28 |
| Plinabulin 4.9 mg/kg | 1.98 ± 0.47 | 2.42 ± 0.73 |
| Plinabulin 7.5 mg/kg | 2.12 ± 0.25 | 4.55 ± 1.41 |
| Cisplatin + Plinabulin 1.14 mg/kg | 2.03 ± 0.60 | 1.35 ± 0.38 |
| Cisplatin + Plinabulin 2.3 mg/kg | 2.07 ± 0.71 | 1.70 ± 0.63 |
| Cisplatin + Plinabulin 4.9 mg/kg | 2.04 ± 0.45 | 2.81 ± 1.24 |
| Cisplatin + Plinabulin 7.5 mg/kg | 1.55 ± 0.24 | 2.08 ± 0.55 |

Table 13 shows the ANC levels on Day 3 after treatment expressed as percentage of the baseline (Day −1 pretreatment)

TABLE 13

Day 3 ANCs Expressed as Percent of Baseline (Day −1), with Statistical significance (t-test)

| Group | Control | Cisplatin | Plinabulin 4.9 mg/kg | Plinabulin 7.5 mg/kg | Cisplatin + Plinabulin 1.14 mg/kg | Cisplatin + Plinabulin 2.3 mg/kg | Cisplatin + Plinabulin 4.9 mg/kg | Cisplatin + Plinabulin 7.5 mg/kg |
|---|---|---|---|---|---|---|---|---|
| % of Day −1 | 86.4 | 45.8 | 122.2 | 214.6 | 66.5 | 84.2 | 137.7 | 134.2 |
| P value based on ANC levels | 0.2933 NS | 0.0101 | 0.2391 NS | 0.0014 | 0.0417 | 0.3525 NS | 0.1837 NS | 0.0521 NS |

Figure 9:
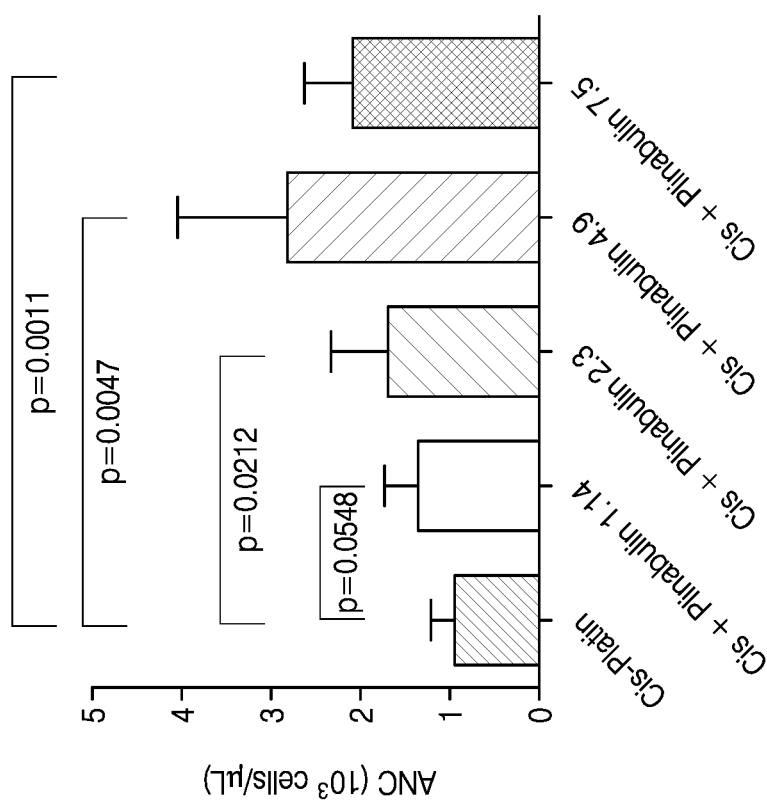
FIG. 9 shows the ANC levels on Day 3 post the administration of cisplatin, plinabulin, and the combination of cisplatin and plinabulin.
Figure 10:
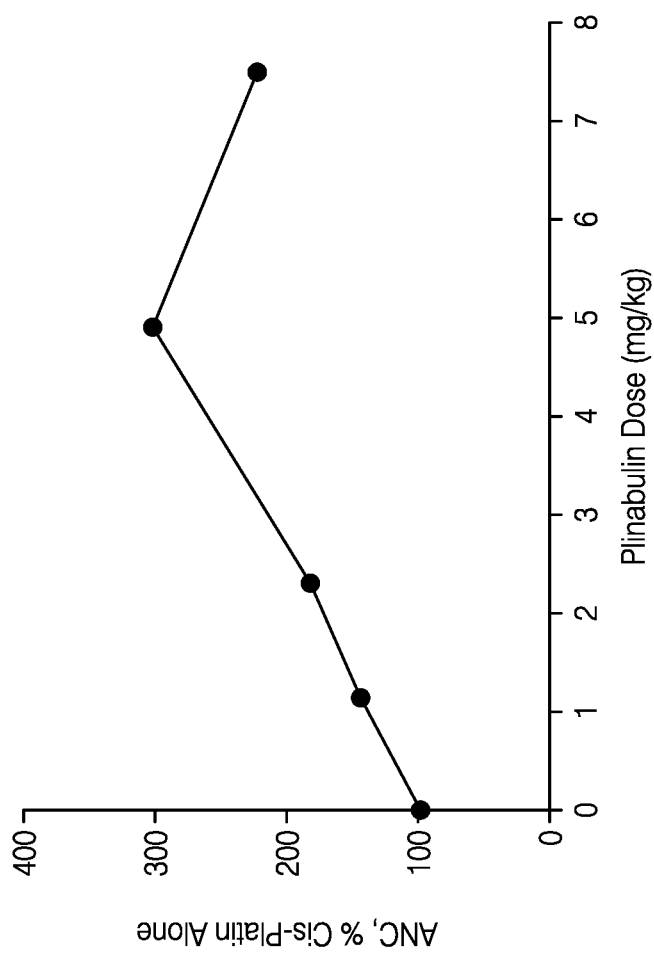
FIG. 10 shows a dose response curve for plinabulin on cisplatin induced neutropenia with the ANC level change expressed as percentage of the ANC level in cisplatin treatment alone group.

The ANC levels in the Control Group were not significantly different between predose and Day 3, and a direct comparison can be made between groups. Cisplatin at 6.5 mg/kg in the rat induced a statistically significant neutropenia on Day 3 post dosing. Plinabulin at 4.9 mg/kg did not change ANC levels. When plinabulin (2.3 mg/kg, 4.9 mg/kg and 7.5 mg/kg) was administered one hour post cisplatin, the ANC levels were not significantly different from the predose levels. Table 14 shows the ANC levels on Day 3 for various test groups. FIG. 9 shows the ANC levels on day 3 for the cisplatin alone group and the cis-platin and plinabulin combination groups. FIG. 10 shows the dose-response curve for plinabulin on cis-platin induced neutropenia in the rat, with the ANC data expressed as percentage of the ANC levels measured in the cis-platin only treatment group. When the ANC levels in the cis-platin and plinabulin combination dosed groups were expressed as the percent of ANC in the cis-platin alone group (Day 3), plinabulin exhibited a dose-response effect in decreasing the neutropenia observed in the cis-platin alone group.

TABLE 14

Effect of plinabulin on ANC Levels in the treatment groups, expressed as % of the cis-platin only treatment group.

| Comparison | Cis-platin vs. Cis + Plinabulin 1.14 | Cis-platin vs. Cis + Plinabulin 2.3 | Cis-platin vs. Cis + Plinabulin 4.9 | Cis-platin vs. Cis + Plinabulin 7.5 |
|---|---|---|---|---|
| ANC % of Cis-platin alone group (Day 3) | 145.2 | 182.8 | 302.2 | 223.7 |
| P value | 0.0548 NS | 0.212 | 0.0047 | 0.0011 |

At a dose of 6.5 mg/kg IP, cis-platin induced a statistically significant neutropenia. As shown in the study, plinabulin, in a dose-dependent manner, significantly reduced the cis-platin induced neutropenia.

Example 5

A study was performed to evaluate the effect of Plinabulin in reducing or treating topotecan induced neutropenia. The control sample contained 7.1% Tween 80 (v/v), 25.5% Propylene glycol (v/v), and 67.4% D5W (5% dextrose in water) (v/v). Topotecan (0.25 or 1.0 mg/kg IV) was administered to adult male Sprague-Dawley rats on Days 1, 3 and 5. Topotecan was administered by intravenous infusion over a period of 30 minutes using a syringe infusion pump and sterile disposable syringes at a dose volume of 10 mL/kg.

Plinabulin (3.75 mg/kg, IP) was dosed 1 hour post topotecan following each topotecan dose. Plinabulin (7.5 mg/kg IP) was dosed 1 hour after the topotecan dose (0.25 mg/kg) on Day 1 only.

Blood collection was performed Days −2, 0, 2, 4, 6, 7, 8, 9, 10 for the pilot and Days −2, 0, 2, 3, 4, 5, 6, 7, 8, 10, 15 for the main study. Blood samples collected on day 3 were analyzed for total and differential blood cell counts.

Figure 11A:
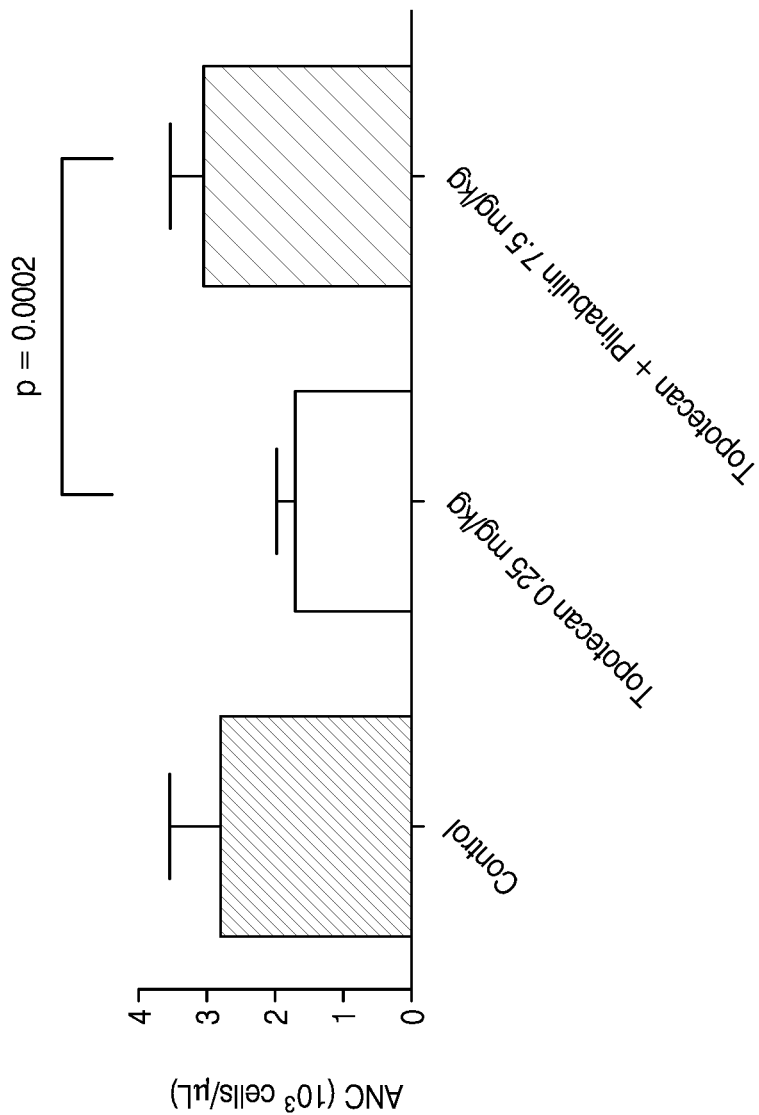
FIGS. 11A and 11B show the ANC levels post the administration of control, plinabulin, and the combination of topotecan and plinabulin.
Figure 11B:
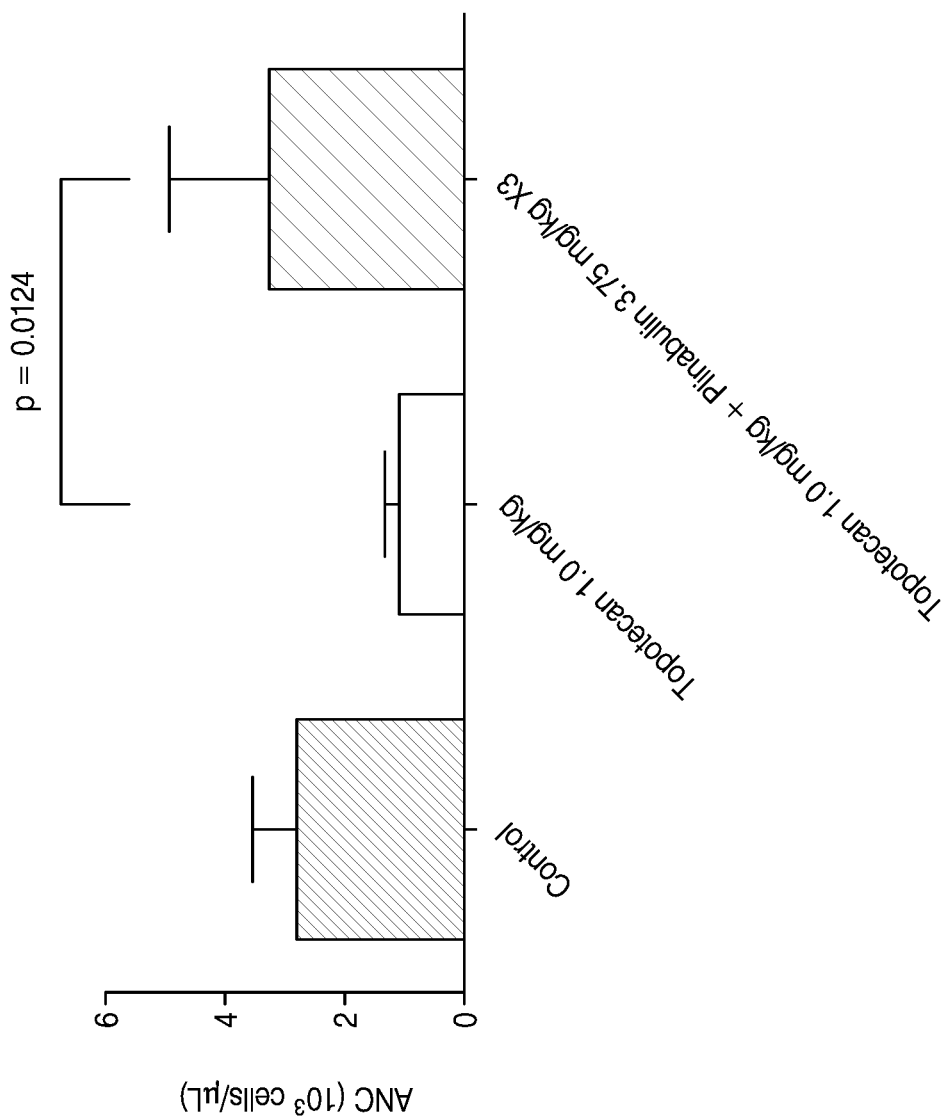

FIGS. 11A and 11B illustrate the change of ANC levels post the administration of control, plinabulin, and the combination of topotecan and plinabulin. As shown in FIGS. 11A and 11B, the topotecan induced a long-lasting neutropenia in the rat, when it was administered at a dose of 1 or 0.25 mg/kg. Plinabulin significantly reduced the topotecan-induced neutropenia as doses of 3.75 and 7.5 mg/kg IP, when administered one hour after topotecan.

Example 6

A study can be performed to evaluate the effect of Plinabulin in reducing or treating a test chemotherapeutic agent-induced neutropenia. An effective amount of the test chemotherapeutic agent is administered to a test subject (e.g., adult male Sprague-Dawley rats) on Days 1, 3 and 5. Plinabulin in the range of about 3.75 mg/kg to 40 mg/kg is dosed after the test chemotherapeutic agent is administered to the test subject. Blood collection is performed Days −2, 0, 2, 4, 6, 7, 8, 9, 10 for the pilot and Days −2, 0, 2, 3, 4, 5, 6, 7, 8, 10, 15 for the main study. Blood samples are analyzed for total and differential blood cell counts.

Example 7

A study can be performed to evaluate the effect of Plinabulin in reducing or treating a tecan compound induced neutropenia. An effective amount of the tecan compound is administered to a test subject (e.g., adult male Sprague-Dawley rats). Plinabulin in the range of about 3.75 mg/kg to 40 mg/kg is dosed after the tecan compound is administered to the test subject. Blood collection is performed Days −2, 0, 2, 4, 6, 7, 8, 9, 10 for the pilot and Days −2, 0, 2, 3, 4, 5, 6, 7, 8, 10, 15 for the main study. Blood samples are analyzed for total and differential blood cell counts.

Example 8

A study can be performed to evaluate the effect of Plinabulin in reducing or treating a platin compound induced neutropenia. An effective amount of the platin compound is administered to a test subject (e.g., adult male Sprague-Dawley rats) on Days 1, 3 and 5. Plinabulin in the range of about 3.75 mg/kg to 40 mg/kg is dosed after the platin compound is administered to the test subject. Blood collection is performed Days −2, 0, 2, 4, 6, 7, 8, 9, 10 for the pilot and Days −2, 0, 2, 3, 4, 5, 6, 7, 8, 10, 15 for the main study. Blood samples are analyzed for total and differential blood cell counts.

Example 9

A study can be performed to evaluate the effect of Plinabulin in reducing or treating a phosphamide compound induced neutropenia. An effective amount of the phosphamide compound is administered to a test subject (e.g., adult male Sprague-Dawley rats) on Days 1, 3 and 5. Plinabulin in the range of about 3.75 mg/kg to 40 mg/kg is dosed after the phosphamide compound is administered to the test subject. Blood collection is performed Days −2, 0, 2, 4, 6, 7, 8, 9, 10 for the pilot and Days −2, 0, 2, 3, 4, 5, 6, 7, 8, 10, 15 for the main study. Blood samples are analyzed for total and differential blood cell counts.

Example 10

A study can be performed to evaluate the effect of Plinabulin in reducing or treating a rubicin compound induced neutropenia. An effective amount of the rubicin compound is administered to a test subject (e.g., adult male Sprague-Dawley rats) on Days 1, 3 and 5. Plinabulin in the range of about 3.75 mg/kg to 40 mg/kg is dosed after the rubicin compound is administered to the test subject. Blood collection is performed Days −2, 0, 2, 4, 6, 7, 8, 9, 10 for the pilot and Days −2, 0, 2, 3, 4, 5, 6, 7, 8, 10, 15 for the main study. Blood samples are analyzed for total and differential blood cell counts.

Example 11

A study can be performed to evaluate the effect of Plinabulin in reducing or treating radiation therapy induced neutropenia. A radiation therapy is administered to a test subject (e.g., adult male Sprague-Dawley rats) on days 1, 3 and 5. Plinabulin in the range of about 3.75 mg/kg to 40 mg/kg is dosed after the radiation is administered to the test subject. Blood collection is performed Days −2, 0, 2, 4, 6, 7, 8, 9, 10 for the pilot and Days −2, 0, 2, 3, 4, 5, 6, 7, 8, 10, 15 for the main study. Blood samples are analyzed for total and differential blood cell counts.

What is claimed is:

1. A method of reducing neutropenia in a subject, comprising administering plinabulin or a pharmaceutically acceptable salt thereof to the subject,
    wherein the neutropenia is induced by administration of a first chemotherapeutic composition comprising one or more chemotherapeutic agents,
    wherein the first chemotherapeutic composition comprises one or more agents selected from the group consisting of cyclophosphamide, ifosamide, cisplatin, carboplatin, oxaliplatin, nedaplatin, triplatin tetranitrate, phenanthriplatin, picoplatin, satraplatin, topotecan, doxorubicin, epirubicin, daunorubicin, valrubicin, and pharmaceutically acceptable salts thereof,
    or by administration of radiation therapy.

2. The method of claim 1, wherein the first chemotherapeutic composition does not comprise a taxane.

3. The method of claim 1, comprising administering one or more additional chemotherapeutic compositions to the subject.

4. The method of claim 1, wherein the first chemotherapeutic composition comprises a single chemotherapeutic agent.

5. The method of claim 1, wherein the first chemotherapeutic composition comprises two or more chemotherapeutic agents.

6. The method of claim 3, wherein the at least one of the one or more additional chemotherapeutic compositions comprises docetaxel.

7. The method of claim 3, wherein at least one of the one or more additional chemotherapeutic compositions comprises one or more taxanes selected from the group consisting of docetaxel, paclitaxel, and cabazitaxel.

8. The method of claim 1, wherein the first chemotherapeutic composition comprises cyclophosphamide.

9. The method of claim 1, wherein the first chemotherapeutic composition comprises cisplatin.

10. The method of claim 1, wherein the first chemotherapeutic composition comprises doxorubicin.

11. The method of claim 1, wherein the first chemotherapeutic composition comprises topotecan.

12. The method of claim 1, comprising administering plinabulin prior to administering the first chemotherapeutic composition.

13. The method of claim 12, wherein the plinabulin is administered in the range of about 1 minute to 24 hours prior to administration of the first chemotherapeutic composition.

14. The method of claim 1, comprising administering plinabulin after administering the first chemotherapeutic composition.

15. The method of claim 14, wherein the plinabulin is administered in the range of about 1 minute to 24 hours after administration of the first chemotherapeutic composition.

16. The method of claim 1, wherein the plinabulin and the first chemotherapeutic composition are co-administered.

17. The method of claim 3, comprising:
    administering plinabulin prior to administration of the first chemotherapeutic composition; and
    administering the additional one or more chemotherapeutic compositions after administration of the first chemotherapeutic composition.

18. The method of claim 3, comprising:
    administering the first chemotherapeutic composition prior to administration of the plinabulin; and
    administering the additional one or more chemotherapeutic compositions after administration of the plinabulin.

19. The method of claim 3, comprising:
    administering the first chemotherapeutic composition prior to administration of the additional one or more chemotherapeutic compositions; and
    administering the plinabulin after administration of the additional one or more chemotherapeutic agents.

20. The method of claim 17, wherein a period of time between administration of each of plinabulin, the first chemotherapeutic composition, and the additional one or more chemotherapeutic compositions is independently selected between about 1 minute and 24 hours.

21. The method of claim 1, comprising administering radiation therapy to the subject.

22. The method of claim 1, further comprising identifying the subject as suffering from neutropenia.

23. The method of claim 1, wherein the neutropenia induced by the first chemotherapeutic composition is a grade 3 or 4 neutropenia.

24. The method of claim 1, further comprising identifying the subject as being at risk for developing neutropenia.

25. The method of claim 1, wherein said reducing neutropenia further comprises reducing the likelihood of onset of, or reducing the severity of, neutropenia in the subject.

* * * * *

UNITED STATES PATENT AND TRADEMARK OFFICE
CERTIFICATE OF CORRECTION

PATENT NO. : 11,229,642 B2
APPLICATION NO. : 16/307440
DATED : January 25, 2022
INVENTOR(S) : Lan Huang It is certified that error appears in the above-identified patent and that said Letters Patent is hereby corrected as shown below:

On the Title Page

On Page 3, Column 1, Line 15, under Other Publications, delete "Ariloxy" and insert --Aryloxy--.

On Page 3, Column 1, Line 17, under Other Publications, delete "Chern" and insert --Chem--.

On Page 3, Column 1, Line 55, under Other Publications, delete "thereapy:" and insert --therapy:--.

On Page 3, Column 1, Line 66, under Other Publications, delete "clinicaltriais." and insert --clinicaltrials.--.

On Page 3, Column 2, Line 3, under Other Publications, delete "plinabuilin" and insert --plinabulin--.

On Page 3, Column 2, Line 38, under Other Publications, delete "Microvasc" and insert --Microvascular--.

On Page 3, Column 2, Line 48, under Other Publications, delete "IFN-(" and insert --IFN-y--.

On Page 4, Column 1, Line 3, under Other Publications, delete "Japnaese" and insert --Japanese--.

On Page 4, Column 2, Line 3, under Other Publications, delete "134-41." and insert --134-141.--.

On Page 4, Column 2, Line 52, under Other Publications, delete "Viro" and insert --Vitro--.

On Page 4, Column 2, Line 64, under Other Publications, delete "Koeppenhofer," and insert --Koppenhofer,--.

On Page 4, Column 2, Line 64, under Other Publications, delete "eininge" and insert --einige--.

On Page 4, Column 2, Line 71, under Other Publications, delete "Kiketopiperazine" and insert Signed and Sealed this
Ninth Day of August, 2022

Katherine Kelly Vidal
*Director of the United States Patent and Trademark Office*

--Diketopiperazine--.

On Page 5, Column 1, Line 13, under Other Publications, delete "Chern." and insert --Chem.--.

On Page 5, Column 1, Line 66, under Other Publications, delete "antimocrotubule" and insert --antimicrotubule--.

On Page 5, Column 2, Line 33, under Other Publications, delete "Ciin" and insert --Clin--.

On Page 5, Column 2, Line 69, under Other Publications, delete "Phospatases" and insert --Phosphatases--.

On Page 6, Column 1, Line 28, under Other Publications, delete "Qncotogy(2010)," and insert --Oncology (2010),--.

On Page 6, Column 1, Line 29, under Other Publications, delete "Purifiied" and insert --Purified--.

On Page 6, Column 2, Line 14, under Other Publications, delete "Plinabuilin" and insert --Plinabulin--.

On Page 7, Column 1, Line 12, under Other Publications, delete "cylophosphamide" and insert --cyclophosphamide--.

On Page 7, Column 1, Line 35, under Other Publications, delete "pegilgrastim (neulata)" and insert --pegfilgrastim (neulasta)--.

On Page 7, Column 2, Line 30, under Other Publications, delete "Preclinicai" and insert --Preclinical--.

In the Specification

In Column 8, Line 37, delete "ifosfamine," and insert --ifosfamide,--.

In Column 8, Line 44, delete "irincotecan," and insert --irinotecan,--.

In Column 8, Lines 45-46, delete "irincotecan/" and insert --irinotecan/--.

In Column 8, Line 55, delete "ciaplatin/" and insert --cisplatin/--.

In Column 9, Line 1, delete "irincotecan," and insert --irinotecan,--.

In Column 9, Line 26, delete "ifosfamine," and insert --ifosfamide,--.

In Column 9, Line 32, delete "irincotecan," and insert --irinotecan,--.

In Column 9, Line 33, delete "irincotecan/" and insert --irinotecan/--.

CERTIFICATE OF CORRECTION (continued)
U.S. Pat. No. 11,229,642 B2

In Column 9, Line 43, delete "ciaplatin/" and insert --cisplatin/--.

In Column 9, Line 53, delete "irincotecan," and insert --irinotecan,--.

In Column 14, Line 17, delete "0.25-0.75 h, 0.25-1" and insert --0.25 h-0.75 h, 0.25 h-1--.

In Column 14, Line 27, delete "0.25-0.75 h, 0.25-1" and insert --0.25 h-0.75 h, 0.25 h-1--.

In Column 18, Line 33, delete "350%" and insert --350%,--.

In Column 18, Line 40, delete "350%" and insert --350%,--.

In Column 18, Line 46, delete "350%" and insert --350%,--.

In Column 18, Line 52, delete "350%" and insert --350%,--.

In Column 18, Line 63, delete "350%" and insert --350%,--.

In Column 19, Line 6, delete "350%" and insert --350%,--.

In Column 19, Line 16, delete "350%" and insert --350%,--.

In Column 19, Line 28, delete "350%" and insert --350%,--.

In Column 19, Line 39, delete "350%" and insert --350%,--.

In Column 19, Line 50, delete "350%" and insert --350%,--.

In Column 20, Line 20, delete "intrapulmonarilly," and insert --intrapulmonarily,--.

In Column 20, Line 66, delete "ifosamide," and insert --ifosfamide,--.

In Column 21, Line 64, delete "subject" and insert --subject.--.

In Column 22, Line 26, delete "intrapulmonarilly," and insert --intrapulmonarily,--.

In Column 25, Line 42, delete "croscarmelose;" and insert --croscarmellose;--.

In Column 30, Line 12, delete "cyclophaphamide." and insert --cyclophosphamide.--.

In the Claims

In Column 37, Claim 1, Line 57, delete "ifosamide," and insert --ifosfamide,--.